US012779029B2

(12) United States Patent
He et al.

(10) Patent No.: US 12,779,029 B2
(45) Date of Patent: Nov. 3, 2026

(54) RECOMBINANT RSV VACCINE: METHODS OF MAKING AND USING THE SAME

(71) Applicant: BLUE LAKE BIOTECHNOLOGY, INC., Athens, GA (US)

(72) Inventors: Biao He, Athens, GA (US); Hong Jin, Cupertino, CA (US); Maria Cristina Gingerich, Athens, GA (US)

(73) Assignee: BLUE LAKE BIOTECHNOLOGY, INC., Athens, GA (US)

( * ) Notice: Subject to any disclaimer, the term of this patent is extended or adjusted under 35 U.S.C. 154(b) by 414 days.

(21) Appl. No.: 18/501,677

(22) Filed: Nov. 3, 2023

(65) Prior Publication Data

US 2024/0148857 A1 May 9, 2024

Related U.S. Application Data

(60) Provisional application No. 63/382,453, filed on Nov. 4, 2022.

(51) Int. Cl.

| | |
|---|---|
| ***A61K 39/175*** | (2006.01) |
| ***A61K 9/00*** | (2006.01) |
| ***A61K 39/155*** | (2006.01) |
| ***A61P 31/14*** | (2006.01) |
| ***A61P 37/04*** | (2006.01) |
| ***C07K 14/005*** | (2006.01) |
| ***C07K 14/135*** | (2006.01) |

(Continued)

(52) U.S. Cl.

CPC .......... *A61K 39/175* (2013.01); *A61K 9/0043* (2013.01); *A61K 39/155* (2013.01); *A61P 31/14* (2018.01); *A61P 37/04* (2018.01); *C07K 14/005* (2013.01); *C07K 14/135* (2013.01); *C12N 7/00* (2013.01); *C12N 15/86* (2013.01); *A61K 2039/5256* (2013.01); *A61K 2039/543* (2013.01); *A61K 2039/545* (2013.01); *C12N 2760/18043* (2013.01); *C12N 2760/18522* (2013.01); *C12N 2760/18534* (2013.01)

(58) Field of Classification Search

None

See application file for complete search history.

(56) References Cited

U.S. PATENT DOCUMENTS

2020/0377908 A1 12/2020 He
2023/0105376 A1 4/2023 Li et al.

(Continued)

FOREIGN PATENT DOCUMENTS

RU 2528750 C2 12/2012
WO 2010058099 A1 5/2010

(Continued)

OTHER PUBLICATIONS

Chen et al. (Scientific Reports. Mar. 14, 2018; 8 (1): 4491).*

(Continued)

*Primary Examiner* — Shanon A. Foley

(74) *Attorney, Agent, or Firm* — Judy Jarecki-Black; Sharon Ngwenya; Klintworth & Rozenblat LLP

(57) ABSTRACT

Compositions and methods of inducing an immune response in a subject having RSV comprising administering a pharmaceutical composition comprising a prophylactic vaccine against RSV infection, wherein the vaccine comprises a live recombinant canine parainfluenza (CPI) vector backbone engineered to express a RSV F protein.

16 Claims, 23 Drawing Sheets

Specification includes a Sequence Listing.

(51) Int. Cl.
*C12N 7/00* (2006.01)
*C12N 15/86* (2006.01)
*A61K 39/00* (2006.01)

(56) References Cited

U.S. PATENT DOCUMENTS

2024/0148857 A1* 5/2024 He .......................... A61P 31/14
2024/0287544 A1 8/2024 He et al.

FOREIGN PATENT DOCUMENTS

WO 2012116253 A2 8/2012
WO 2013112690 A1 8/2013
WO 2013112720 A1 8/2013
WO 2022061264 A1 3/2022
WO 2023044505 A2 3/2023
WO 2024167866 A2 8/2024
WO 2025076466 A2 4/2025

OTHER PUBLICATIONS

Chuang et al. (Biotechnology Letters. 2013; 35: 1541-1549).*
Boyle et al. (BMC Biotechnology. 2009; 9: 75).*
Li et al. (Journal of Virology. 2013; 87 (1): 354-362).*
Chen (Reviews in Medical Virology. 2018; 28 (2): e1965).*
Phan et al. (Journal of Virology. 2017; 91 (19): 10-128).*
Wang et al. (Journal of virology. 2017; 91 (11): 10-128).*
International Search Report and Written Opinion received for PCT Patent Application No. PCT/US23/78661, mailed on Feb. 23, 2024, 8 pages.
Office Action issued in connection with Vietnam application No. 121178/SHTT-SC and machine translation thereof, dated Aug. 27, 2025, 03 pages.
Spearman et al., "Intranasal parainfluenza virus type 5 (PIV5)-vectored RSV vaccine is safe and immunogenic in healthy adults in a phase 1 clinical study," Sci. Adv., vol. 9 2023, 11 pages.
Bagga, B., et al., "Effect of Preexisting Serum and Mucosal Antibody on Experimental Respiratory Syncytial Virus (RSV) Challenge and Infection of Adults," J. Infect. Dis., vol. 212, 2015, pp. 1719-1725.
Baumgartner, W., et al., "Persistent Infection of Vero Cells by Paramyxoviruses: A Morphological and Immunoelectron Microscopic Investigation," Intervirology, vol. 27, 1987, pp. 218-223. (Abstract Only; 1987).
Binn, L.N., et al., "Viruses Recovered from Laboratory Dogs with Respiratory Disease," Proc. Soc. Exp. Biol. Med., vol. 126, 1967 pp. 140-145 (Summary Only; 1967).
Boyce, T.G., et al., "Rates of hospitalization for respiratory syncytial virus infection among children in Medicaid," J. Pediatr., vol. 137, No. 6, 2000, pp. 865-870.
Bukreyev, A., et al., "Expression of Interleukin-4 by Recombinant Respiratory Syncytial Virus Is Associated with Accelerated Inflammation and a Nonfunctional Cytotoxic T-Lymphocyte Response following Primary Infection but Not following Challenge with Wild-Type Virus," J. Virol, vol. 79, No. 15, 2005, pp. 9515-9526.
Calder, L.J., et al., "Electron Microscopy of the Human Respiratory Syncytial Virus Fusion Protein and Complexes That It Forms with Monoclonal Antibodies," Virology, vol. 271, 2000, pp. 122-131.
Chatziandreou, N., et al., "Relationships and host range of human, canine, simian and porcine isolates of simian virus 5 (parainfluenza virus 5)," J. Gen. Virol., vol. 85, No. 10, 2004, pp. 3007-3016.
Chen, Z., et al., "A Novel Rabies Vaccine Based on a Recombinant Parainfluenza Virus 5 Expressing Rabies Virus Glycoprotein," J. Virol., vol. 87, No. 6, 2013, 8 pages.
Chen, Z., et al., "Efficacy of parainfluenza virus 5 (PIV5)-based tuberculosis vaccines in mice," Vaccine, vol. 33, No. 51, 2015, pp. 7217-7224.
Chin, J., et al., "Field Evaluation Of A Respiratory Syncytial Virus Vaccine And A Trivalent Parainfluenza Virus Vaccine In A Pediatric Population," Am. J. Epidemiol., vol. 89, No. 4, 1969, pp. 449-463. (Abstract Only; 1969).
Choppin, P.W., "Multiplication of a myxovirus (SV5) with minimal cytopathic effects and without interference," Virology, vol. 23, 1964, pp. 224-233. (Abstract Only; 1964).
Cifuentes, L., et al., "Risk factors for recurrent wheezing following acute bronchiolitis: a 12-month follow-up," Pediatr. Pulmonol., vol. 36, No. 4, 2003, pp. 316-321.
Ellis, S.E., et al., "Influenza-and Respiratory Syncytial Virus-Associated Morbidity and Mortality in the Nursing Home Population," J. Am. Geriatr. Soc., vol. 51, No. 6, 2003, pp. 761-767.
Evermann, J.F., et al., "Isolation of a paramyxovirus from the cerebrospinal fluid of a dog with posterior paresis.," J. Am. Vet. Med. Assoc., vol. 177, 1980, pp. 1132-1134. (Abstract Only; 1980).
Evermann, J.F., et al., "Properties of an encephalitogenic canine parainfluenza virus," Arch. Virol., vol. 68, 1981, pp. 165-172. (Abstract Only; 1981).
Falsey, A.R., et al., "Respiratory syncytial virus and influenza A infections in the hospitalized elderly," J. Infect. Dis., vol. 772, No. 2, 1995, pp. 389-394.
Garofalo, R., et al., "Peripheral blood eosinophil counts and eosinophil cationic protein content of respiratory secretions in bronchiolitis: relationship to severity of disease," Pediatr. Allergy Immunol., vol. 5, No. 2, 1994, pp. 111-117 (Abstract Only; 1994).
Groothuis, J.R., et al., "Respiratory Syncytial Virus Infection in Children With Bronchopulmonary Dysplasia," Pediatrics, vol. 82, No. 2, 1988, pp. 199-203.
Hall, C.B., et al., "Immunity to and Frequency of Reinfection with Respiratory Syncytial Virus," J. Infect. Dis., vol. 163, No. 4, 1991, pp. 693-698.
He, B., et al., "Recovery of Infectious SV5 from Cloned DNA and Expression of a Foreign Gene," Virology, vol. 237, No. 2, 1997, pp. 249-260.
Kapikian, A.Z., et al., "An Epidemiologic Study of Altered Clinical Reactivity To Respiratory Syncytial (Rs) Virus Infection In Children Previously Vaccinated With An Inactivated Rs Virus Vaccine," Am. J. Epidemiol, vol. 89, No. 4, 1969, pp. 405-421 (Abstract Only; 1969).
Karron, R.A., et al., "Identification of a Recombinant Live Attenuated Respiratory Syncytial Virus Vaccine Candidate That Is Highly Attenuated in Infants," J. Infect. Dis., vol. 191, No. 7, 2005, pp. 1093-1104.
Kim, H.W., et al., "Respiratory Syncytial Virus Disease In Infants Despite Prior Administration Of Antigenic Inactivated Vaccine," Am. J. Epidemiol., vol. 89, No. 4, 1969, pp. 422-434 (Abstract Only; 1969).
Lafontaine, E.R., et al., "The autotransporter protein BatA is a protective antigen against lethal aerosol infection with Burkholderia mallei and Burkholderia pseudomallei," Vaccine X., vol. 1, 100002 2018, 10 pages.
Li, K., et al., "Single-Dose, Intranasal Immunization with Recombinant Parainfluenza Virus 5 Expressing Middle East Respiratory Syndrome Coronavirus (MERS-CoV) Spike Protein Protects Mice from Fatal MERS-CoV Infection," mBio, vol. 11, No. 2, 2020, pp. 1-12.
Li, Z., et al., "Recombinant Parainfluenza Virus 5 Expressing Hemagglutinin of Influenza A Virus H5N1 Protected Mice against Lethal Highly Pathogenic Avian Influenza Virus H5N1 Challenge," J. Virol., vol. 87, No. 1, 2013, pp. 354-362.
MacDonald, N.E., et al., "Respiratory Syncytial Viral Infection in Infants with Congenital Heart Disease," N. Engl. J. Med, vol. 307, No. 1, 1982, pp. 397-400.
Mcintosh, K., et al., "The association of viral and bacterial respiratory infections with exacerbations of wheezing in young asthmatic children," J. Pediatr., vol. 82, No. 4, 1973, pp. 578-590.
Muelenaer, P.M., et al., "Group-Specific Serum Antibody Responses in Children with Primary and Recurrent Respiratory Syncytial Virus Infections," J. Infect. Dis., vol. 164, 1991, pp. 15-21.
Navas, L., et al., "Improved outcome of respiratory syncytial virus infection in a high-risk hospitalized population of Canadian children," J. Pediatr., vol. 121, No. 3, 1992, pp. 348-354.
Phan, S.I., et al., "A respiratory syncytial virus (RSV) vaccine based on parainfluenza virus 5 (PIV5)," Vaccine, vol. 32, 2014, pp. 3050-3057.

(56) References Cited

OTHER PUBLICATIONS

Phan, S.I., et al., "Parainfluenza virus 5 expressing wild-type of prefusion respiratory syncytial virus (RSV) fusion protein protects mice and cotton rats from RSV challenge," J. of Virology, vol. 91, No. 19, 2017, 17 pages.
Polack, F.P., et al., "A role for immune complexes in enhanced respiratory syncytial virus disease," J. Exp. Med., vol. 196, 2002, pp. 859-865.
Schauer, U., et al., "RSV bronchiolitis and risk of wheeze and allergic sensitisation in the first year of life," Eur. Respir. J., vol. 20, No. 5, 2002, pp. 1277-1283.
Schmitt, A.P., et al., "Requirements for Budding of Paramyxovirus Simian Virus 5 Virus-Like Particles," J. of Virology, vol. 76, 2002, pp. 3952-3964.
Seth, S., et al., "Mutations in the cytoplasmic domain of a paramyxoviruses fusion glycoprotein rescue syncytium formation and eliminate the HN requirement for membrane fusion," J. of Virology, 2003, pp. 167-178.
Shay, D.K., et al., "Bronchiolitis-Associated Hospitalizations Among US Children, 1980-1996," JAMA, vol. 282, No. 5, 1999, pp. 1440-1446.
Sigurs, N., et al., "Asthma and Immunoglobulin E Antibodies After Respiratory Syncytial Virus Bronchiolitis: A Prospective Cohort Study With Matched Controls," Pediatrics, vol. 95, No. 4, 1995, pp. 500-505.
Sigurs, N., et al., "Respiratory Syncytial Virus Bronchiolitis in Infancy Is an Important Risk Factor for Asthma and Allergy at Age 7," Am. J. Respir. Crit. Care Med., vol. 161. No. 5, 2000, pp. 1501-1507.
Stein, R.T., et al., "Respiratory syncytial virus in early life and risk of wheeze and allergy by age 13 years," Lancet, vol. 354, No. 9178, 1999, pp. 541-545.
Tong, S., et al., "Regulation of Fusion Activity by the Cytoplasmic Domain of a Paramyxovirus F Protein," J. of Virology, vol. 301, 2002, pp. 322-333.
Tristram, D.A., et al., "Second-year surveillance of recipients of a respiratory syncytial virus (RSV) F protein subunit vaccine, PFP-1: Evaluation of antibody persistence and possible disease enhancement," Vaccine, vol. 12, No. 6, 1994, pp. 551-556.
Wang, D., et al., "A single-dose recombinant parainfluenza virus 5-vectored vaccine expressing respiratory syncytial virus (RSV) F or G protein protected Cotton rats and African green monkeys from RSV challenge," J. of Virology, vol. 91, No. 11, 2017, 15 pages.
Waning, D.L., et al., "Roles for the cytoplasmic tails of the fusion and hemagglutinin-neuraminidase proteins in budding of the paramyxovirus simian virus 5," J. Virol., vol. 76, 2002, pp. 9284-9297.
Welliver, R.A., et al., "The relationship of RSV-specific immunoglobulin E antibody responses in infancy, recurrent wheezing, and pulmonary function at age 7-8 years," Pediatr. Pulmonol., vol. 15, No. 1, 1993, pp. 19-27 (Abstract Only; 1993).
Whelan, S.P.J., et al., "Transcription and Replication of Nonsegmented Negative-Strand RNA Viruses," Curr. Top. Microbiol. Immunol., vol. 283, 61-119 (Abstract Only; 2004).
Xiao, P., et al., "Parainfluenza Virus 5 Priming Followed by SIV/HIV Virus-Like-Particle Boosting Induces Potent and Durable Immune Responses in Nonhuman Primates," Front. Immunol., vol. 12, 2021, 15 pages.
Young, D., et al., "The switch between acute and persistent paramyxovirus infection caused by single amino acid substitutions in the RNA polymerase P subunit," PLoS Pathogens, vol. 15, No. 2, 2019, 15 pages.
Restriction Requirement received in U.S. Appl. No. 17/933,812, mailed Oct. 31, 2025, 6 pages.
Phan, S. et al., "Genetic Stability of Parainfluenza Virus 5-Vectored Human Respiratory Syncytial Virus Vaccine Candidates after In Vitro and In Vivo Passate," Journal of Virology. 91(19):1-14 (2017).
Search Report received in Iranian Patent Application No. 140450140003001026, mailed Jan. 11, 2026, including English Translation (1 page of Notice; 7 pages of Original; 8 pages of Translation).
Office Action received in Russian Patent Application No. 2025114631, mailed Nov. 12, 2025, including English Translation. (12 pages).
Office Action received in Russian Patent Application No. 2025114631, mailed Apr. 20, 2026.
Search Report received in Russian Patent Application No. 2025114631, mailed Apr. 20, 2026.
Office Action received in Japanese Patent Application No. 2025-526222, mailed Apr. 14, 2026, 7 pages of original documents, 9 pages of translation.
Chen, et al., "Parainfluenza virus 5—vectored vaccines against human animal infectious diseases" Rev Med Virol, 28:e1965 (2018).
Blue Lake Biotechnology Announces FDA Fast Track Designation for BLB-201 Intranasal RSV Vaccine, Blue Lake Technology news, May 24, 2022, URL:https://www.bluelaketechnology.com/news/blue-lakebiotechnology-announces-fda-fast-track-designation-for-blb-201-intranasal-rsv-vaccineez8yx.

* cited by examiner

RECOMBINANT RSV VACCINE: METHODS OF MAKING AND USING THE SAME

REFERENCE TO RELATED APPLICATIONS

This application claims benefit of and priority to U.S. Provisional Application No. 63/382,453 filed on Nov. 4, 2022, which is incorporated by reference in its entirety.

REFERENCE TO A SEQUENCE LISTING

The application contains a Sequence Listing which has been submitted electronically in XML format and is hereby incorporated by reference in its entirety. Said. XML copy, created on Nov. 2, 2023, is named "065095.004PCT.xml" and is 42,181 bytes in size. The sequence listing contained in this .XML file is part of the specification and is hereby incorporated by reference herein in its entirety.

FIELD

This invention relates generally to field of immunomodulation, and more particularly to compositions and methods for modulating immune responses against diseases from a respiratory syncytial virus (RSV) infection.

BACKGROUND

Human RSV is the leading viral cause of lower respiratory illness and hospitalization in young children. The vast majority of children infected with RSV suffer from a mild upper respiratory tract infection; however, a small subset experience severe RSV-induced lower respiratory infection (LRI) and bronchiolitis that often requires hospitalization and can be life-threatening (Collins et al., Respiratory syncytial virus, In: Fields Virology, Knipe and Howley, eds., Lippincott Williams & Wilcins, New York (1996), pp. 1313-1351). Since nearly every child eventually is infected with RSV, and significant LRI develops in 20-30% of RSV-infected children, RSV causes more than 130,000 pediatric hospitalizations annually in the United States (Shay et al., JAMA, 282 (5): 1440-1446 (1999), and World Health Organization, Initiative for Vaccine Research (IVR), Respiratory syncytial virus (RSV).

Some risk factors for the development of severe RSV-induced illness have been clearly identified, including premature birth (Navas et al., J. Pediatr., 121 (3): 348-54 (1992)), bronchopulmonary dysplasia (Groothuis et al., Pediatrics, 82 (2): 199-203 (1988)), congenital heart disease (MacDonald et al., N. Engl. J. Med, 307 (1): 397-400 (1982)), and T cell immune deficiency (Mcintosh et al., J. Pediatr., 82 (4): 578-90 (1973)). However, more than half of the children hospitalized with severe RSV-induced illness do not have an identified risk factor (Boyce et al., J. Pediatr., 137 (6): 865-70 (2000)), which means that approximately 1-2% of otherwise healthy children without any identifiable risk factors suffer the potentially life-threatening consequences of RSV-induced illness (Collins et al., supra).

RSV-induced severe illness in children also has been correlated with the development of asthma (see, e.g., Sigurs et al., Pediatrics, 95 (4): 500-505 (1995); Welliver et al., Pediatr. Pulmonol, 15 (1): 19-27 (1993); Cifiientes et al., Pediatr. Pulmonol, 36 (4): 316-321 (2003); Schauer et al., Eur. Respir. J., 20 (5): 1277-1283 (2002); Sigurs et al., Am. J. Respir. Crit. Care Med., 161 (5): 1501-1507 (2000); and Stein et al., Lancet, 354 (9178): 541-545 (1999)). The basis for this association is unknown, but may be due to underlying genetic factors, immune dysfunction, antigen-specific responses, or structural lesions caused by lung remodeling after severe RSV disease.

Although RSV infection is almost universal by age three, reinfection occurs throughout life because natural RSV infection does not provide complete immunity (Hall et al., J. Infect. Dis., 163 (4): 693-698 (1991), and Muelenaer et al., J. Infect. Dis., 164:15-21 (1991)). In the elderly, RSV is an important cause of morbidity and mortality. In a retrospective cohort study, RSV was responsible for an annual average of IS hospitalizations and 17 deaths per 1,000 nursing home residents, whereas influenza accounted for an average of 28 hospitalizations and 15 deaths in the same setting (Garofalo et al., Pediatr. Allergy Immunol., 5 (2): 111-117 (1994). Thus, RSV was isolated as frequently as influenza A in this population and was associated with comparable mortality as influenza A (Ellis et al., J. Am. Geriatr. Soc, 51 (6): 761-72003; and Falsey et al., J. Infect. Dis., 772 (2): 389-394 (1995)).

Currently there are no FDA-approved vaccines for the prevention of RSV infection or treatment of RSV-induced disease in children. The only FDA-approved medication for prophylaxis of RSV infection is SYNAGIS® (palivizumab) (MedImmune, Gaithersburg, MD), which is a humanized monoclonal antibody directed to an epitope in the A antigenic site of the RSV F protein administered to high-risk infants. Although SYNAGIS® represents a significant advance in the prevention of lower respiratory tract acute RSV disease and mitigation of lower respiratory tract infection, it has not been shown to be effective against RSV infection in the upper respiratory tract at permissible doses. In 2023, FDA approved half-life extended long-acting RSV monoclonal antibody Beyfortus (nirsevimab), which was recommended for all infants aged <8 months who are born during or entering their first RSV season and for infants and children aged 8-19 months who are at increased risk for severe RSV disease and are entering their second RSV season.

RSV vaccine development has suffered from a legacy of vaccine-enhanced disease in children after natural RSV infection (Kim et al., Am. J. Epidemiol, 89 (4): 422-434 (1969); and Kapikian et al., Am. J. Epidemiol, 89 (4): 405-421 (1969)). For example, in the early 1960s a formalin-inactivated alum-precipitated vaccine candidate (FI-RSV) was administered to RSV-naïve infants in the early 1960s, and although immunogenic, it did not protect the children against natural infection. In addition, vaccinees subsequently infected with RSV had increased hospitalization rates and more severe illness, including two deaths, relative to control children immunized with formalin-inactivated parainfluenza virus (Kapikian et al., supra, Chin et al., Am. J. Epidemiol., 89(4):449-463 (1969); and Polack et al., J. Exp. Med, 196(6):859-65 (2002)). Other approaches to RSV immunization have included live attenuated RSV, RSV subunit proteins, and parainfluenza virus chimeras. Live attenuated RSV vaccines have been tested in clinical trials of RSV-naïve infants, but have not been shown to achieve genetic stability of mutations, the optimal balance between attenuation for safety in infants, or a protective immune response (Karron et al., J. Infect. Dis., 191(7): 1093-1104 (2005); and Bukreyev et al., J. Virol, 79(15):9515-9526 (2005)). Protein subunit vaccines based on RSV G and F proteins have been safely administered to adults and RSV-seropositive children, but are modestly immunogenic (Tristram et al., Vaccine, 12(6):551-556 (1994)).

Therefore, there remains a need for compositions and methods to effectively and safely prevent or treat RSV infection.

Thus, the invention provides such compositions and methods for effectively and safely preventing or treating RSV infection in a mammal, preferably a human.

SUMMARY

In accordance with the purpose(s) of this invention, as embodied and broadly described herein, this invention, in one aspect, relates to a viral expression vector comprising a parainfluenza virus 5 (PIV5) genome having a heterologous nucleic acid sequence with at least 95% sequence identity to SEQ ID NO: 1, wherein the viral expression vector expresses a heterologous polypeptide comprising a live recombinant canine parainfluenza (CPI) vector backbone engineered to express a RSV F protein as target antigen. In one embodiment, the RSV F protein is encoded by a wildtype or mutated RSV F protein gene. In another embodiment, the RSV F protein gene is codon optimized for expression in a human subject. In yet another embodiment, the RSV F protein gene is inserted between a SH and HN junction of a CPI antigenomic cDNA, wherein the CPI antigenomic cDNA is sequenced with primers having a nucleic acid sequence with at least 95% sequence identity to SEQ ID NO: 2, 3, 4, 5, 6, 7, 8, 9, 10, 11, 12, 13, 14, 15, 16, 17, 18, or 19. In another embodiment, the parainfluenza (CPI) vector backbone engineered to express a RSV F protein comprises a 22 amino acid extension as part of its cytoplasmic tail.

In another aspect, the invention relates to a pharmaceutical composition comprising a parainfluenza virus 5 (PIV5) viral expression vector having a heterologous nucleic acid sequence with at least 95% sequence identity to SEQ ID NO: 1, wherein the viral expression vector expresses a heterologous polypeptide comprising a live recombinant canine parainfluenza (CPI) vector backbone engineered to express a RSV F protein as a target antigen. In one embodiment, the RSV F protein is encoded by a wildtype or mutated RSV F protein gene, wherein the RSV F protein gene is codon optimized for expression in a human subject. In another embodiment, the RSV F protein gene is inserted between a SH and HN junction of a CPI antigenomic cDNA, wherein the CPI antigenomic cDNA is sequenced with primers having a nucleic acid sequence with at least 95% sequence identity to 2, 3, 4, 5, 6, 7, 8, 9, 10, 11, 12, 13, 14, 15, 16, 17, 18, or 19. In yet another embodiment, the parainfluenza (CPI) vector backbone engineered to express the RSV F protein comprises a 22 amino acid extension as part of its cytoplasmic tail. In one other embodiment, the live recombinant canine parainfluenza (CPI) vector backbone engineered to express a RSV F protein is a prophylactic vaccine against RSV infection.

In yet another aspect, the invention relates to a method of inducing an immune response in a subject having RSV comprising administering a prophylactic vaccine against RSV infection, wherein the vaccine comprises a live recombinant canine parainfluenza (CPI) vector backbone engineered to express a RSV F protein as described above. In another embodiment, the vaccine induces RSV F-protein specific serum antibodies and cell mediated responses. In another embodiment, the RSV-F specific serum antibodies and cell mediated responses are associated with a reduced incidence of an RSV-induced pathological lung response compared to an immune response obtained by administering a formalin-inactivated RSV (FI-RSV). In one other embodiment, the pathological lung response is selected from a group consisting of: peribronchiolitis, perivasculitis, interstitial pneumonia, and alveolitis. In another embodiment, the vaccine is administered intranasally, intramuscularly, topically, or orally. In another embodiment, the vaccine is administered in a single or multiple dose regimen.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIGS. 17A-17B show RSV neutralizing Abs by microneutralization assay; FIGS. 17C-17D show F-specific RSV IgA Abs and FIGS. 17E-17F show F-specific IgG Abs by ELISA. Individual log 2 titers, and mean log 2 titers with the respective standard deviations (error bars) at Days 1, 15 and 29 by age group are shown in the graphs in the left column, and geometric mean fold rises from baseline (GMFRs) on Day 15 and Day 29 by age group are shown in the graphs in the right column. * P<. 05;  P<01; * $P<0.001$ by Wilcoxon test.

FIGS. 19A-19B show PIV5 neutralizing Abs by microneutralization assay; and FIGS. 19C-19D show PIV5-specific RSV IgG Abs by ELISA. Individual $\log_2$ titers, and mean $\log_2$ titers with the respective standard deviations (error bars) at Days 1, 15 and 29 by age group are shown in the graphs in the left column, and geometric mean fold rises from baseline (GMFRs) on Day 15 and Day 29 by age group are shown in the graphs in the right column. * P<. 05;  P<. 01; * $P<0.001$ by Wilcoxon test.

FIG. 20C shows percentage of subjects with nasal F-specific IgA responses to the PIV5-RSV vaccine (≥2-fold rise in titer) by subgroups based on individual baseline nasal F-specific IgA titer being below (L) or above (H) the baseline geometric mean titer for nasal F-specific IgA for each age group (Group 1 and Group 2).

FIGS. 22E & 22F show mean percentages of $CD4^+$ T cells (left graphs) and $CD8^+$ T cells (right graphs) by age group on Days 1, 15 and 29 by expression of the indicated Th1/cytotoxic marker combinations (IFN-γ, TNF-α, CD107a) represented in stacked histograms. FIGS. 22G & 22H show geometric mean fold rises from baseline (GMFRs) on Day 15 and Day 29 by age group for $CD4^+$ and $CD8^+$ T cells. FIGS. 22G and 22H show fold change of CD4 and CD8 T cell responses at Days 15 and 29 postvaccination. FIGS. 22I & 22J are pie-chart representations of the proportions of F-specific $CD4^+$ and $CD8^+$ T cells expressing 1, 2 or 3 Th1/cytotoxic markers (IFN-γ, TNF-α, CD107a) at Days 15 and 29 in Groups 1 and 2. * P<. 05;  P<. 01; * $P<0.001$, ns: not significant.

DETAILED DESCRIPTION

Figure 1A:
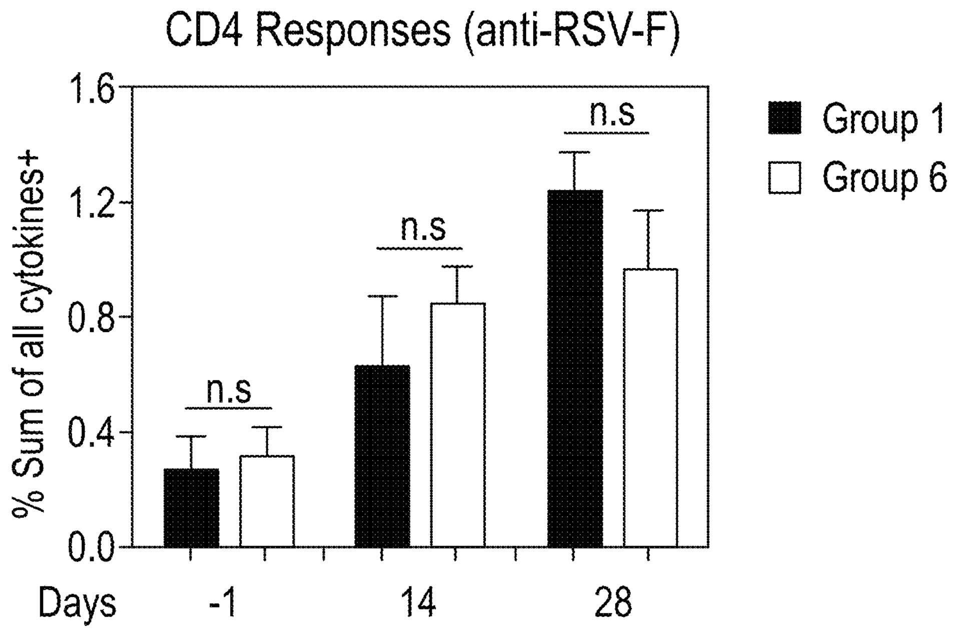
FIGS. 1A-1B show RSV F-specific immune responses in immunized AGMs. RSV F-specific cellular immune response in immunized African green monkeys (AGMs). PBMCs were isolated from immunized AGMs one day prior to vaccination, and at 14 and 28 days post-immunization. The PBMCs were stimulated with an RSV F peptide pool, and different cytokine levels in $CD4^+$ (FIG. 1A) and $CD8^+$ (FIG. 1B) cells were quantified by ICS and expressed at % sum of all cytokines. Group 1=control, Group 6=CPI-RSV-F.

The present invention may be understood more readily by reference to the following detailed description of preferred embodiments of the invention and the Examples included therein and to the Figures and their previous and following description.

I. Definitions

To facilitate an understanding of the principles and features of the various embodiments of the disclosure, various illustrative embodiments are explained herein. Although exemplary embodiments of the disclosure are explained in detail, it is to be understood that other embodiments are contemplated. Accordingly, it is not intended that the disclosure is limited in its scope to the details of construction and arrangement of components set forth in the description or examples. The disclosure is capable of other embodiments and of being practiced or carried out in various ways.

In describing the exemplary embodiments, specific terminology will be resorted to for the sake of clarity. As used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

For any method disclosed herein that includes discrete steps, the steps may be conducted in any feasible order. And, as appropriate, any combination of two or more steps may be conducted simultaneously.

The description exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

Similarly, as used herein, "substantially free" of something, or "substantially pure", and like characterizations, can include both being "at least substantially free" of something, or "at least substantially pure", and being "completely free" of something, or "completely pure."

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

As described herein, the term "vaccinating" designates typically the sequential administration of one or more antigens to a subject, to produce and/or enhance an immune response against the antigen(s). The sequential administration includes a priming immunization followed by one or several boosting immunizations.

Within the context of the present invention, the term "pathogen" refers to any agent that can cause a pathological condition. Examples of "pathogens" include, without limitation, cells (e.g., bacteria cells, diseased mammal cells, cancer mammal cells), fungus, parasites, viruses, prions or toxins. Preferred pathogens are infectious pathogens. In a particular embodiment, the infectious pathogen is a virus, such as the coronaviruses.

An antigen, as used therein, designates any molecule which can cause a T-cell or B-cell immune response in a subject. An antigen specific for a pathogen is, typically, an element obtained or derived from said pathogen, which contains an epitope, and which can cause an immune response against the pathogen. Depending on the pathogenic agent, the antigen may be of various nature, such as a (poly) peptide, protein, nucleic acid, lipid, cell, etc. Live weakened forms of pathogens (e.g., bacteria, viruses), or killed or inactivated forms thereof may be used as well, or purified material therefrom such as proteins, peptides, lipids, etc. The antigen may be naturally-occurring or artificially created. It may be exogenous to the treated mammal, or endogenous (e.g., tumor antigens). The antigen may be produced by techniques known per se in the art, such as for instance synthetic or recombinant technologies, or enzymatic approaches.

In a particular embodiment, the antigen is a protein, polypeptide and/or peptide. The terms "polypeptide", "peptide" and "protein" are used interchangeably herein to refer to a polymer of amino acid residues. The terms also apply to amino acid polymers in which one or more amino acid residues may be modified or non-naturally occurring residues, such as an artificial chemical mimetic of a corresponding naturally occurring amino acid. It should be understood that the term "protein" also includes fragments or variants of different antigens, such as epitope-containing fragments, or proteins obtained from a pathogen and subsequently enzymatically, chemically, mechanically or thermally modified.

A "therapeutically effective amount" means the amount of a compound (e.g., a PIV5-based composition as described herein) that, when administered to a subject for treating a state, disorder or condition, is sufficient to effect such treatment. The "therapeutically effective amount" will vary depending on the compound or bacteria administered as well as the disease and its severity and the age, weight, physical condition and responsiveness of the mammal to be treated.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "pharmaceutically acceptable composition" as used herein refers to a composition comprising at least one compound as disclosed herein formulated together with one or more pharmaceutically acceptable carriers.

The term "administration" refers to the introduction of an amount of a predetermined substance into a patient by a certain suitable method. The composition disclosed herein may be administered via any of the common routes, as long as it is able to reach a desired tissue, for example, but is not limited to, inhaling, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

The term "dose" means a single amount of a compound or an agent that is being administered thereto; and/or "regimen: which means a plurality of pre-determined doses that can be different in amounts or similar, given at various time intervals, which can be different or similar in terms of duration. In some embodiments, a regimen also encompasses a time of a delivery period (e.g., agent administration period, or treatment period). Alternatively, a regimen is a plurality of predetermined plurality pre-determined vaporized amounts given at pre-determined time intervals.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

Within the context of the present invention, the term "pathogen" refers to any agent that can cause a pathological condition. Examples of "pathogens" include, without limitation, cells (e.g., bacteria cells, diseased mammal cells, cancer mammal cells), fungus, parasites, viruses, prions or toxins. Preferred pathogens are infectious pathogens. In a particular embodiment, the infectious pathogen is a virus, such as the coronaviruses.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

As used herein, the term "parainfluenza virus 5" (PIV5) includes, for example and not limitation, strains KNU-11, CC-14, D277, 1168-1, and 08-1990. Non-limiting examples of PIV5 genomes are listed in GenBank® nucleotide sequence database under Accession Nos. NC_006430.1, AF052755.1, KC852177.1, KP893891.1, KC237065.1, KC237064.1 and KC237063.1, which are hereby incorporated by reference.

As used herein, the term "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA. In the context of the present invention, the term also encompasses the yield of RSV F gene mRNA and RSV F proteins achieved following expression thereof.

As used herein, the term "F protein" or "Fusion protein" or "F protein polypeptide" or "Fusion protein polypeptide" refers to a polypeptide or protein having all or part of an amino acid sequence of an RSV Fusion protein polypeptide. Numerous RSV Fusion and Attachment proteins have been described and are known to those of skill in the art. WO/2008/114149, which is herein incorporated by reference in its entirety, sets out exemplary F and G protein variants (for example, naturally occurring variants).

The materials described as making up the various elements of the disclosure are intended to be illustrative and not restrictive. Many suitable materials that would perform the same or a similar function as the materials described herein are intended to be embraced within the scope of the disclosure. Such other materials not described herein can include, but are not limited to, for example, materials that are developed after the time of the development of the disclosure.

II. CPI-RSV-F Compositions

Respiratory syncytial virus (RSV) is a member of the genus Pneumovirus of the family Paramyxoviridae. Human RSV (HRSV) is the leading cause of severe lower respiratory tract disease in young children and is responsible for considerable morbidity and mortality in humans. RSV is also recognized as an important agent of disease in immunocompromised adults and in the elderly. Due to incomplete protection to RSV in the infected host after a natural infection, RSV may infect multiple times during childhood and adult life.

This virus has a genome comprised of a single strand negative-sense RNA, which is tightly associated with viral protein to form the nucleocapsid. The viral envelope is composed of a plasma membrane derived lipid bilayer that contains virally encoded structural proteins. A viral polymerase is packaged with the virion and transcribes genomic RNA into mRNA. The RSV genome encodes three transmembrane structural proteins, F, G, and SH, two matrix proteins, M and M2, three nucleocapsid proteins N, P, and L, and two nonstructural proteins, NS1 and NS2.

Fusion of HRSV with infected cell membranes is thought to occur at the cell surface and is a necessary step for the transfer of viral ribonucleoprotein into the cell cytoplasm during the early stages of infection. This process is mediated by the fusion (F) protein, which also promotes fusion of the membrane of infected cells with that of adjacent cells to form a characteristic syncytia, which is both a prominent cytopathic effect and an additional mechanism of viral spread. Accordingly, neutralization of fusion activity is important to block virus infection and is important in host immunity. Indeed, monoclonal antibodies developed against the F protein have been shown to neutralize virus infectivity and inhibit membrane fusion (Calder et al., 2000, *Virology* 271:122-131).

The F protein of RSV shares structural features and limited, but significant amino acid sequence identity with F glycoproteins of other paramyxoviruses. It is synthesized as an inactive precursor of 574 amino acids (F0) that is cotranslationally glycosylated on asparagines in the endoplasmic reticulum, where it assembles into homo-oligomers. Before reaching the cell surface, the F0 precursor is cleaved by a protease into F2 from the N terminus and F1 from the C terminus. The F2 and F1 chains remain covalently linked by one or more disulfide bonds.

CPI-RSV-F is a parainfluenza virus (PIV5) based RSV vaccine expressing the RSV F protein, is provided herein as prophylactic intranasal vaccines to prevent RSV infection and serious complications associated with RSV infection. CPI-RSV-F was designed to induce immune responses to the F protein of RSV, which is the main antigenic protein that is highly conserved between the RSV subgroups A and B. Anti-F antibodies inhibit virus entry into host cells and RSV F is a proven vaccine target based on the efficacy data from the commercial product palivizumab (RSV F monoclonal antibody).

The disclosure provides CPI-RSV-F compositions, systems and methods for their use in multiple applications including functional genomics, drug discovery, target validation, protein production (e.g., therapeutic proteins, vaccines, monoclonal antibodies), gene therapy, and therapeutic treatments such as cancer therapy.

A. Pharmacology Summary of RSV Studies

The disclosure provides CPI-RSV-F compositions, systems and methods for their use in multiple applications including functional genomics, drug discovery, target validation, protein production (e.g., therapeutic proteins, vaccines, monoclonal antibodies), gene therapy, and therapeutic treatments such as cancer therapy.

Previously published studies based on W3A strain of PIV5 construct engineered to express RSV-F protein included immunogenicity and challenge studies in mice, cotton rats and African green monkeys (1,2,3). As part of these studies, permissiveness for PIV5 replication was confirmed in cotton rats and African monkeys (1, 2). In addition, the following studies were performed: 1) compared vector constructs based on CPI vs. W3A PIV5 strain; 2) compared vaccine constructs expressing RSV pre-fusion versus wt F-protein in place of PIV5 SH gene (ΔSH) or inserted between PIV5 SH and NH (SH-NH) or between HN and L (HN-L). These studies led to the selection of CPI-RSV-F (CPI-RSV-F), containing the full length of RSV F-protein inserted between SH and HN gene (FIG. 1) for use in the initial human studies.

In addition, the protective efficacy of CPI-RSV-F vaccine has been evaluated in RSV challenge studies conducted in mice and cotton rats. Immunization with a single intranasal dose protected animals from RSV infection based on significantly reduced RSV viral titers observed in lung and nasal washes of immunized animals compared to controls.

More recent preclinical proof of concept studies conducted with the vaccine vector construct CPI-RSV-F included immunogenicity and challenge studies conducted by Blue Lake Biotechnology Inc. in mice and African green monkeys. In addition, preclinical data from a NIH sponsored study of the CPI-RSV-F construct in a cotton rat challenge study are summarized for which Blue Lake Biotechnology Inc. provided the vaccine product. The CPI-RSV-F vaccine used in these more recent non-clinical studies used a prior vaccine vector construct (rescued from BHK cells) that is the same as the vector construct used for clinical trial material (rescued from 293/Vero cells), and similarly produced using serum-free Vero cells as the substrate and formulated with sucrose phosphate glutamate (SPG) buffer. These non-clinical studies included W3AΔSH-RSV-F (PIV5 W3A strain engineered to express RSV F protein) as an active comparator.

Phase 1 clinical trial of CIP-RSV-F demonstrated RSV vaccine safety in young adults (Group 1) and older adults (Group 2). The vaccine elicited serum RSV-specific and nasal IgA antibody responses as well as potent cellular immune Reponses (Spearman et al., *Sci. Adv.* 9, eadj7611 (2023)).

In summary, the non-clinical studies in various animal models have demonstrated the ability of CPI-RSV-F to induce RSV F specific immune responses, as observed by F-specific antibody and cell mediated responses following a single intranasal dose. CPI-RSV-F was well tolerated in these animal models and no indication of sensitization following vaccination with CPI-RSV-F was observed. Recent non-clinical studies conducted in mice, cotton rats and African green monkeys with the CPI-RSV-F vaccine construct (vaccine based on CPI PIV5 strain) are summarized below. These studies included an active comparator (vaccine vector based on PIV5 W3A strain) with RSV F protein replacing SH gene (ΔSH). See FIG. 1 for further detail on vaccine vector constructs. For an overview of non-clinical studies conducted with various vaccine vector constructs, see Table 1.

TABLE 1

Non-clinical study overview of prior vaccine constructs studies and recent studies with CPI-RSV-F construct.

| Study type | Species | Vaccine vector | Vaccine route | Reference report |
|---|---|---|---|---|
| Immunogenicity/ challenge study | Mice | W3A strain with wt RSV F protein inserted into PIV5 HN-L region | i.n. | Phan et al. 2014 |
| Immunogenicity/ challenge/ safety study | Mice and Cotton rats | W3A strain with wt RSV or prefusion RSV F protein inserted at deleted SH region or between SH and HN | i.n. and s.c. | Phan et al 2017/ Sigmovir Protocol #XV-131 Study report |
| Immunogenicity/ challenge/ safety study | Cotton rats and African Green monkeys | W3A strain with RSV F protein inserted into the intergenic regions of PIV5 HN and L | i.n | Wang et al 2017 |
| Recent studies with control (construct to be used in clinical study and used in toxicology study) | | | | |
| Immunogenicity/ challenge study | Mice | CPI strain with RSV F protein between SH and HN or replacing HN (CPI-RSV- | i.n. | Report 1 |

TABLE 1-continued

Non-clinical study overview of prior vaccine constructs studies and recent studies with CPI-RSV-F construct.

| Study type | Species | Vaccine vector | Vaccine route | Reference report |
|---|---|---|---|---|
| | | F, CPIΔSH-RSV-F) or controls W3A-RSV-F and W3AΔSH-RSV-F construct rescued from BHK cells | | |
| Immunogenicity study | African green Monkeys | CPI strain with RSV F protein between SH and NH (CPI-RSV-F) or control W3AΔSH-RSV-F construct rescued from BHK cells | i.n. | No report. |
| Immunogenicity/ challenge/ safety study | Cotton rats | CPI strain with RSV F protein between SH and NH (CPI-RSV-F, CPI-RSV-F) or control W3AΔSH-RSV-F Construct rescued from BHK cells | | Sigmovir Study XV-238 report (NIH sponsored) |

i. Studies in Mice, Cotton Rats, and Monkeys with Related W3A PIV5 Vector Expressing RSV F Protein PIV5 (W3A)-RSV-F and RSV-G protein study in Balb/c mice (3, Phan et al. 2014): In this study Balb/c mice received a single intranasal dose of PIV5-RSV-F ($10^6$ PFU dose in 50 μl) followed by RSV challenge. The PIV5 W3A vaccine vector construct in this study consisted of wild type RSV F protein inserted into the PIV5 HN and L intergenic regions. A single intranasal dose resulted in IgG2a/IgG1 RSV responses similar to that observed after wild-type RSV A2 infection at Day 21 after immunization.

PIV5 (W3A) expressing wild-type or Prefusion RSV F protein challenge study in mice and cotton rats (1, Phan et al 2017): This study evaluated PIV5 vectored vaccines that were improved by changing location of F-protein insertion (inserted at SH-HN junction of PIV5 or replacing the SH with the RSV F protein gene). In addition, this study evaluated both the wild type (wt) F-protein or a prefusion conformation F-protein (pF).

Mice were immunized intranasally with single dose of W3AΔSH-RSV-F (RSV F protein gene inserted at deleted SH region of PIV5) expression wild type F protein or prefusion stabilized RSV F mutant (W3AΔSH-RSV-pF) or improved vector W3A-RSV-F SH-HN or W3A-RSV-pF SH-HN (the F-protein gene inserted at the SH-HN junction) at $1\times10^6$ PFU. The study groups were as follows (Table 2).

TABLE 2

Study groups in mice challenge study

| Vaccine/route | Number of animals | Challenge virus |
|---|---|---|
| PBS | 10 | $1\times10^6$ PFU RSV A/A2 |
| RSV A2 | 5 | $1\times10^6$ PFU RSV A/A2 |
| W3A(HN-L)-RSV-F, $10^6$ PFU, i.n. | 10 | $1\times10^6$ PFU RSV A/A2 |
| W3A(SH-HN)-RSV-F,, $10^6$ PFU, i.n. | 10 | $1\times10^6$ PFU RSV A/A2 |
| W3A(SH-HN)-RSV-pF, $10^6$ PFU, i.n. | 10 | $1\times10^6$ PFU RSV A/A2 |
| W3AΔSH-RSV-F, $10^6$ PFU, i.n. | 10 | $1\times10^6$ PFU RSV A/A2 |
| W3AΔSH-RSV-PF, $10^6$ PFU, i.n. | 10 | $1\times10^6$ PFU RSV A/A2 |

Following immunization, both humoral and cell mediated immune responses were observed. The highest neutralizing antibody responses were detected with vaccine construct using the wt F protein. Also, vaccine constructs containing the wt F inserted prior to the HN junction with ΔSH seemed to be most immunogenic. The level of cell-mediated immune responses (based on IFN-gamma using ELISPOT) was similar between the various vaccine constructs.

Mice were challenged 28 days after immunization with RSV A2 to determine protective efficacy. Challenge virus was only obtained from one of five mice at day 4 post challenge in the W3AΔSH-RSV-F group with none of the mice in the other vaccination groups. In the PBS control group challenge virus was recovered from all mice.

A similar study was conducted in cotton rats which are more permissive to RSV infection. Rats were immunized with low dose of $10^3$ PFU of the modified vectors (W3A-RSV-F (SH-HN), W3A-RSV-pF, W3AΔSH-RSV-F) containing wild type or perfusion stabilized F-protein (pF) or $10^2$ PFU of W3AΔSH-RSV-pF.

Immune responses were observed in all groups including neutralizing antibody responses against RSV A Tracy strain (97% identical to RSV A/A2 strain). Similar to the mouse study, the groups immunized with vaccine constructs containing the wt F protein had higher antibody levels compared to the pF groups, with F insertion prior to the HN gene junction with ΔSH having the highest values (approx. titer of 128). The neutralization antibody titers to RSV/B/18537 were significantly lower than to RSV/A Tracy strain, only the W3A (SH-HN)-RSV-F and W3AΔSH-RSV-F groups had significant antibody levels (approx. titer of 8) detected. After RSV challenge on Day 28 with $1.21\times10^5$ PFU of RSV/A/Tracy, reduction in RSV viral load in nasal washes (1.4-1.66 $Log_{10}$ reduction) and lung lavage fluid (2-3 $Log_{10}$ reduction) was observed for all vaccine dose groups. The RSV challenge virus was recovered from all mice in the PBS control group (approx. $10^5$ PFU per nasal wash, or $10^5$ PFU/g lung wash).

Overall, these initial studies in the mouse and cotton rat models did not show evidence of the prefusion F-protein being more immunogenic and protective then the wild type F protein. Also, no difference was observed in the vector performance between ΔSH and the SH-HN insertion vector construct for the intranasal route.

Sigmovir Protocol #XV-131 Study report (Phan et al. 2017) challenge studies in cotton rat using intranasal and subcutaneous route: In a follow-on study (1, Phan et al. 2017) the efficacy, immunogenicity and safety of higher doses $10^5$ and $10^6$ PFU of W3A (SH-NH)-RSV-F and control were tested in a cotton rat challenge study evaluating two different routes intranasal (i.n.) and subcutaneous (s.c). This study also included a positive control for enhancement of disease (animals immunized with FI-RSV followed by RSV challenge and a positive control group consisting of animals that were pre-infected with RSV followed by RSV challenge. Animals in this study were challenged with RSV A2 on Day 49 followed by necropsy and histology 5 days later (Day 54). The study groups in this study were as follows (Table 3).

TABLE 3

Study groups in Protocol #XV-131.

| Vaccine/route | N = number of animals | RSV/A2 Challenge |
|---|---|---|
| PBS i.m. | 5 | PBS |
| PBS i.m | 5 | $5Log_{10}$ PFU |
| FI-RSV i.m | 5 | $5Log_{10}$ PFU |
| RSV/A2 Live, i.n. (positive control) | 5 | $5Log_{10}$ PFU |
| W3A(SH-HN)-RSV-F, $10^5$ PFU i.n. | 5 | $5Log_{10}$ PFU |
| W3A(SH-HN)-RSV-F, $10^5$ PFU s.c | 5 | $5Log_{10}$ PFU |
| W3A(SH-HN)-RSV-F, $10^6$ PFU s.c | 5 | $5Log_{10}$ PFU |
| W3AΔSH-RSV-F, $10^5$ PFU i.n. | 5 | $5Log_{10}$ PFU |
| W3AΔSH-RSV-F, $10^5$ PFU s.c. | 5 | $5Log_{10}$ PFU |
| W3AΔSH-RSV-F, $10^6$ s.c. | 5 | $5Log_{10}$ PFU |

Immunogenicity: W3A (SH-HN)-RSV-F resulted in similar neutralizing antibody titer in $10^5$ and $10^6$ dose between i.n and s.c group. W3AΔSH-RSV-F vaccination induced slightly higher neutralizing antibody titers in i.n group compared to s.c group, with $10^6$ dose resulting in a slightly higher titer, although it was not statistically significant.

Efficacy: W3A (SH-HN)-RSV-F resulted in complete protection in the lower respiratory tract by either i.n or s.c administration. Animals also had significantly lower viral loads in the upper respiratory tract.

W3A (SH-HN)-RSV-F vaccination resulted in complete protection in the lower respiratory tract by s.c administration and almost complete protection by i.n administration based on reduced titers (average titer of $10^3$ PFU) observed in lung and nasal washes compared to control animals sham immunized with PBS (average titer of $10^5$ PFU).

Safety: Lung sections from the different groups were examined for hallmarks of pulmonary inflammation: peribronchiolitis, perivasculitis, interstitial pneumonia, and alveolitis and scored for severity. The largest lesions were observed in the FI-RSV-immunized, RSV-challenged group (positive control group). Pulmonary changes were moderate in the groups immunized with W3A-RSV-F (SH-HN) or W3AΔSH-RSV-F (intranasally or subcutaneously), with levels below those observed in the RSV-immunized, RSV-challenged positive control group and similar to those in the PBS sham-immunized, RSV-challenged group.

Cytokine levels measured in lung tissues at 5 days post-challenge by quantitative real-time PCR (qPCR) were not indicative of potential of enhanced infection. The IL-4 mRNA level was significantly elevated only in the FI-RSV-vaccinated group, consistent with the histopathology results and the enhanced disease phenotype. IFNγ-mRNA levels were the highest in the sham-immunized and FI-RSV-immunized groups. IFN-mRNA levels were similarly low between groups immunized with the PIV5-based candidates and the RSV-immunized group. IL-2 mRNA levels were similar in all groups, but the average IL-2 level in the FI-RSV immunized group was significantly higher than that in the other groups.

After intranasal challenge of immunized mice with RSV A2 ($10^6$ PFU in 50 μl) at Day 28 after immunization, lung sections obtained at 4 days after challenge showed no exacerbation of lung lesions relative to RSV-A2 immunized mice. Protective immunity was observed as assessed by viral load in lung tissues (n=5 mice per group).

PIV5 (W3A) expressing RSV F or G protein challenge study in cotton rats and African green monkeys (2, Wang et al 2017): This study evaluated PIV5 vectored RSV F protein in cotton rats and African green monkeys for replication, immunogenicity and efficacy of protection against RSV challenge. In this study, the F protein was inserted into the intergenic regions of PIV5 HN and L gene.

PIV5 replication permissiveness in cotton rats and African green monkeys: Cotton rats (n=4 per group) were inoculated intranasally with $1\times10^5$ PFU of PIV5 at volumes of 10 μl or 100 μl. Viral titers were observed in nose homogenates (up $1\times10^4$ PFU) at day 4 which cleared mostly by day 6. The larger inoculum volume (100 μl) resulted in observation of vaccine virus in the lungs of all the animals at day 6, which was only observed for one animal inoculated with the smaller volume of 10 μl.

To evaluate PIV5 permissiveness in African green monkeys, 60 animals were screened for anti-PIV5 antibodies and all were found to be negative. Animals (n=3 per group) were infected intranasally with $1\times10^2$ up to $1\times10^8$ PFU of PIV5 in 0.25 mL dose volume. Nasal wash and bronchoalveolar washes were assessed for virus shedding on days 3, 5, 7, 10 and 14. Virus was shed from both nose and lungs for up to 10-day period with peak replication at Day 5 for the dose as low as $1\times10^2$ PFU. This data demonstrates permissiveness of African green monkeys for PIV5.

Immunogenicity in cotton rats and African green monkeys after single dose control: Cotton rats were immunized intranasally with $1\times10^3$, $1\times10^4$, $1\times10^5$ and $1\times10^6$ PFU of W3A-RSV-F (SH-HN). At all dose levels, IgG antibody responses were noted at Day 28 with comparable responses per dose group. Neutralizing antibodies were observed in all dose group ranging from titer of 64 to 256 (NT50%). In addition, IgA responses in lung homogenates were observed in all dose groups at Day 21 post inoculation.

African green monkeys (PIV5 and RSV serum negative) received a single intranasal immunization with $1\times10^4$ or $1\times10^6$ PFU W3A-RSV-F (SH-HN). Sera obtained at Day 21 post inoculation showed high titers of F-specific antibody responses. In addition, neutralizing antibody responses were observed at Day 21 at low levels (NT50%, 52 in $1\times10^6$ PFU dose group). Nasal swabs obtained at 21 days post immunization showed significant levels of F-protein IgA responses. Cell mediated responses as assessed by gamma interferon showed low level responses in the $1\times10^6$ PFU dose group.

Protection in cotton rats and African green monkeys from RSV challenge: Cotton rats immunized intranasally with single dose ranging from $1\times10^3$ to $1\times10^6$ PFU W3A-RSV-F (SH-HN) were challenged with RSV A2 strain at Day 28 after immunization. Protection was assessed by measuring of viral loads in nose and lung tissues. Reduced viral loads were observed in a dose-dependent manner except for the $1\times10^6$ PFU group which showed higher levels relative to $1\times10^3$ PFU group but still reduced compared to control group. In the $1\times10^5$ dose group, no virus was detected in the lung and reduced titers (order of 3 log 10) were observed in the nose.

African green monkeys immunized with $1\times10^4$ or $1\times10^6$ PFU W3A-RSV-F (SH-HN) were challenged 28 days after immunization with RSV A2. Nasal and BAL samples were assessed for RSV viral load Day 3-14 after challenge. Immunization with control did not shorten virus shedding, however, peak viral RSV loads were reduced 10 to 100-fold in both dose groups, with the highest reduction observed in the $1\times10^6$ PFU dose group.

Responses to control in RSV exposed African green monkeys: Prior exposure to RSV did not interfere with ability to boost RSV neutralization antibody titers (50-fold increase) in African green monkeys (seroconverted by intranasal infection with RSV A2).

Lung pathology in W3A-RSV-F (SH-HN) immunized cotton rats after RSV challenge: In animals immunized at Day 0 with dose $1\times10^6$ PFU W3A-RSV-F and challenged at Day 49 with RSV A2, lungs obtained five days after challenge were blindly examined by histopathology for alveolitis, interstitial pneumonitis, perivasculitis, and peribronchiolitis and compared to lungs obtained from control animals inoculated with Formalin-inactivated RSV. The scores of positive control animals inoculated with formalin-inactivated RSV were significantly higher than PBS control animals but not the scores of W3A-RSV-F (SH-HN) animals (ANOVA paired t-test).

B. Parainfluenza Virus 5 (PIV5)

Parainfluenza virus 5 (PIV5), a negative-stranded RNA virus, is a member of the Rubulavirus genus of the family Paramyxoviridae which includes many important human and animal pathogens such as mumps virus, human parainfluenza virus type 2 and type 4, Newcastle disease virus, Sendai virus, HPIV3, measles virus, canine distemper virus, rinderpest virus and respiratory syncytial virus. PIV5 was previously known as Simian Virus-5 (SV5). Although PIV5 is a virus that infects many animals and humans, no known symptoms or diseases in humans have been associated with PIV5. Unlike most paramyxoviruses, PIV5 infect normal cells with little cytopathic effect. As a negative stranded RNA virus, the genome of PIV5 is very stable. As PIV5 does not have a DNA phase in its life cycle and it replicates solely in cytoplasm, PIV5 is unable to integrate into the host genome. Therefore, using PIV5 as a vector avoids possible unintended consequences from genetic modifications of host cell DNAs. PIV5 can grow to high titers in cells, including Vero cells which have been approved for vaccine production by WHO and FDA. Thus, PIV5 presents many advantages as a vaccine vector.

A PIV5-based vaccine vector of the present invention may be based on any of a variety of wild type, mutant, or recombinant (rPIV5) strains. Wild type strains include, but are not limited to, the PIV5 strains W3A, WR (ATCC® Number VR-288TM), canine parainfluenza virus strain 78-238 (ATCC number VR-1573) (Evermann et al., 1980, J Am Vet Med Assoc; 177:1132-1134; and Evermann et al., 1981, Arch Virol; 68:165-172), canine parainfluenza virus strain D008 (ATCC number VR-399) (Binn et al., 1967, Proc Soc Exp Biol Med; 126:140-145), MIL, DEN, LN, MEL, cryptovirus, CPI+, CPI−, H221, 78524, T1 and SER. See, for example, Chatziandreou et al., 2004, J Gen Virol; 85 (Pt 10): 3007-16; Choppin, 1964, Virology: 23:224-233; and Baumgartner et al., 1987, Intervirology; 27:218-223. Additionally, PIV5 strains used in commercial kennel cough vaccines, such as, for example, BI, FD, Merck, and Merial vaccines, may be used.

C. PIV5 CPI Strain Vector Backbone

The PIV5 CPI strain vector backbone differs from that of PIV5 W3A strain vector as follows: the most notable difference is in the PIV5 F protein of the CPI strain that consists of an additional 22 amino acid extension as part of its cytoplasmic tail. The extension of the F protein is thought to result in inhibition of the fusogenic properties of the virus (5,6). CPI based viruses are more lytic and produce more progeny virus in infected cells compared to the W3A based viruses that does not have the extended PIV5 F protein tail and possess additional amino acid difference compared with CPI (4).

i. PIV5 CPI Vectored RSV Constructs

A PIV5 vaccine vector of the present invention may be constructed using any of a variety of methods, including, but not limited to, the reverse genetics system described in more detail in He et al. (Virology; 237(2):249-60, 1997). PIV5 encodes eight viral proteins. Nucleocapsid protein (NP), phosphoprotein (P) and large RNA polymerase (L) protein are important for transcription and replication of the viral RNA genome. The V protein plays important roles in viral pathogenesis as well as viral RNA synthesis. The fusion (F) protein, a glycoprotein, mediates both cell-to-cell and virus-to-cell fusion in a pH-independent manner that is essential for virus entry into cells. The structures of the F protein have been determined and critical amino acid residues for efficient fusion have been identified. The hemagglutinin-neuraminidase (HN) glycoprotein is also involved in virus entry and release from the host cells. The matrix (M) protein plays an important role in virus assembly and budding. The hydrophobic (SH) protein is a 44-residue hydrophobic integral membrane protein and is oriented in membranes with its N terminus in the cytoplasm. For reviews of the molecular biology of paramyxoviruses see, for example, Whelan et al., 2004, Curr Top Microbiol Immunol; 283:61-119; and Lamb & Parks, (2006). Paramyxoviridae: the viruses and their replication. In Fields Virology, 5th edn, pp. 1449-1496. Edited by D. M. Knipe & P. M. Howley. Philadelphia, PA: Lippincott Williams & Wilkins.

Previously, recombinant PIV5 viruses expressing foreign genes from numerous pathogens, including Influenza, Rabies, Respiratory Syncytial Virus, Tuberculosis, *Burkholderia*, and MERS-COV have been generated and tested as vaccine candidates (Li, Z., et al., J Virol, 87(1):354 (2013); Chen, Z., et al., J Virol, 87(6):2986 (2013); Wang, D., et al., J Virol, 91(11) (2017); Chen, Z., et al., Vaccine, 33(51):7217 (2015); Lafontaine, E. R., et al., Vaccine X., 1:100002 (2018); Li, K., et al., mBio, 11(2) (2020)). Because it actively replicates in the respiratory tract following intranasal immunization, PIV5-vectored vaccines can generate mucosal immunity that includes antigen-specific IgA antibodies and long-lived IgA plasma cells (Wang, D., et al., J Virol, 91(11) (2017). Xiao, P., et al., Front Immunol,. 12:623996 (2021)).

Figure 7:
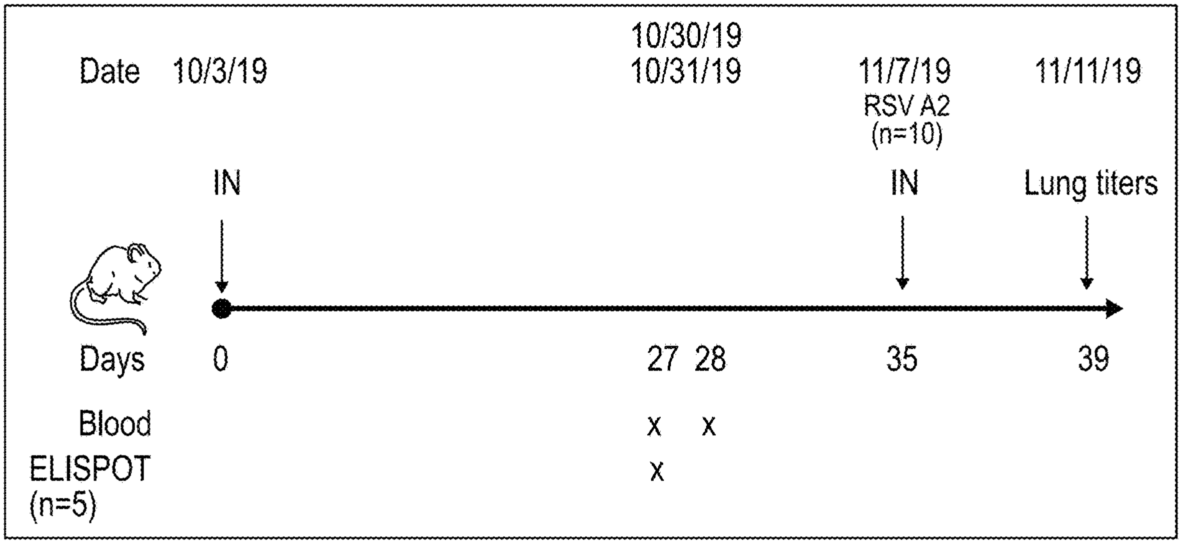
FIG. 7 shows an illustration of the CHD03 experimental timeline.

In one embodiment, The CPI-RSV-F vaccine drug substance (CPI-RSV-F) presented herein comprises a live recombinant PIV5 vectored virus based on the CPI strain of PIV5 expressing the wild type F-protein of RSV (F protein sequence based on GenBank Accession FJ614814J, SV A2 strain) codon-optimized for expression in human (FIG. 7). The wild type RSV F protein is inserted between the PIV5 SH and NH region (FIG. 1).

ii. Immunogenicity and Challenge Studies with CPI-RSV-F Vaccine Construct

In the non-clinical studies, a single dose of CPI-RSV-F was found to be immunogenic in mice, cotton rats, and AGMs following a single i.n. dose at dose levels ranging from $10^4$ to $10^6$ PFU. Both F-specific serum immune responses and cell-mediated responses were detected. The ability of the PIV5 vector to replicate in cotton rats and AGM was confirmed.

A single i.n. dose of CPI-RSV-F or related vaccine constructs was capable of protection from infection in various animal challenge models (mice, cotton rats and AGMs), using RSV A2 as challenge. Efficacy was based on reduced viral load observed in lung and nasal washes following challenge compared to viral load observed in control animals.

No observations of enhanced disease/lung pathology were observed in the cotton rat challenge model with CPI-RSV-F vector construct intended for use in the proposed Phase 1 study CPI-RSV-F. This conclusion was based on observed cytokine profile in lung tissue (no increase in IL-4 response) compared to positive control animals that had been vaccinated with formalin inactivated RSV (FI-RSV) and challenged with RSV. Similarly, no signs of enhanced disease/lung pathology were observed in the earlier published challenge studies in mice, cotton rats and AGM evaluating various W3A based vector constructs with F protein inserted at different locations within PIV5 W3A.

CPI-RSV-F was chosen over W3A for initial clinical evaluation given the similarity in being able to induce protective immune responses at similar dose levels as the W3A construct (albeit that immune responses to W3A appeared slightly higher). In addition, this same CPI PIV5 backbone engineered to express S-protein of SARS-COV-2 is also being evaluated clinically under IND 027418 which is being cross-referenced. Preclinical data and limited clinical data obtained to date with this related vector construct show a favorable safety profile when administered as a single intranasal dose at $10^6$ PFU to healthy adults 18-55.

III. BLB Genome Sequences

Provided herein are the CPI-RSV-F genomic sequences.

A. CPI-RSV-F Genomic Sequence i. CPI-RSV-F 5' to 3'

The CPI-RSV-F 5'-3' nucleic acid sequence is provided herein.

(SEQ ID NO: 1)

ACCAGGGGGAAAACGAAGTGGTGACTCAAATCATCGAAGACCCTCGAGATTACA

TAGGTCCGGAACCTATGGCCTTCGTGACCGACCTCGAGTCAGAGTAGTTCAATAA

GGACCTATCAAGTTTGGGCAATTTTTCGTCCCCGACACAAAAATGTCATCCGTGC

TTAAAGCATATGAGCGATTCACACTCACTCAAGAACTGCAAGATCAGAGTGAGG

AAGGTACAATCCCACCTACAACACTAAAACCGGTAATCAGGGTATTTATACTAAC

CTCTAATAACCCAGAGCTAAGATCCCGGCTTCTTCTATTTTGCCTACGGATTGTTC

TCAGTAATGGTGCAAGGGATTCCCATCGCTTTGGAGCATTACTTACAATGTTTTC

GCTACCATCAGCCACAATGCTCAATCATGTCAAATTAGCTGACCAGTCACCAGAA

GCTGATATCGAAAGGGTAGAGATCGATGGCTTTGAGGAGGGATCATTCCGCTTA

ATCCCCAATGCTCGTTCAGGTATGAGCCGTGGAGAGATCAATGCCTATGCTGCAC

TTGCAGAAGATCTACCTGACACACTAAACCATGCAACACCTTTTGTTGATTCCGA

AGTCGAGGGAACTGCATGGGATGAGATTGAGACTTTCTTAGATATGTGTTACAGT

GTCCTAATGCAGGCATGGATAGTGACTTGCAAGTGCATGACTGCGCCAGACCAA

CCTGCTGCTTCTATTGAGAAACGCCTGCAAAAATATCGTCAGCAAGGCAGGATCA

ACCCGAGATATCTCCTGCAACCGGAGGCTCGAAGAATAATCCAGAATGTAATCC

GAAAGGGAATGGTGGTCAGACATTTCCTCACCTTTGAACTGCAGCTTGCCCGAGC

ACAAAGCCTTGTATCAAATAGGTATTATGCTATGGTAGGGGATGTTGGAAAGTAT

ATAGAGAATTGTGGAATGGGAGGCTTCTTTTTGACACTAAAATATGCATTAGGAA

CCAGATGGCCCACACTTGCTTTAGCTGCATTTTCAGGAGAGCTAACAAAGCTAAA

GTCCCTCATGGCATTATACCAGACCCTTGGTGAGCAGGCCCGATATTTGGCCCTA

TTGGAGTCACCACATTTGATGGATTTTGCTGCAGCAAACTACCCACTGCTATATA

GCTATGCTATGGGAATAGGCTATGTGTTAGATGTCAACATGAGGAACTACGCTTT

CTCCAGATCATACATGAATAAGACATATTTCCAATTGGGAATGGAAACTGCAAG

AAAACAACAGGGTGCAGTTGACATGAGGATGGCAGAAGATCTCGGTCTAACTCA

AGCCGAACGCACCGAGATGGCAAATACACTTGCCAAATTGACCACAGCAAATCG

-continued

AGGGGCAGACACCAGGGGAGGAGTCAACCCGTTCTCATCTATCACTGGGACAAC

TCAGGTGCCCGCTGCAGCAACAGGTGACACATTCGAGAGTTACATGGCAGCGGA

TCGACTGAGGCAGAGATATGCTGATGCAGGCACCCACGATGATGAGATGCCACC

ATTGGAAGAGGAGGAAGAGGACGACACATCTGCAGGTCCACGCACTGGACTAAC

TCTTGAACAAGTGGCCTTGGACATCCAGAACGCAGCAGTTGGAGCTCCCATCCAT

ACAGATGACCTGAATGCCGCACTGGGTGATCTTGACATCTAGACAATTCAGATCC

CAATCTTAAATCGACACACCTAATTGACCAGTTAGATGGAACTACAGTGGATTCC

ATAAGGTTCCTGCCTACCATCGGCTTTTAAGAAAAAAATAGGCCCGGACGGGTTA

GCAACAAGCGACTGCCGATGCCAATAACACAATCCACAATCTACAATGGATCCC

ACTGATCTGAGCTTCTCCCCAGATGAGATCAATAAGCTCATAGAGACAGGCCTGA

ATACTGTGGAGTATTTTACTTCCCAACAAGTCACAGGAACATCCTCTCTTGGAAA

GAATACAATACCACCAGGGGTCACAGGACTACTAACCAATGCTGCAGAGGCAAA

GATCCAAGAGTCAACCAACCATCAGAAGGGTTCAGTTGGTGGGGGCGCAAAACC

AAAGAAACCGCGACCAAAAATTGCCATTGTGCCAGCAGATGACAAAACGGTGCC

CGGAAAGCCGATCCCAAACCCTCTATTAGGTCTGGACTCCACCCCGAGCACCCAA

ACTGTGCTTGATCTAAGTGGGAAAACATTACCATCAGGATCCTATAAGGGGGTTA

AACTTGCGAAATTTGGAAAAGAAAATCTGATGACACGGTTCATCGAGGAACCCA

GAGAGAATCCTATCGCAACCAATTCCCCCATCGATTTTAAGAGGGGCAGGGATA

CCGGCGGGTTCCATAGAAGGGAGTACTCAATCGGATGGGTGGGAGATGAAGTCA

AGGTCACTGAGTGGTGCAATCCATCCTGTTCTCCAATCACCGCTGCAGCAAGGCG

ATTTGAATGCACTTGTCACCAGTGTCCAGTCACTTGCTCTGAATGTGAACGAGAT

ACTTAATACAGTGAGAAATTTGGACTCTCGGATGAATCAACTGGAGACAAAAGT

AGATCGCATTCTCTCATCTCAGTCTCTAATCCAGACCATCAAGAATGACATAGTT

GGACTTAAAGCAGGGATGGCTACTTTAGAAGGAATGATTACAACTGTGAAAATC

ATGGACCCGGGAGTTCCCAGTAATGTTACTGTGGAAGATGTACGCAAGAAACTA

AGTAACCATGCTGTTGTTGTGCCAGAATCATTCAATGATAGTTTCTTGACTCAATC

TGAAGATGTAATTTCACTTGATGAGTTGGCTCGACCAACTGCAACAAGTGTTAAG

AAGATTGTCAGGAAGGTTCCTCCTCAGAAGGATCTGACTGGATTGAAGATCACA

CTAGAGCAATTGGCAAAGGATTGCATCAGCAAACCGAAGATGAGGGAAGAGTAT

CTCCTCAAAATCAACCAGGCTTCCAGTGAGGCTCAGCTAATTGACCTCAAGAAAG

CAATCATCCGCAGTGCAATTTGATCAAGAAACACCCAATTACACTACACTGGTAT

GACACTGTACTAACCCTGAGGGTTTTAGAAAAAACGATTAACGATAAATAAGCC

CGAACACTACACACCACCCGAGGCAGCCATGCCATCCATCAGCATCCCCGCAGA

CCCCACCAATCCACGTCAATCAATAAAAGCGTTCCCAATTGTGATCAACCGTGAT

GGGGGTGAGAAAGGTCGCTTGGTTAAACAACTACGCACAACCTACTTGAATGAC

CTAGATACTCATGAGCCACTGGTGACATTCGTAAATACTTATGGATTCATCTACG

AACAGGATCGGGGAAATACCATTGTCGGAGAGGATCAACATGGGAAGAAAAGA

GAGGCTGTGACTGCTGCAATGGTTACCCTTGGATGTGGGCCTAATCTACCATCAT

TAGGGAATGTCCTGGGACAACTGAGTGAATTCCAGGTCATTGTTAGGAAGACAT

CCAGCAAAGCGGAAGAGATGGTCTTTGAAATTGTTAAGTATCCGAGAATATTTCG

-continued

GGGTCATACATTAATCCAGAAAGGACTAGTCTGTGTCTCCGCAGAAAAATTTGTT

AAGTCACCAGGGAAAGTACAATCTGGAATGGACTATCTCTTCATTCCGACATTTC

TGTCAGTGACTTACTGTCCAGCTGCAATCAAATTTCAGGTACCTGGCCCCATGTT

GAAAATGAGATCAAGATACACTCAGAGCTTACAACTTGAACTAATGATAAGAAT

CCTGTGTAAGCCCGATTCGCCACTTATGAAGGTCCATATCCCTGACAAGGAAGGA

AGAGGATGTCTTGTATCAGTATGGTTGCATGTATGCAATATCTTCAAATCAGGAA

ACAAGAATGGCAGTGAGTGGCAGGAATACTGGATGAGAAAGTGTGCTAACATGC

AACTTGAAGTGTCGATTGCAGATATGTGGGGACCAACTATCATAATTCATGCCAG

AGGTCACATTCCCAAAAGTGCTAAGTTGTTTTTTGGAAAGGGTGGATGGAGCTGC

CATCCACTTCACGAAGTTGTTCCAAGTGTCACTAAAACACTATGGTCCGTGGGCT

GTGAGATTACAAAGGCGAAGGCAATAATACAAGAGAGTAGCATCTCTCTTCTCG

TGGAGACTACTGACATCATAAGTCCAAAAGTCAAAATTTCATCTAAGCATCGCCG

CTTTGGGAAATCAAATTGGGGTCTGTTCAAGAAAACCAAATCACTGCCCAACCTG

ACGGAGCTGGAATGACTGACCCCCAATCGAGACTACACCACCTCAAACTATAGG

TGGGTGGTACCTCAGTGATTAATCTCGTAAGCACTGATCGTAGGCTACAACACAC

TAATATTATCCAGATTAGAGAGCTTAATTAGCTCTGTATTAATAATAACACTACT

ATTCCAATAACTGGAATCACCAGCTTGATTTATCTCCAAAATGATTCAAAGAAAA

CAAATCATATTAAGACTATCCTAAGCACGAACCCATATCGTCCTTCAAATCATGG

GTACTATAATTCAATTTCTGGTGGTCTCCTGTCTATTGGCAGGAGCAGGCAGTCTT

GATCCAGCAGCCCTCATGCAAATCGGTGTCATTCCAACAAATGTCCGGCAACTTA

TGTATTATACTGAGGCCTCATCAGCATTCATTGTTGTGAAGTTAATGCCTACAATT

GACTCGCCGATTAGTGGATGTAATATAACATCAATTTCAAGCTATAATGCAACAG

TGACAAAACTCCTACAGCCGATCGGTGAGAATTTGGAGACGATTAGGAACCAGT

TGATTCCAACTCGGAGGAGACGCCGGTTTGCAGGGGTGGTGATTGGATTAGCTGC

ATTAGGAGTAGCTACTGCCGCACAGGTCACTGCCGCAGTAGCACTAGTAAAGGC

AAATGAAAATGCTGCGGCTATACTCAATCTCAAAAATGCAATCCAAAAAACAAA

TGCAGCAGTTGCAGATGTGGTCCAGGCCACACAATCACTAGGAACaGCAGTTCAA

GCAGTTCAAGATCACATAAACAGTGTGGTAAGTCCAGCAATTACAGCAGCCAAT

TGTAAAGCCCAAGATGCTATCATTGGCTCAATCCTCAATCTCTATTTGACCGAGT

TGACAACTATCTTCCACAATCAAATTACAAACCCTGCATTGAGTCCTATTACAAT

TCAAGCTTTAAGGATCCTACTAGGGAGTACCTTGCCGACTGTGGTCGAAAAATCT

TTCAATACCCAGATAAGTGCGGCTGAGCTTCTCTCATCAGGGTTATTGACAGGCC

AGATTGTGGGATTAGATTTGACCTATATGCAGATGGTCATAAAAATTGAGCTGCC

AACTTTAACTGTACAACCTGCAACCCAGATCATAGATCTGGCCACCATTTCTGCA

TTCATTAACAATCAAGAAGTCATGGCCCAATTACCAACACGTGTTATTGTGACTG

GCAGCTTGATCCAAGCCTATCCCGCATCGCAATGCACTATTACACCCAACACTGT

GTACTGTAGGTATAATGATGCCCAAGTACTCTCAGATGATACGATGGCTTGCCTC

CAAGGTAACTTGACAAGATGCACCTTCTCTCCAGTGGTTGGGAGCTTTCTCACTC

GATTCGTGCTGTTCGATGGAATAGTTTATGCAAATTGCAGGTCGATGTTGTGCAA

GTGCATGCAGCCTGCTGCTGTGATCCTACAGCCGAGTTCATCCCCTGTAACTGTC

ATTGACATGTACAAATGTGTGAGTCTGCAGCTTGACAATCTCAGATTCACCATCA

-continued

CTCAATTGGCCAATGTAACCTACAATAGCACCATCAAGCTTGAAACATCCCAGAT

CTTGCCTATTGATCCGTTGGATATATCCCAGAATCTAGCTGCGGTGAATAAGAGT

CTAAGTGATGCACTACAACACTTAGCACAAAGTGACACATACCTTTCTGCAATCA

CATCAGCTACGACTACAAGTGTATTATCCATAATAGCAATCTGTCTTGGATCGTT

AGGTTTAATATTAATAATCTTGCTCAGTGTAGTTGTGTGGAAGTTATTGACCATTG

TCGCTGCTAATCGAAATAGAATGGAGAATTTTGTTTATCATAATTCAGCATTCCA

CCACTCACGATCTGATCTCAGTGAGAAAAATCAACCTGCAACTCTTGGAACAAG

ATAAGACAGTCATCCATTAGTAATTTTTAAGAAAAAAACGATAGGACCGAAACT

AGTATTGAAAGAACCGTCTCGGTCAATCTAGGTAATCGAGCTGcTACCGTCTCGG

AAAGCTCAAATCATGCTGCCTGATCCGGAAGATCCGGAAAGCAAAAAAGCTACA

AGGAGAACAGGAAACCTAATTATCTGCTTCCTATTCATCTTCTTTCCGTTTGTAAA

CTTCATTGTTCCAACTCTAAGACACTTGCTGTCCTAACACCTGCTATAGGCTATCC

ACTGCATCATCTCTTTTTAAGAAAAAAATAGGCCCGGACGGGTTAGCAACAAGC

GACTGCCGGTGCCAACAACACAATCCACAATCTACAGTCGACGCGGCCGCCACC

ATGGAGCTGCTGATCCTGAAAGCCAACGCTATTACCACAATCCTGACCGCCGTGA

CATTCTGCTTTGCTTCCGGACAGAATATCACCGAGGAGTTCTACCAGTCAACATG

TAGCGCCGTGAGCAAGGGGTACCTGAGTGCACTGCGAACCGGATGGTATACATC

CGTGATTACTATCGAGCTGTCTAACATCAAGAAAAACAAATGCAATGGCACTGA

CGCCAAGATCAAGCTGATCAAGCAGGAGCTGGATAAGTACAAAAATGCTGTGAC

CGAACTGCAGCTGCTGATGCAGAGCACTCCAGCTACCAACAATCGCGCACGGAG

AGAACTGCCCCGGTTCATGAACTATACCCTGAACAATGCAAAGAAAACAAATGT

GACTCTGTCCAAGAAACGCAAGAGGCGCTTCCTGGGATTTCTGCTGGGCGTGGG

GTCTGCAATCGCCAGTGGAGTGGCCGTCTCTAAAGTCCTGCACCTGGAGGGCGA

AGTGAACAAGATCAAATCAGCACTGCTGAGCACAAACAAGGCCGTGGTCAGTCT

GTCAAATGGCGTGTCCGTCCTGACTTCTAAGGTGCTGGACCTGAAAAATTATATT

GATAAGCAGCTGCTGCCTATCGTCAACAAACAGAGCTGTTCCATTTCTAATATCG

AGACCGTGATCGAGTTCCAGCAGAAGAACAATAGACTTCTAGAGATTACAAGGG

AATTTTCTGTGAACGCTGGCGTCACTACCCCCGTGAGTACCTACATGCTGACAAA

TAGTGAGCTGCTGTCACTGATTAACGACATGCCTATCACCAATGATCAGAAGAAA

CTGATGAGTAACAATGTGCAGATCGTCAGACAGCAGAGTTACTCAATCATGTCA

ATCATTAAGGAGGAAGTCCTGGCCTACGTGGTCCAGCTGCCACTGTATGGCGTGA

TCGACACTCCCTGCTGGAAACTGCATACCTCACCTCTGTGCACAACTAACACCAA

GGAGGGGAGCAATATCTGCCTGACACGAACTGACCGGGGATGGTACTGTGATAA

CGCCGGCAGCGTGTCCTTCTTTCCCCAGGCTGAGACCTGCAAGGTCCAGTCCAAC

AGGGTGTTCTGTGACACTATGAATAGCCTGACCCTGCCTTCCGAAGTCAACCTGT

GCAATGTGGACATCTTTAATCCAAAGTACGATTGTAAGATCATGACCAGCAAGA

CAGATGTCAGCTCGAGTGTGATTACATCACTGGGGGCTATCGTGAGCTGCTACGG

AAAGACTAAATGTACCGCAAGCAACAAAAATCGCGGCATCATTAAGACCTTCAG

TAACGGGTGCGACTATGTCTCAAACAAGGGCGTGGATACAGTGAGCGTCGGGAA

CACTCTGTACTATGTCAATAAGCAGGAGGGAAAATCCCTGTACGTGAAGGGCGA

-continued

ACCAATCATTAACTTCTATGACCCCCTGGTGTTCCCTTCCGACGAGTTTGATGCCT

CTATTAGTCAGGTGAACGAAAAAATCAATCAGAGCCTGGCTTTTATTCGGAAGTC

CGATGAGCTGCTGCACAACGTGAATGCAGTCAAGTCTACCACAAACATTATGATC

ACTACCATCATTATCGTGATTATCGTCATTCTGCTGTCCCTGATCGCAGTGGGGCT

GCTGCTGTACTGTAAAGCCAGATCTACACCCGTGACTCTGTCTAAGGATCAGCTG

AGTGGAATTAACAATATCGCCTTTAGCAACTGATAGGCTAGCCTCCTGCCATACT

TCCTACTCACATCATATCTATTTTAAAGAAAAAATAGGCCCGAACACTAATCGTG

CCGGCAGTGCCACTGCACACACAACACTACACATACAATACACTACAATGGTTG

CAGAAGATGCCCCTGTTAGGGGCACTTGCCGAGTATTATTTCGAACAACAACTTT

AATTTTTCTATGCACACTATTAGCATTAAGCATCTCTATCCTTTATGAGAGTTTAA

TAACCCAAAAGCAAATCATGAGCCAAGCAGGCTCAACTGGATCTAATTCTAGAT

TAGGAAGTATCACTGATCTTCTTAATAATATTCTCTCTGTCGCAAATCAGATTATA

TATAACTCTGCAGTCGCTCTACCTCTACAATTGGACACTCTTGAATCAACACTCCT

TACAGCCATTAAGTCTCTTCAAACAAGTGACAAGCTAGAACAGAACTGCTCGTG

GGGTGCTGCACTGATTAATGATAATAGATACATTAATGGCATCAATCAGTTCTAT

TTCTCAATTGCTGAGGGTCGCAAGCTGACACTTGGCCCACTTCTTAATATACCTA

GTTTCATTCCAACTGCCACGACACCAGAGGGCTGCACCAGGATCCCATCATTCTC

GCTCACCAAGACACACTGGTGTTATACACACAATGTTATCCTGAATGGATGCCAG

GATCATGTATCCTCAAATCAATTTGTTTCCATGGGAATCATTGAACCCACTTCTGC

CGGGTTTCCATCCTTTCGAACCCTAAAGACTCTATATCTCAGCGATGGGGTCAAT

CGTAAGAGCTGCTCTATCAGTACAGTTCCGGGGGGTTGTATGATGTACTGTTTCG

TCTCTACTCAACCAGAGAGGGATGACTACTTTTCTACCGCTCCTCCAGAACAACG

AATTATTATAATGTACTATAATGATACAATCGTGGAGCGCATAATTAATCCACCC

GGGGTACTAGATGTATGGGCAACATTGAACCCAGGAACAGGAAGCGGGGTATAT

TATTTAGGTTGGGTACTCTTTCCAATATATGGCGGCGTGATTAAAGATACGAGTT

TATGGAATAATCAAGCAAATAAATACTTTATCCCCCAGATGGTTGCTGCTCTCTG

CTCACAAAACCAGGCAACTCAAGTCCAAAATGCTAAGTCATCATACTATAGCAG

CTGGTTTGGCAATCGAATGATTCAGTCTGGGATCCTGGCATGTCCTCTTCAACAG

GATCTAACCAATGAGTGTTTAGTTCTGCCCTTTTCTAATGATCAGGTGCTTATGGG

TGCTGAAGGGAGATTATACATGTATGGTGACTCGGTGTATTACTACCAAAGAAGC

AATAGTTGGTGGCCTATGACCATGCTGTATAAGGTAACCATAACATTCACTAATG

GTCAGCCATCTGCTATATCAGCTCAGAATGTGCCCACACAGCAGGTCCCTAGACC

TGGGACAGGAAGCTGCTCTGCAACAAATAGATGTCCCGGTTTTTGCTTGAAAGGA

GTGTATGCTGATGCCTGGTTACTGACCAACCCTTCGTCTACCAGTACATTTGGATC

AGAAGCAACCTTCACTGGTTCTTATCTCAACGCAGCAACTCAGCGTATCAATCCG

ACGATGTATATCGCGAACAACACACAGATCATAAGCTCACAGCAATTTGGATCA

AGCGGTCAAGAAGCAGCATATGGCCACACAACTTGTTTTAGGGACACAGGCTCT

GTTATGGTATACTGTATCTATATTATTGAATTGTCCTCATCTCTCTTAGGACAATT

TCAGATTGTCCCATTTATCCGTCAGGTGACACTATCCTAAAGGCAGAAGCCTCCA

GGTCTGACCCAGCCAATCAAAGCATTATACCAGACCATGGAATGCATACCAAAC

ATTATTGACACTAATGACACACAAAATTGGTTTTAAGAAAAACCAAGAGAACAA

-continued

TAGGCCAGAATGGCTGGGTCTCGGGAGATATTACTCCCTGAAGTCCATCTCAATT

CACCAATTGTAAAGCATAAGCTATACTATTACATTCTACTTGGAAACCTCCCAAA

TGAGATCGACATTGACGATTTAGGTCCATTACATAATCAAAATTGGAATCAAATA

GCACATGAAGAGTCTAACTTAGCCCAACGCTTGGTAAATGTAAGAAATTTTCTAA

TTACCCACATCCCTGATCTTAGAAAGGGCCATTGGCAAGAGTATGTCAATGTAAT

ACTGTGGCCGCGAATTCTTCCCTTGATCCCGGATTTTAAAATCAATGACCAATTG

CCTCTACTCAAAAATTGGGACAAGTTAGTTAAAGAATCATGTTCAGTAATCAATG

CGGGTACTTCCCAGTGCATTCAGAATCTCAGCTATGGACTGACAGGTCGTGGGAA

CCTCTTTACACGATCACGTGAACTCTCTGGTGACCGCAGGGATATTGATCTTAAG

ACGGTTGTGGCAGCATGGCATGACTCAGACTGGAAAAGAATAAGTGATTTTTGG

ATTATGATCAAATTCCAGATGAGACAATTAATTGTTAGGCAAACAGATCATAATG

ATCCTGATTTAATCACGTATATCGAAAATAGAGAAGGCATAATCATCATAACCCC

TGAACTGGTAGCATTATTTAACACTGAGAATCATACACTAACATACATGACCTTT

GAAATTGTACTGATGGTTTCAGATATGTACGAAGGTCGTCACAACATTTTATCAC

TATGCACAGTTAGCACTTACCTGAATCCTCTGAAGAAAAGAATAACATATTTATT

GAGCCTTGTAGATAACTTAGCTTTTCAGATAGGTGATGCTGTATATAACATAATT

GCTTTGCTAGAATCCTTTGTATATGCACAGTTGCAAATGTCAGATCCCATCCCAG

AACTCAGAGGACAATTCCATGCATTCGTATGTTCTGAGATTCTTGATGCACTAAG

GGGAACTAATAGTTTCACCCAGGATGAATCAAGAACTGTGACAACCAATTTGAT

ATCCCCATTCCAAGATCTGACCCCAGATCTTACGGCTGAATTGCTCTGTATAATG

AGGCTTTGGGGACACCCCATGCTCACCGCCAGTCAAGCTGCGGGAAAGGTACGC

GAGTCCATGTGTGCTGGAAAAGTATTAGACTTTCCCACCATTATGAAAACACTAG

CCTTTTTCCATACTATTCTGATCAATGGATACAGGAGGAAGCATCATGGAGTATG

GCCACCCTTAAACTTACCGGGTAATGCTTCAAAGGGTCTCACGGAACTTATGAAT

GACAATACTGAGATAAGCTATGAATTCACACTTAAGCATTGGAAGGAAATCTCTC

TTATAAAATTCAAGAAATGTTTTGATGCAGACGCAGGTGAGGAACTCAGTATATT

TATGAAAGATAAAGCAATTAGTGCCCCAAAACAAGATTGGATGAGTGTGTTTAG

AAGAAGCCTAATCAAACAGCGCCATCAGCATCATCAGGTCCCCCTACCAAATCC

ATTCAATCGACGGCTATTGCTAAACTTTCTCGGAGATGACAAATTCGACCCGAAT

GTGGAGCTACAGTATGTAACATCAGGTGAGTATCTACATGATGACACGTTTTGTG

CATCATATTCACTAAAAGAGAAGGAAATTAAACCTGATGGTCGAATTTTTGCAAA

GTTGACTAAGAGAATGAGATCATGTCAAGTTATAGCAGAATCTCTTTTAGCGAAC

CATGCTGGGAAGTTAATGAAAGAGAATGGTGTTGTGATGAATCAGCTATCATTA

ACAAAATCACTATTAACAATGAGTCAGATTGGAATAATATCCGAGAAAGCTAGA

AAATCGACTCGAGATAACATAAATCAACCTGGTTTCCAGAATATCCAGAGAAAT

AAATCACATCACTCCAAGCAAGTCAATCAGCGAGATCCAAGTGATGACTTTGAA

TTGGCAGCATCTTTTTTAACTACTGATCTCAAAAAATATTGTTTACAATGGAGGT

ACCAGACAATTATCCCATTTGCTCAATCATTAAACAGAATGTATGGTTATCCTCA

TCTCTTTGAGTGGATTCACTTACGGCTAATGCGTAGTACACTTTACGTGGGGGAT

CCCTTCAACCCACCAGCAGATACCAGTCAATTTGATCTAGATAAAGTAATTAATG

-continued

GAGATATCTTCATTGTATCACCCAGAGGTGGAATTGAAGGGCTATGTCAAAAGG

CTTGGACAATGATATCTATCTCTGTGATAATTCTATCTGCCACAGAGTCTGGCAC

ACGAGTAATGAGTATGGTGCAGGGAGATAATCAAGCAATTGCTGTCACCACACG

AGTACCAAGGAGCCTGCCGACTCTTGAGAAAAAGACTATTGCTTTTAGATCTTGT

AATCTATTCTTTGAGAGGTTAAAATGTAATAATTTTGGATTAGGTCACCATTTGA

AAGAACAAGAGACTATCATTAGTTCTCACTTCTTTGTTTATAGCAAGAGAATATT

CTATCAGGGGAGGATTCTAACGCAAGCCTTAAAAAATGCTAGTAAGCTCTGCTTG

ACAGCTGATGTCCTAGGAGAATGTACCCAATCATCATGTTCTAATCTTGCAACTA

CTGTCATGAGGTTAACTGAGAATGGTGTTGAAAAAGATATCTGTTTCTACTTGAA

TATCTATATGACCATCAAACAGCTCTCCTATGATATCATCTTCCCTCAAGTGTCAA

TTCCTGGAGATCAGATCACATTAGAATACATAAATAATCCACACCTGGTATCACG

ATTGGCTCTTCTGCCATCCCAGCTAGGAGGTCTAAACTACCTGTCATGCAGTAGG

CTGTTCAATCGAAACATAGGCGACCCGGTGGTTTCCGCAGTTGCAGATCTTAAGA

GATTAATTAAATCAGGATGTATGGATTACTGGATCCTTTATAACTTATTAGGGAG

AAAACCGGGAAACGGCTCATGGGCTACTTTAGCAGCTGACCCGTACTCAATCAA

TATAGAGTATCAATACCCCCCAACTACAGCTCTTAAGAGGCACACCCAACAAGCT

CTGATGGAACTCAGTACGAATCCAATGTTACGTGGCATATTCTCTGACAATGCAC

AGGCAGAAGAAAATAATCTTGCTAGATTTCTCCTGGATAGGGAGGTGATCTTTCC

GCGTGTAGCTCACATCATCATTGAGCAAACCAGTGTCGGGAGGAGAAAACAGAT

TCAAGGATATTTGGATTCAACTAGATCGATAATGAGTAAATCACTAGAAATTAAG

CCCTTGTCCAATAGGAAGCTTAATGAAATACTGGATTACAACATCAATTACCTAG

CTTACAATTTGGCATTACTCAAGAATGCTATTGAACCTCCGACTTATTTGAAAGC

AATGACTCTTGAAACATGTAGCATCGACATTGCAAGGAGCCTCCGGAAGCTCTCC

TGGGCCCCACTCTTGGGTGGGAGAAATCTTGAAGGATTAGAGACGCCAGATCCC

ATTGAAATTACTGCAGGAGCATTAATTGTTGGATCGGGCTACTGTGAACAGTGTG

CTGCAGGAGACAATCGATTCACATGGTTTTTCTTGCCATCTGGTATCGAGATAGG

AGGGGATCCCCGTGATAATCCTCCTATCCGTGTACCGTACATTGGCTCCAGGACT

GATGAGAGGAGGGTAGCCTCAATGGCATACATCAGGGGTGCCTCGAGTAGCCTA

AAAGCAGTTCTTAGACTGGCGGGAGTGTACATCTGGGCATTCGGAGATACTCTGG

AGAATTGGATAGATGCACTGGATTTGTCTCACACTAGAGTTAACATCACACTTGA

ACAGCTGCAATCCCTCACCCCACTTCCAACCTCTGCCAATCTAACCCATCGGTTG

GATGATGGCACAACTACCCTAAAGTTTACTCCTGCGAGCTCTTACACCTTTTCAA

GTTTCACTCATATATCAAATGATGAGCAATACCTGACAATTAATGACAAAACTGC

AGATTCAAATATAATCTACCAACAGTTAATGATCACTGGACTCGGAATTTTAGAA

ACATGGAATAATCCCCCAATCAATAGAACATTCGAAGAATCTACCCTACATTTGC

ACACTGGTGCATCATGTTGTGTCCGACCTGTGGACTCCTGCATCATCTCAGAAGC

ATTAACAGTCAAGCCACATATTACAGTACCGTACAGCAATAAATTTGTATTTGAT

GAAGACCCGCTATCTGAATATGAGACTGCAAAACTGGAATCGTTATCATTTCAAG

CCCAATTAGGCAACATTGATGCTGTAGATATGACAGGTAAATTAACATTATTGTC

CCAATTCACTGCAAGGCAGATTATTAATGCAATCACTGGACTCGATGAGTCTGTC

TCTCTTACTAATGATGCCATTGTTGCATCAGACTATGTCTCCAATTGGATTAGTGA

-continued

ATGCATGTATACCAAATTAGATGAATTATTTATGTATTGTGGGTGGGAACTACTA
TTGGAACTATCCTATCAAATGTATTATCTGAGGGTAGTTGGGTGGAGTAATATAG
TGGATTATTCTTACATGATCTTGAGAAGAATCCCGGGTGCAGCATTAAACAATCT
GGCATCTACATTAAGTCATCCAAAACTTTTCCGACGAGCTATCAACCTAGATATA
GTTGCCCCCTTAAATGCTCCTCATTTTGCATCTCTGGACTACATCAAGATGAGTGT
GGATGCAATACTCTGGGGCTGTAAAAGAGTCATCAATGTGCTCTCCAATGGAGG
GGACTTAGAATTAGTTGTGACATCTGAAGATAGCCTTATTCTCAGTGACCGATCC
ATGAATCTCATTGCAAGGAAATTAACTTTATTATCACTGATTCACCATAATGGTTT
GGAACTACCAAAGATTAAGGGGTTCTCTCCTGATGAGAAGTGTTTCGCTTTGACA
GAATTTTTGAGGAAAGTGGTGAACTCAGGGTTGAGTTCAATAGAGAACCTATCA
AATTTTATGTACAATGTGGAGAACCCACGGCTTGCAGCATTCGCCAGCAACAATT
ACTACCTGACCAGAAAATTATTGAATTCAATACGAGATACTGAGTCGGGTCAAGT
AGCAGTCACCTCATATTATGAATCATTAGAATATATTGATAGTCTTAAGCTAACC
CCACATGTGCCTGGTACCTCATGCATTGAGGATGATAGTCTATGTACAAATGATT
ACATAATCTGGATCATAGAGTCTAATGCAAACTTGGAGAAGTATCCAATTCCAAA
TAGCCCTGAGGATGATTCCAATTTCCATAACTTTAAGTTGAATGCTCCATCGCAC
CATACCTTACGCCCATTAGGGTTGTCATCAACTGCTTGGTATAAGGGTATAAGCT
GTTGCAGGTACCTTGAGCGATTAAAGCTACCACAAGGTGATCATTTATATATTGC
AGAAGGTAGTGGTGCCAGTATGACAATCATAGAATACCTATTCCCAGGAAGAAA
GATATATTACAATTCTTTATTTAGTAGTGGTGACAATCCCCCACAAAGAAATTAT
GCACCAATGCCTACTCAGTTCATTGAGAGTGTCCCATACAAGCTCTGGCAAGCAC
ACACAGATCAATATCCCGAGATTTTTGAGGACTTCATCCCTCTATGGAACGGAAA
TGCCGCCATGACTGACATAGGAATGACAGCTTGTGTAGAATTCATCATCAATCGA
GTCGGCCCAAGGACTTGCAGTTTAGTACATGTAGATTTGGAATCAAGTGCAAGCT
TAAATCAACAATGCCTGTCAAAGCCGATAATTAATGCTATCATCACTGCTACAAC
TGTTTTGTGCCCTCATGGGGTGCTTATTCTGAAATATAGTTGGTTGCCATTTACTA
GATTTAGTACTTTGATCACTTTCTTATGGTGCTACTTTGAGAGAATCACTGTTCTT
AGGAGCACATATTCTGGTCCAGCTAATCATGAGGTTTATTTAATTTGTATCCTTGC
CAACAACTTTGCATTCCAGACTGTCTCGCAGGCAACAGGAATGGCGATGACTTTA
ACCGATCAAGGGTTTACTTTGATATCACCTGAAAGAATAAATCAGTATTGGGATG
GTCACTTGAAGCAAGAACGTATCGTAGCAGAAGCAATTGATAAGGTGGTTCTAG
GAGAAGATGCTCTATTCAATTCGAGTGATAATGAATTAATTCTCAAATGTGGAGG
GACACCAAATGCACGGAATCTTATCGATATCGAGCCAGTCGCAACTTTCATAGAA
TTTGAACAACTGATCTGCACAATGTTGACAACCCACTTGAAGGAAATAATTGATA
TAACAAGGTCTGGAACCCAGGATTATGAAAGTTTATTACTCACTCCTTACAATTT
AGGTCTTCTTGGTAAAATCAGTACGATAGTGAGATTATTAACAGAAAGGATTCTA
AATCATACTATCAGGAATTGGTTGATCCTCCCACCTTCGCTCCGGATGATCGTGA
AGCAGGACTTGGAATTCGGCATATTCAGGATTACTTCCATCCTCAATTCTGATCG
GTTCCTGAAGCTTTCTCCAAATAGGAAATACTTGATTACACAATTAACTGCAGGC
TACATTAGGAAATTGATTGAGGGGGATTGTAATATCGATCTAACCAGACCTATCC

-continued

AAAAACAAATCTGGAAAGCATTAGGTTGTGTAGTCTATTGTCACGATCCAGTAGA

TCAAAGGGAATCAACAGAGTTTATTGATATAAATATTAATGAAGAAATAGACCG

CGGGATCGATGGCGAGGAAATCTAAATATATCAAGAATCAGAATTAGTTTAAGA

AAAAAGAAGAGGATTAATCTTGGTTTTCCCCTTGGT

IV. Methods of Treatment

The disclosure can be used in gene therapy and/or therapeutic approaches for the treatment of disease which involve the increase or decrease of a nucleotide sequence of interest in a host-cell. In these embodiments, the expressible heterologous nucleotide sequence may be derived from a mammalian genome. It may be particularly useful in some embodiments to have the expressible heterologous nucleotide sequence derived from a human genome, wherein expression of the wild-type RNA and/or protein can produce therapeutic effects in a patient. For example, the expressible heterologous nucleotide sequence can encode CFTR, NeuroD1, Cas9 and Guide RNAs, or any other such sequence. In other embodiments, the heterologous nucleotide sequence encodes a secreted protein.

In other embodiments, the expressible heterologous nucleotide sequence responds to positive selection stimuli. In other embodiments, the expressible heterologous nucleotide sequence also responds to negative selection stimuli. In further embodiments, it may be useful for the polynucleotide sequences to further comprise a reporter gene. For example, the report gene can be a luciferase or green fluorescent protein.

V. Methods of Administration

A. Administration by Vaccination

The present invention includes methods of vaccinating a subject by administering a viral expression vector, viral particle, or composition as described herein to the subject.

The invention provides the use of a live recombinant PIV5 based vaccine consisting of canine parainfluenza (CPI) engineered to express the RSV F protein as target antigen to develop a CPI-RSV-F vaccine as a novel prophylactic vaccine against RSV infection.

i. Intranasal Vaccination

In one embodiment, the disclosed CPI-RSV-F compositions are formulated to allow intranasal administration. A number of non-clinical studies have been conducted to evaluate the immunogenicity and efficacy of CPI-RSV-F or very close related vaccine construct (e.g. W3A PIV5 based constructs) expressing RSV F protein in various animal models using the intranasal (i.n.) route. This included earlier developmental studies in mice, cotton rats and African green monkeys (AGM) evaluating variations of the vector construct (location of F protein in vector) and of the RSV F protein insert (wild type or prefusion F protein). The findings from these studies are summarized and the publications are hereby included by incorporation.

Intranasal compositions may comprise an inhalable dry powder pharmaceutical formulation comprising a therapeutic agent, wherein the therapeutic agent is present as a freebase or as a mixture of a salt and a freebase. Pharmaceutical formulations disclosed herein can be formulated as suitable for airway administration, for example, nasal, intranasal, sinusoidal, peroral, and/or pulmonary administration. Typically, formulations are produced such that they have an appropriate particle size for the route, or target, of airway administration. As such, the formulations disclosed herein can be produced so as to be of defined particle size distribution.

For example, the particle size distribution for a salt form of a therapeutic agent for intranasal administration can be between about 5 μm and about 350 μm. More particularly, the salt form of the therapeutic agent can have a particle size distribution for intranasal administration between about 5μ to about 250 μm, about 10 μm to about 200 μm, about 15 μm to about 150 μm, about 20 μm to about 100 μm, about 38 μm to about 100 μm, about 53 μm to about 100, about 53 μm to about 150 μm, or about 20 μm to about 53 μm. The salt form of the therapeutic agent in the pharmaceutical compositions of the invention can a particle size distribution range for intranasal administration that is less than about 200 μm. In other embodiments, the salt form of the therapeutic agent in the pharmaceutical compositions has a particle size distribution that is less than about 150 μm, less than about 100 μm, less than about 53 μm, less than about 38 μm, less than about 20 μm, less than about 10 μm, or less than about 5 μm. The salt form of the therapeutic agent in the pharmaceutical compositions of the invention can have a particle size distribution range for intranasal administration that is greater than about 5 μm, greater than about 10 μm, greater than about 15 μm, greater than about 20 μm, greater than about 38 μm, less than about 53 μm, less than about 70 μm, greater than about 100 μm, or greater than about 150 μm.

Additionally, the salt form of the therapeutic agent in the pharmaceutical compositions of the invention can have a particle size distribution range for pulmonary administration between about 1 μm and about 10 μm. In other embodiments for pulmonary administration, particle size distribution range is between about 1 μm and about 5 μm, or about 2 μm and about 5 μm. In other embodiments, the salt form of the therapeutic agent has a mean particle size of at least 1 μm, at least 2 μm, at least 3 μm, at least 4 μm, at least 5 μm, at least 10 μm, at least 20 μm, at least 25 μm, at least 30 μm, at least 40 μm, at least 50 μm, at least 60 μm, at least 70 μm, at least 80 μm, at least 90 μm, or at least 100 μm.

In some embodiments the disclosed cannabinoid compositions include one or more cannabinoids or pharmaceutically acceptable derivatives or salts thereof, a propellant, an alcohol, and a glycol and/or glycol ether. The alcohol may be a monohydric alcohol or a polyhydric alcohol, and is preferably a monohydric alcohol. Monohydric alcohol has a lower viscosity than a glycol or glycol ether. Accordingly, the composition is able to form droplets of a smaller diameter in comparison to compositions in which the monohydric alcohol is not present. The present inventors have surprisingly found that a specific ratio of monohydric alcohol to glycol or glycol ether results in a composition with a desired combination of both long term stability (for example the composition remains as a single phase for at least a week at a temperature of 2-40° C.) and small droplet size.

a. Vaccine Immunogenicity and Protection in Lower Respiratory Tract of Mice

One embodiment provides candidate vaccine viruses administered intranasally which elicited high levels of anti-F serum antibodies in both CHD03 and CHD04 studies. In W3AΔSH-RSV-F vaccinated animals, the geometric mean titer of RSV F antibody titer was 3.1 $Log_{10}$/mL in CHD03 and 3.4 $Log_{10}$/mL in CHD04. In CPI-RSV-F vaccinated animals, the geometric mean titer was 3.0 $Log_{10}$/mL in CHD03 and 3.2 $Log_{10}$/mL in CHD04. These values are not statistically significant from each other, and they are similar to the values from RSV_rA2 positive control group. Both vaccine viruses also elicited RSV F protein specific cellular responses as measured by IFN-γ secreting cells. In CHD03, W3AΔSH-RSV-F had a geometric mean value of 28 IFN-γ secreting cells while CPI-RSV-F had a geometric mean of 23 IFN-γ secreting cells per $10^6$ splenocytes. In CHD04, W3AΔSH-RSV-F and CPI-RSV-F had geometric means of 35 IFN-γ secreting cells and 48 IFN-γ secreting cells per $10^6$ splenocytes, respectively. These values were statistically significant from the PBS control group, but not different between the vaccinated groups or the RSV_rA2 positive control group. IFN-γ secreting cells in CPI-RSV-F group in CHD04 was significantly higher than positive control. Both W3AΔSH-RSV-F and CPI-RSV-F had significantly lower RSV challenge viral titers compared to PBS control group in both CHD03 and CHD04. The values were 1.35 $Log_{10}$ PFU/g and 1.37 $Log_{10}$ PFU/g for W3AΔSH-RSV-F and 1.48 $Log_{10}$ PFU/g and 1.40 $Log_{10}$ PFU/g CPI-RSV-F, respectively for CHD03 and CHD04 compared to 3.21 $Log_{10}$ PFU/g and 3.33 $Log_{10}$ PFU/g in the PBS control groups. The RSV_rA2 positive control group had values of 1.39 $Log_{10}$ PFU/g in CHD03 and 1.32 $Log_{10}$ PFU/g in CHD04, which is similar to the vaccine groups of interest.

Overall, the results presented herein demonstrate that W3AλSH-RSV-F and CPI-RSV-F, as well as the other two candidates (W3A-RSV-F (SH-HN) and CPIλSH-RSV-F), administered intranasally at a dose level of $10^5$ PFU, induced comparable RSV-specific immune responses and significant protection against RSV challenge virus replication in the lower respiratory tract of BALB/c mice.

b. Preclinical Testing of PIV5ΔSH-RSV-F Vaccine Based on CPI Strain of PIV5 in the Cotton Rat Virus Challenge Model Using RSV A/A2 Virus Strain. Comparison to PIV5 W3A-Based PIV5ΔSH-RSV-F Vaccine.

Efficacy and safety of RSV F protein vaccine candidates based on the CPI strain or the W3A strain of PIV5 (CPI-RSV-F and W3AΔSH-RSV-F, respectively) were evaluated in the cotton rat *Sigmodon hispidus* model of RSV A/A2 challenge. Animals were first immunized with 100 μl of the PIV5-based vaccines containing $10^4$, $\mathbf{10^5}$, or $10^6$ PFU of virus intranasally and then challenged with $10^5$ PFU RSV A/A2 four weeks later. The primary infection control group was mock-immunized with PBS and then infected with RSV A/A2. The secondary infection control group was infected with RSV A/A2 and re-infected seven weeks later. The vaccine-enhanced disease control group was immunized with FI-RSV twice with an interval of four weeks and infected with RSV three weeks after the second immunization. Animals were sacrificed five days after RSV challenge for sample collection. RSV replication in the lung and nose, pulmonary histopathology, pulmonary cytokine and RSV NS1 mRNA expression, and the RSV serum neutralizing antibody (NA) and the anti-F protein binding antibody titers were measured. To confirm replication of the PIV5 vaccines in the respiratory tract of cotton rats, groups of 3 animals were inoculated with $10^6$ PFU of CPI-RSV-F or W3AΔSH-RSV-F intranasally and sacrificed four days later. These samples were submitted for plaque assay evaluation. In brief, it was found that both candidate vaccine viruses replicated efficiently in the upper and lower respiratory track of cotton rats. W3AΔSH-RSV-F vaccine virus replicated to higher levels in the upper respiratory tract compared to CPI-RSV-F, but it replicated to lower levels in the lower respiratory tract compared to CPI-RSV-F.

Both CPI-RSV-F and W3AΔSH-RSV-F vaccines were highly efficacious at protecting the lung of cotton rats, inducing near sterilizing immunity at all vaccine doses tested, as indicated by the plaque assay and qPCR. All doses of both vaccines also induced statistically significant protection of the nose that was stronger for W3AΔSH-RSV-F compared to CPI-RSV-F immunization.

W3AΔSH-RSV-F reduced nasal viral load to almost undetectable levels at all three vaccine doses tested. For CPI-RSV-F, the $10^6$ PFU dose induced the strongest protection, followed by the $10^5$ PFU and $10^4$ PFU doses. Both CPI-RSV-F and control vaccines induced a strong NA response, with control, in all three doses tested, inducing higher titers of NA compared to CPI-RSV-F administered at the highest dose ($10^6$ PFU). Lower doses of CPI-RSV-F induced a weaker NA response. Both CPI-RSV-F and W3AΔSH—RSV-F immunizations induced high levels of binding IgG that was slightly higher for W3AΔSH-RSV-F vaccination. None of the vaccines induced the level of pulmonary histopathology or IL-4 mRNA expression that was seen in FI-RSV-immunized animals, with the exception of one animals immunized with the intermediate dose ($10^5$ PFU) of W3AΔSH—RSV-F. Overall, efficacy of W3AΔSH-RSV-F vaccine appears to exceed that of CPI-RSV-F in regards to nasal protection and neutralizing antibody response in all doses tested. Increasing the dose of W3AΔSH-RSV-F from $10^4$ to $10^6$ PFU provided no apparent advantage in terms of improving vaccine efficacy.

ii. Pulmonary Compositions

One embodiment provides a formulation and method for treating SARS-COV-2 in the pulmonary system by inhalation or pulmonary administration. The diffusion characteristics of the particular drug formulation through the pulmonary tissues are chosen to obtain an efficacious concentration and an efficacious residence time in the tissue to be treated. Doses may be escalated or reduced or given more or less frequently to achieve selected blood levels. Additionally, the timing of administration of administration and amount of the formulation is preferably controlled to optimize the therapeutic effects of the administered formulation on the tissue to be treated and/or titrate to a specific blood level.

Diffusion through the pulmonary tissues can additionally be modified by various excipients that can be added to the formulation to slow or accelerate the absorption of drugs into the pulmonary tissues. For example, the drug may be combined with surfactants such as the phospholipids, dimyristoylphosphatidyl choline, and of administration dimyristoylphosphatidyl glycerol. The drugs may also be used in conjunction with bronchodilators that can relax the bronchial airways and allow easier entry of the antineoplastic drug to the lung. Albuterol is an example of the latter with many others known in the art. Further, the drug may be complexed with biocompatible polymers, micelle forming structures or cyclodextrins.

Particle size for the aerosolized drug used in the present examples was measured at about 1.0-5.0 μm with a GSD less than about 2.0 for deposition within the central and peripheral compartments of the lung. As noted elsewhere herein particle sizes are selected depending on the site of desired deposition of the drug particles within the respiratory tract.

Aerosols useful in the invention include aqueous vehicles such as water or saline with or without ethanol and may contain preservatives or antimicrobial agents such as benzalkonium chloride, paraben, and the like, and/or stabilizing agents such as polyethyleneglycol.

Powders useful in the invention include formulations of the neat drug or formulations of the drug combined with excipients or carriers such as mannitol, lactose, or other sugars. The powders used herein are effectively suspended in a carrier gas for administration. Alternatively, the powder may be dispersed in a chamber containing a gas or gas mixture which is then inhaled by the patient.

An agent of the present disclosure may be administered at once or may be divided into a number of multiple doses to be administered at intervals of time. For example, agents of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

In some aspects, any of the PIV5-based constructs and methods described in WO 2013/112690 and WO 2013/112720 (which is hereby incorporated by reference herein in its entirety) may be used in the present invention.

As used herein, the term "subject" represents an organism, including, for example, a mammal. A mammal includes, but is not limited to, a human, a non-human primate, and other non-human vertebrates. A subject may be an "individual," "patient," or "host." Non-human vertebrates include livestock animals (such as, but not limited to, a cow, a horse, a goat, and a pig), a domestic pet or companion animal, such as, but not limited to, a dog or a cat, and laboratory animals. Non-human subjects also include non-human primates as well as rodents, such as, but not limited to, a rat or a mouse. Non-human subjects also include, without limitation, poultry, horses, cows, pigs, goats, dogs, cats, guinea pigs, hamsters, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

EXAMPLES

Example 1: Immunogenicity of CPI-RSV-F in African Green Monkeys (AGM)(Non-GLP study)

Objective: To compare immunogenicity of CPI-RSV-F and W3AΔSH-RSV-F administered intranasally as a single dose in the African green monkey model.

Methods

Four monkeys in each dose group were immunized at Day 0 with $10^6$ PFU intranasally of either CPI-RSV-F (Group 6) or control (Group 1).

Results

The antibody responses to RSV F-protein and PIV5 vector at Day 28 were determined by ELISA assays (plates coated with recombinant RSV F protein, source Sino Biologicals: 11049-V088 LC120C 2910, or PIV5 wild type virus) as shown in Table 4. In summary, all animals developed antibodies against the F protein expressed by the CPI or W3AΔSH vector with comparable RSV F ELISA titers between the two groups.

TABLE 4

Serum antibody response to RSV F and PIV5 in the AGM study.

| Group | Animal ID | RSV F ELISA titer Day 0 | RSV F ELISA titer Day 28 | PIV5 ELISA titer Day 0 | PIV5 ELISA titer Day 28 |
|---|---|---|---|---|---|
| Group 1 | #1 _09818 | 120 | 3240 | <40 | 3240 |
| W3AΔSH- | #2_09836 | 120 | 3240 | 40 | 3240 |
| RSV-F | #3_90071 | 40 | 1080 | 40 | 9720 |
| | #4_58181 | 40 | 1080 | 120 | 9720 |
| Group 6 | #1_09669 | 360 | 1080 | <40 | 1080 |
| CPI-RSV-F | #2_09839 | 360 | 1080 | 40 | 1080 |
| | #3_09854 | 40 | 3240 | <40 | 360 |
| | #4_09861 | 120 | 3240 | <40 | 9720 |

Figure 1B:
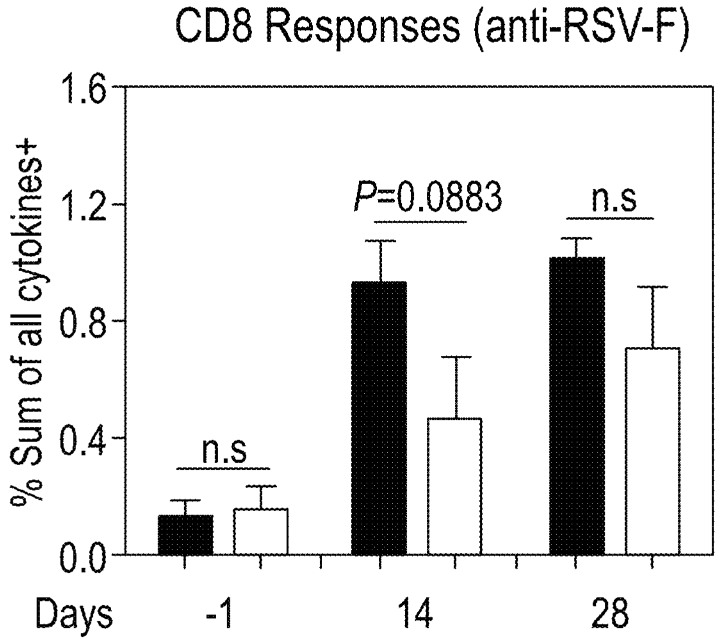

Cell Mediated Responses: RSV F protein-specific cellular responses were evaluated by intracellular cytokine staining (ICS) assay. Following immunization, blood was collected at days-1, 14, and 28 to quantify the RSV F protein-specific CD4 and CD8 cellular responses. INFγ, TNFα, MIP-1b, IL-13, and CD107a positive cells were quantitated (see FIGS. 1A-1B). PBMCs collected at day −1 prior to immunization failed to respond to RSV F peptide stimulation as expected. Following immunization, AGMs immunized with W3AΔSH-RSV-F (Group 1) and CPI-RSV-F (Group 6) generated CD4 and CD8 cellular responses that are RSV F protein-specific as assessed on Day 14 and Day 28. No F-specific cellular response was detected in the control animals (data not shown), and the cellular responses from animals immunized with W3AΔSH-RSV-F and CPI-RSV-F increased from day 14 to day 28 post-immunization (FIGS. 1A-1B). W3AΔSH-RSV-F elicited lower CD4 responses than CPI-RSV-F at day 14, but the difference was not statistically significant. At day 28 post-immunization, W3AΔSH-RSV-F induced higher CD4 responses than CPI-RSV-F, but again this difference was not statistically significant. The CD8 specific responses elicited by W3AΔSH-RSV-F were higher than CPI-RSV-F, however the difference was not statistically significant on day 14 (P=0.0883) or day 28.

Both CPI-RSV-F and W3AΔSH-RSV-F elicited immune responses against RSV F protein. The antibody responses against RSV F protein elicited by either CPI-RSV-F or W3AΔSH-RSV-F were comparable following a single intranasal dose at $10^6$ PFU. The CD4 and CD8 cellular responses elicited by CPI-RSV-F were slightly lower than W3AΔSH—RSV-F, but the difference was not statistically significant.

Example 2: Manufacturing Process and Process Controls

Step 1: Vaccine Vector Construction

Figure 2A:
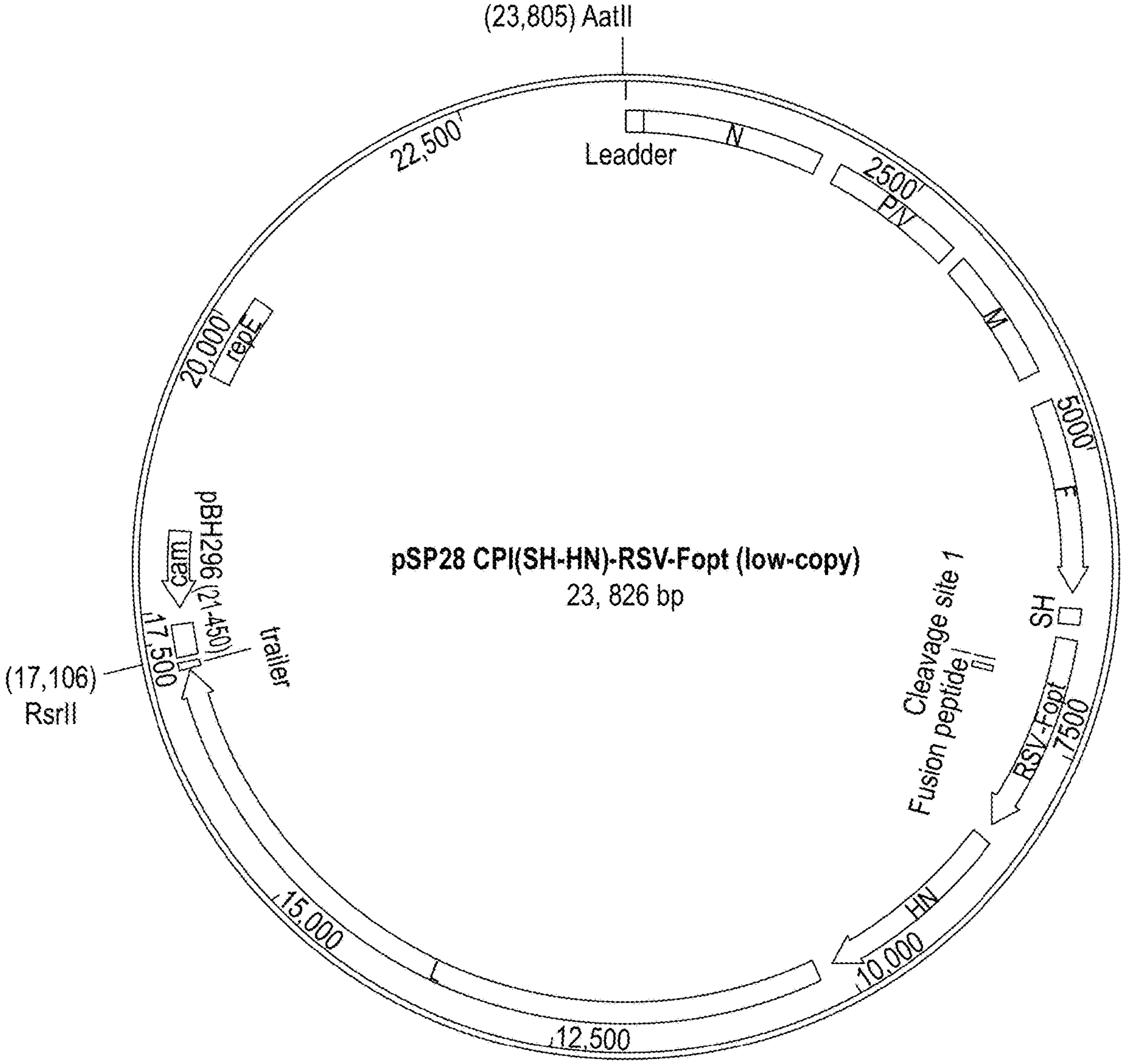
FIGS. 2A-2B show a plasmid map of pSP28 (FIG. 2A) and pAB94 (FIG. 2B).
Figure 2B:
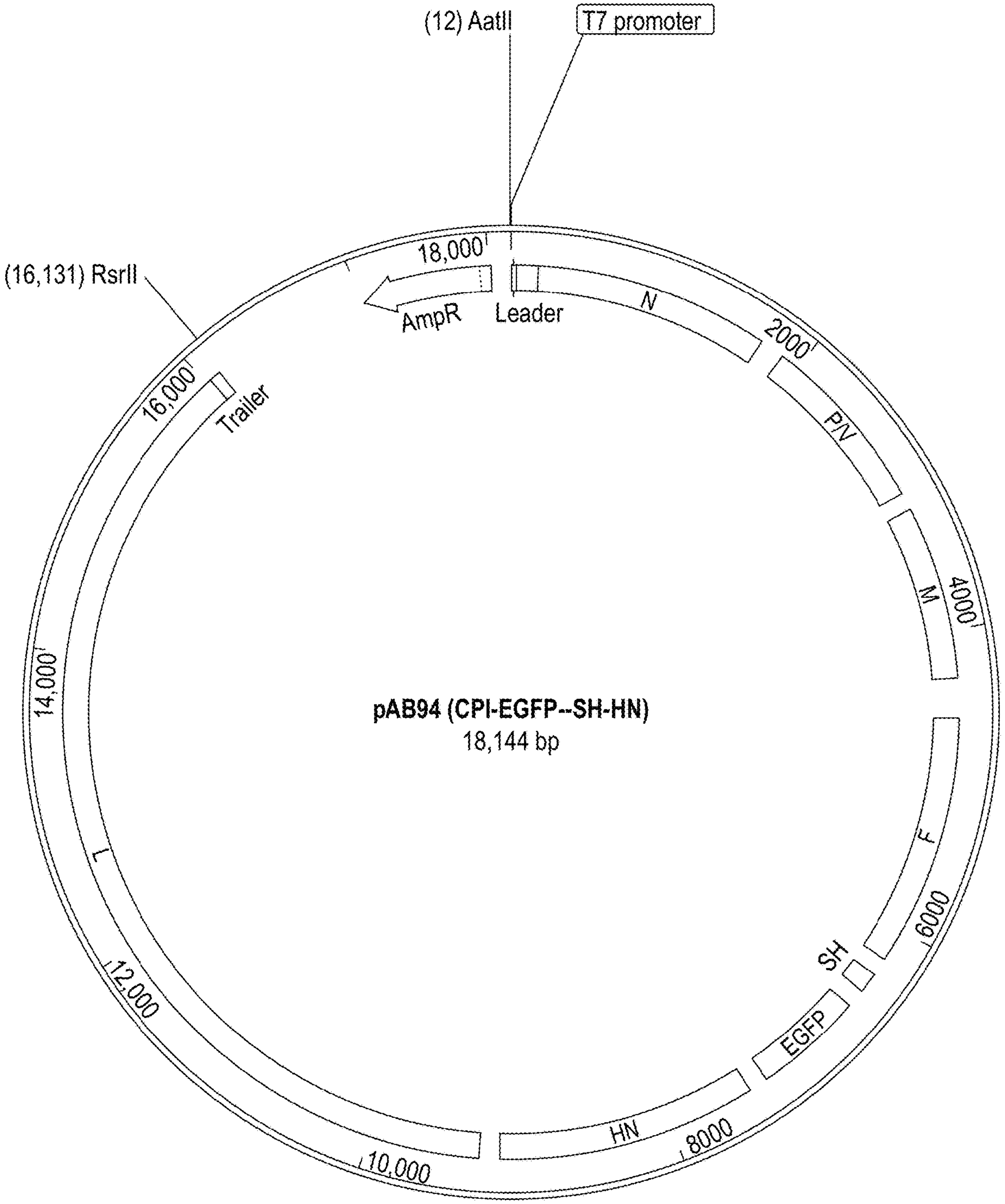

Construction of pCVL41 (CPI-RSV-F) antigenomic cDNA: CPI-RSV-Fopt genome was obtained through RsrII and AatII restriction enzyme digestion of pSP28 plasmid. pSB28 is a low copy plasmid containing the codon optimized RSV F protein gene (Fopt, sequence based on GenBank Accession M74568, RSV A2 strain, codon optimized for humans) inserted between the SH and HN junction of the CPI antigenomic cDNA (FIG. 2A) (3). pAB94 plasmid with the EGFP gene inserted between the SH and HN junction of the CPI antigenomic cDNA is a high copy plasmid (FIG. 2B). The RsrII and AatII restriction enzyme digested Fopt gene from CPI-RSV-Fopt was inserted into the RSrII and AatII digested pAB94 to replace the EGFP gene with the Fopt using T4 DNA ligase.

The ligated cDNA was transformed into TOP10 competent cells, single colonies were grown in LB media containing chloramphenicol.

Figure 3:
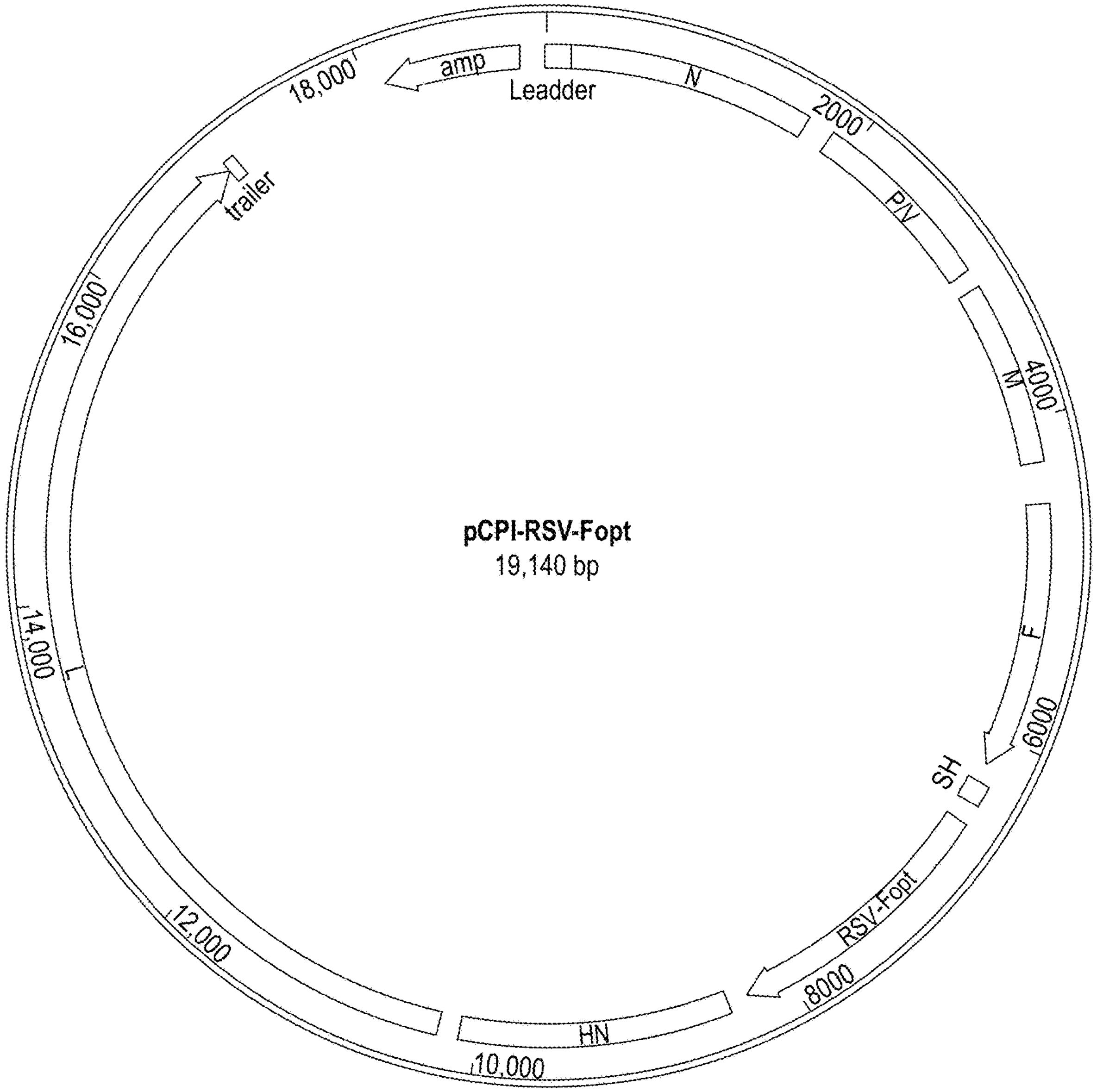
FIG. 3 shows the CPI-RSV-F vaccine vector plasmid and map.

The resultant plasmid DNA (designated pCVL41 or pCPI-RSV-Fopt; FIG. 3) was purified by Qiagen miniprep kit and sequenced. The codon optimized RSV-F gene inserted between the SH and HN gene junction was confirmed to be correct by Sanger sequencing.

Step 2: Vaccine Vector Rescue

Figure 4:
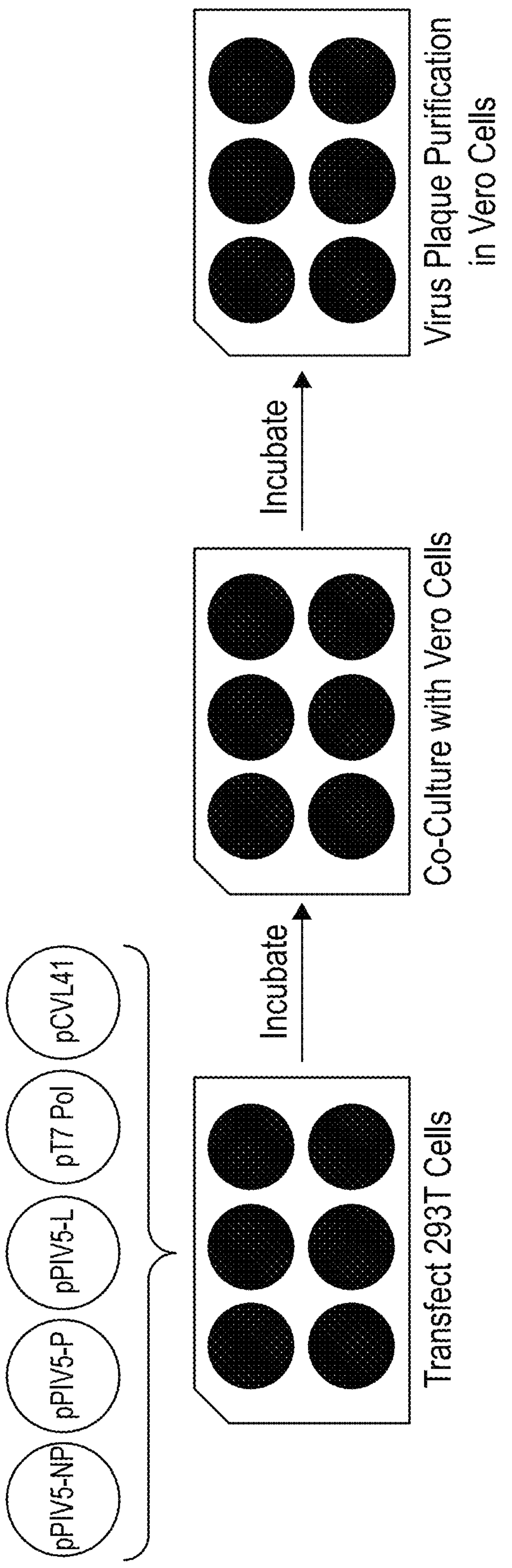
FIG. 4 shows an illustrative overview of virus rescue.

Rescue of the recombinant vector virus used in the production of CPI-RSV-F (CPI-RSV-F) was performed. For the rescue of the recombinant CPI-RSV-F virus, the pCPI-RSV-Fopt plasmid was transfected into serum-free 293T suspension cells (obtained from GenHunter Corporation) together with plasmids encoding the PIV5 NP, P, L proteins and T7 RNA Polymerase allowing for the rescue of recombinant virus from the transfected cell culture (FIG. 4).

The supporting PIV5 plasmid clones encoding the nucleoprotein (N), phosphoprotein (P) or large polymerase protein (L) were described previously (1,2) each gene is under the T7 promoter in pCAGGSvector. The following 5 plasmids were used in the generation of CPI-RSV-F RVS.

1. pCPI-RSV-Fopt (pCVL41-CPI-RSV-F antigenomic cDNA): This plasmid is a high-copy plasmid and it contains an ampicillin resistance gene. It encodes RSV F antigen gene inserted between the SH and HN gene junction of canine parainfluenza virus (CPI).
2. pCAGGS-NP Plasmid: This plasmid contains the PIV5 NP gene under the T7 promoter with anampicillin resistance gene.
3. pCAGGS-P Plasmid: This plasmid contains the PIV5 P gene under the T7 promoter with anampicillin resistance gene.
4. pCAGGS-L Plasmid: This plasmid contains the PIV5 L gene under the T7 promoter with anampicillin resistance gene.
5. pCAGGS-T7 Plasmid (same as pBH437-T7): This plasmid encodes the T7 RNA polymerase gene under the SV40 promoter.

The medium used for virus rescue was CDM4HEK293 medium (Hyclone) with 4 mM GlutaMAX (Gibco).

Following two days of incubation, the 293T cells were co-cultured with serum-free Vero cells (P159) passaged from Vero MCB cells (obtained from CRL: African Green Monkey Kidney (WHO Vero 10-87) Cyan Vac MCB DOM: 19 Aug. 2020-P148). After 4 days of incubation, 2 mL of supernatant containing the rescued virus was obtained and mixed with 10×SPG and stored at −80° C.

Step 3: Plaque Purification and Expansion of Virus Rescue Seed

Aliquots of the frozen stock with rescued virus were serially diluted to perform a plaque assay on serum-free Vero cells (P155-derived from WHO Vero 10-87 Cyan Vac MCB DOM: 19 Aug. 2020) in 6-well plates, with the objective of obtaining 6 isolated single plaques. A 1000 µL pipette tip was used to poke a single plaque and re-suspend in VP-SFM media containing 4 mM GlutaMAX. The re-suspended plaque was then used to infect fresh serum-free Vero cells (P155-derived from WHO Vero 10-87 Cyan Vac MCB DOM:19 Aug. 2020) in a 6-well plate. After 6 days, the supernatant (2 mL) from the 6-well plate infected with single plaque was mixed with 10% 10×SPG and stored at −80° C. (to result in 1×SPG). This material was designated as Lot #CPI-RSV-F-PP1-PQ10-42621, date of manufacture Apr. 6, 2021). Part of the supernatant (140 µL was used to do RNA extraction and RT-PCR to verify viral genomic sequence. The RT-PCR was done with the primers described in Table 5.

TABLE 5

Primers used for amplifying viral cDNAs for sequencing of CPI-RSV-F antigenomic cDNA

| Number | Name | Sequence (5' to 3') | SEQ ID NO: |
|---|---|---|---|
| 1 | CVL1 | ACCAAGGGGAAAATGAAGTGGTGAC | 2 |
| 2 | CVL6 | GGAGAAGCTCAGATCAGTGGGATC | 3 |
| 3 | CVL5 | ACAGTGGATTCCATAAGGTTCCTGC | 4 |
| 4 | CVL11 | CACTGACAGAAATGTCGGAATGAAGAG | 5 |
| 5 | CVL10 | TCCAGGTCACTGTTAGGAAGACATC | 6 |
| 6 | CVL20 | GCTCGATTACCTAGATTGACCGAGAC | 7 |
| 7 | CVL17 | CAAGATGCACCTTCTCTCCAGTG | 8 |

TABLE 5-continued

Primers used for amplifying viral cDNAs for sequencing of CPI-RSV-F antigenomic cDNA

| Number | Name | Sequence (5' to 3') | SEQ ID NO: |
|---|---|---|---|
| 8 | CVL154 | ATCACACTCGAGCTGACATCTGTC | 9 |
| 9 | CVL152 | CGTGAGTACCTACATGCTGACA | 10 |
| 10 | CVL25 | CGGATTGATACGCTGAGTTGCTG | 11 |
| 11 | CVL19 | TAACTCTGCAGTCGCTCTACCTC | 12 |
| 12 | CVL27 | CAGTCTGAGTCATGCCATGCTG | 13 |
| 13 | CVL26 | GCATTCAGAATCTCAGCTATGGACTG | 14 |
| 14 | CVL33 | TCAATGATGATGTGAGCTACACGC | 15 |
| 15 | CVL32 | GCTCTGATGGAACTCAGTACGAATC | 16 |
| 16 | CVL37 | GGTTCTCTATTGAACTCAACCCTGAG | 17 |
| 17 | CVL36 | GTGACCGATCCATGAATCTCATTGC | 18 |
| 18 | CVL42 | ACCAAGGGGAAAACCAAGATTAATCC | 19 |

Step 4: Manufacture of prMVS (Lot #210519MCBCHD-PQ10) on Serum Free Vero Cells

An aliquot from Lot #CPI-RSV-F-PP1-PQ10-42621 (plaque purified virus) was used to infect serum-free Vero cells (P159, derived from WHO Vero 10-87 Cyan Vac MCB DOM:19 Aug. 2020) in T75 flask, incubated at 37° C. for 5 days and the cell culture supernatants were centrifuged at 1,500 rpm for 10 minutes at 4° C. to remove cell debris. The clarified supernatants (20 mL) were mixed with 10% 10× SPG with 10% Arginine (Sigma Aldrich), fast frozen in 1 mL aliquots and stored at −80° C. as pre-MVS stock. The pre-MVS was designated as Lot #210519MCBCHD-PQ10. The pre-MVS was sequenced from the NP gene through the L gene to confirm the viral genomic sequence and proper insertion of the RSV F protein (a single silent mutation was found in AA54 of the NP).

The pre-MVS (Lot #210519MCBCHD-PQ10) prior to use in cGMP production of the MVS was tested at CRL for sterility (direct method), bacteriostasis and fungistasis, *mycoplasma*, mycobacteria, presence of porcine and bovine circoviruses, and in apparent viruses.

The ability of the CPI-RSV-F vaccine vector construct to infect Vero cells and express functional F-protein including prefusion F protein was assessed for both pre-MVS and MVS stock as detailed below using immunofluorescence assay (IFA). In addition, the pre-MVS and MVS were sequenced by Sanger method to confirm presence of correct F-protein gene insert in the PIV5 viral backbone (sequenced from the leader region to the trailer region).

The following characterization testing was performed on pre-MVS of Lot #210519MCBCHD-PQ10).

Figure 5A:
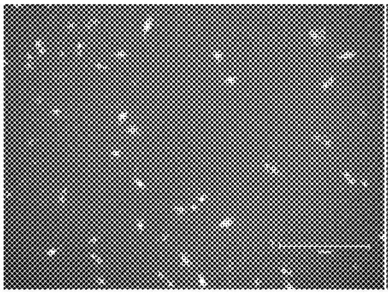
FIGS. 5A-5C show representative images of RSV F-protein percent expression assay CPI-RSV-F pre-MVS.
Figure 5B:
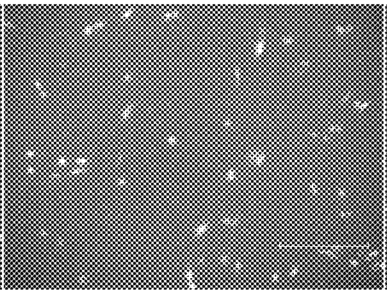
Figure 5C:
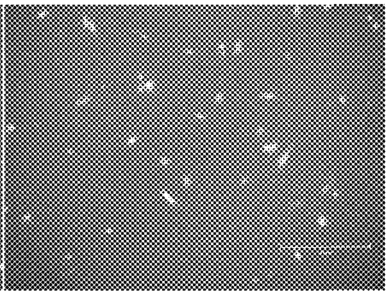

Expression of F-protein by CPI-RSV-F pre-MVS in infected Vero cells by IFA: The expression of F-protein by CPI-RSV-F was assessed by IFA staining for PIV5 vector (HN) and RSV F-protein using Palivizumab, a humanized murine monoclonal antibody that recognizes antigenic site II on both the prefusion (pre-F) and post fusion (post-F) conformations of the respiratory syncytial virus (RSV) F glycoprotein. The percentage F expression was determined by calculating number of cells staining positive for PIV5 (HN protein) that also stained positive for F-protein (FIGS. 5A-5C and Table 6).

TABLE 6

Percent Co-Expression CPI-RSV-F pre-MVS.

| Total Red Foci (PIV5) | Total Green Foci (RSV F) | Percentage RSV F Expression |
|---|---|---|
| 43.4 | 43.4 | 100% |

Vero-SF cells were infected with CPI-RSV-F pre-MVS virus at dilutions 10-, 100- and 1000-fold. After 1-hour incubation at 37° C., the medium was changed, and cells were incubated for 18 hours at 37° C. Immunostaining was performed using mouse anti-PIV5-HN and human anti-F (Palivizumab) antibodies followed by anti-mouse Cy3 and anti-human FITC secondary antibodies, respectively. FIGS. 5A-5C are representative images of wells infected with CPI-RSV-F pre-MVS showing both red and green cells. Table 6 shows the percent expression of RSV F protein in PIV5-infected cells. Images were taken at 10×.

Figure 6A:
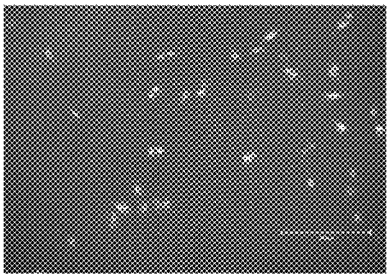
FIGS. 6A-6C show representative images of RSV F-protein percent expression assay CPI-RSV-F MVS.
Figure 6B:
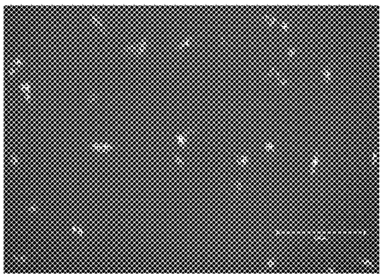
Figure 6C:
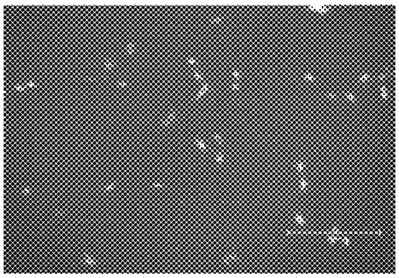

Expression of F-protein by CPI-RSV-F MVS infected cells by IFA: The expression of F-protein by CPI-RSV-F was assessed by IFA staining for PIV-5 vector (HN) and F-protein as per CVL-protocol-034. The percentage expression was determined by calculating number of cells staining positive for PIV5 (HN protein) that also stained positive for RSV F-protein (FIGS. 6A-6C and Table 7).

TABLE 7

Percent Co-expression of RSV-F and PIV5 for CPI-RSV-F (MVS).

| Total Red Foci (PIV5) | Total Green Foci (RSV F) | Percentage RSV F Expression |
|---|---|---|
| 35.4 | 35.2 | 99.4% |

Vero-SF cells were infected with CPI-RSV-F MVS virus at dilutions 100-, 1000-, and 10000-fold. After 1-hour incubation at 37° C., media was changed, and cells were incubated for 18 hours at 37° C. Immunostaining was performed using mouse anti-PIV5-HN and human anti-F (Palivizumab) antibodies followed by anti-mouse Cy3 and anti-human FITC secondary antibodies, respectively. FIGS. 6A-6C are representative images of wells infected with CPI-RSV-F MVS showing both green and red cells. Table 7 shows the percent expression of RSV F protein in PIV5-infected cells. Images were taken at 10×.

Step 5: Manufacturing Process for MVS

The production of the CPI-RSV-F MVS was performed in adherence to cGMP. The Master Virus Seed stock (MVS) which also serves as the Phase 1 clinical lot material was produced using serum free Vero cells, Cyan Vac MCB (DOM:19 Aug. 2020, expanded at CRL to passage 152) in adherence to cGMP at CRL August 2021 (CBR-1862).

Vaccine bulk substance manufacture: The Vero cells grown in T225 flasks in serum free media (VP-SFM) were infected with CPI-RSV-F pre-MVS Lot #210519MCBCHD-PQ10 (using 2 vials) at MOI of 0.002 at 37° C. for 7 days. The cell culture fluid of infected cells constitutes the crude vaccine bulk substance (3.0 liter). Samples of the MVS crude bulk virus fluid were taken for testing of: Sterility (direct method), bacteriostasis and fungistasis, in vitro *mycoplasma* testing (agar cultivable and non-cultivable), tissue culture safety testing (GP-V810.2), in vitro *mycobacterium* testing, inapparent viruses, PBERT, potency.

MVS characterization: In addition, genetic identity was confirmed by sequencing of viral antigenomic cDNA from the NP gene through the L gene region to confirm identity.

Example 3: Comparative Studies Between PIV5 Vectored Control and CPI-RSV-F Vaccine Candidates in BALB/c Mice Materials and Methods The objective of the two mice studies (CHD03 and CHD04) in this report was to compare the immunogenicity and protective efficacy of two RSV vaccine candidates: W3AΔSH-RSV-F and CPI-RSV-F, in the BALB/c mouse model. In addition, two other vaccine candidates: W3A-RSV-F (SH-HN), and CPIΔSH-RSV-F were included in the studies. Antibody titers were measured by RSV F specific ELISA assay and cellular immune responses were measure by ELISPOT assay. The protection of vaccinated mice against wild type RSV strain challenge infection in the lower respiratory tract was determined by plaque assay of lung homogenates (Table 8).

TABLE 8

Summary of W3AΔSH-RSV-F and CPI-RSV-F data in CHD03 and CHD04 studies.

| Group | Test Articles | Number of mice | | Anti-F antibody titer (reciprocal dilution in $Log_{10}$/mL) 27 dpi | | IFN-γ secreting cells (per $10^6$ splenocytes) 27 dpi | | RSV titer in lung ($Log_{10}$PFU/g) 4 dpc | |
|---|---|---|---|---|---|---|---|---|---|
| | | CHD03 | CHD04 | CHD03 | CHD04 | CHD03 | CHD04 | CHD03 | CHD04 |
| A-C | PBS (Negative Control) | 15 | 15 | 1.3 | 1.3 | 3 | 0 | 3.21 | 3.33 |
| D-F | RSV_rA2 (Positive Control) | 15 | 15 | 2.9 | 3.3 | 10 | 10 | 1.39 | 1.32 |
| J-L | W3AΔSH-RSV-F; $10^5$ PFU. | 15 | 15 | 3.1 | 3.4 | 28 | 35 | 1.35 | 1.37 |
| M-O | CPI-RSV-F; $10^5$ PFU. | 15 | 15 | 3.0 | 3.2 | 23 | 48 | 1.48 | 1.40 |

dpi = days post immunization; dpc = days post challenge

The vaccine bulk substance was clarified by centrifugation at 1,500 rpm for 10 min at 2-8° C. resulting in 1.2 L followed by filtration through a 0.45 μM PES filter unit from Thermo Fisher resulting in 1.2 L. The clarified and filtered vaccine bulk substance is immediately formulated with 10× SPG to stabilize the virus prior to fill. There is no hold of the vaccine bulk substance before formulation and fill.

During the virus production process, control harvest fluid was prepared using uninfected Vero cells from the same production lot. The control fluids were stored at −60° C. or below. The production control fluid was harvested and tested for the Bacteriostasis and Fungistasis Bulk Product (Direct Method), Sterility, Detection and Quantitation of Residual Vero DNA and Determination of Endotoxin Levels (LAL).

Vaccine drug product manufacture (formulation and fill)/MVS: The filtered viruses were stabilized by formulation with 10% 10× SPG buffer and dispensed using a calibrated repeater pipette in 1 mL volumes into 2 mL cryovials to make the MVS stock/Vaccine Product (total 1281 vials, 1 mL per vial). The dispensed MVS/Vaccine product was flash frozen in dry ice/methanol bath and stored at −60° C. or below.

Clinical lot material: For the proposed initial Phase 1 trial, the Master Viral Seed (MVS), Lot #CPI-RSV-F (CPI-RSV-F-210519PQ10MVS DOM:26 Aug. 2021), is used as the vaccine drug product.

The critical materials and reagents used are listed in Table 9. The viruses used in the experiment are listed in Table 10.

TABLE 9

Critical Materials and Reagents

| Item | Source |
|---|---|
| Tissue homogenate samples | Biao He Lab, University of Georgia |
| Vero cells | ATCC, Cat#CCL-81 |
| Human anti-RSV-F mAb (Palivizumab) | MedImmune/AstraZeneca |
| Goat anti-human IgG H&L-HRP | Novex, Cat#A18811 |
| AEC Peroxide Substrate Kit | Vector, Cat#SK-4200 |
| RSV F protein | SinoBiological, 11049-V08B lot LC120C2910 |
| RSV F Peptide (85-93) | Lot#150909SP |
| ELISPOT Mouse IFN-γ Set | BD, Cat#551083 |
| ELISPOT AEC Substrate Set | BD, Cat#551951 |

TABLE 10

| Viruses | | | |
|---|---|---|---|
| Item | Lot | Titer (PFU/mL) | Source |
| RSV_rA2 strain | 190204AB | $7.6 \times 10^6$ | Biao He Lab, UGA |
| control | 181204CHD | $2.3 \times 10^7$ | Biao He Lab, UGA |
| control | 181204CHD | $1.9 \times 10^7$ | Biao He Lab, UGA |
| CPI-RSV-F | 170501SP | $2.1 \times 10^6$ | Biao He Lab, UGA |
| CPIΔSH-RSV-F | 170501SP | $1.7 \times 10^7$ | Biao He Lab, UGA |

All viruses were diluted down to $2\times10^6$ PFU/mL with 1×PBS prior to vaccination. RSV_rA2 stock was not diluted prior to challenge.

Experimental groups applicable to the ELISA, ELISPOT, and plaque assay tests are summarized in Table 11 and 12.

TABLE 11

| Dosing groups and testing CHD03. | | | | | | |
|---|---|---|---|---|---|---|
| Group | Dose Level | Number of Mice | Dosing Day | ELISPOT ELISA Day | Challenge Day | Necropsy Day |
| A-C | Negative Control: PBS | 15 | Day 0 | Day 27 | Day 35 | Day 39 |
| D-F | Positive control: RSV_rA2; $10^5$ PFU | 15 | Day 0 | Day 27 | Day 35 | Day 39 |
| G-I | W3A-RSV-F; $10^5$ PFU | 15 | Day 0 | Day 27 | Day 35 | Day 39 |
| J-L | W3AΔSH-RSV-F; $10^5$ PFU | 15 | Day 0 | Day 27 | Day 35 | Day 39 |
| M-O | CPI-RSV-F; $10^5$ PFU | 15 | Day 0 | Day 27 | Day 35 | Day 39 |
| P-R | CPIΔSH-RSV-F; $10^5$ PFU | 15 | Day 0 | Day 27 | Day 35 | Day 39 |

TABLE 12

| Dosing groups and testing CHD04. | | | | | | |
|---|---|---|---|---|---|---|
| Group | Dose Level | Number of Mice | Dosing Day | ELISPOT ELISA Day | Challenge Day | Necropsy Day |
| A-C | Negative Control: PBS | 15 | Day 0 | Day 27 | Day 35 | Day 39 |
| D-F | Positive control: RSV_rA2; $10^5$ PFU | 15 | Day 0 | Day 27 | Day 35 | Day 39 |
| G-I | W3A-RSV-F; $10^5$ PFU | 15 | Day 0 | Day 27 | Day 35 | Day 39 |
| J-L | W3AΔSH-RSV-F; $10^5$ PFU | 15 | Day 0 | Day 27 | Day 35 | Day 39 |
| M-O | CPI-RSV-F; $10^5$ PFU | 15 | Day 0 | Day 27 | Day 35 | Day 39 |
| P-R | CPIΔSH-RSV-F; $10^5$ PFU | 15 | Day 0 | Day 27 | Day 35 | Day 39 |

Immunization of mice: Six-to-eight week old female BALB/c mice were anesthetized by intraperitoneal injection of 250 µL of 2, 2, 2-tribromoethanol in tert-amyl alcohol (Avertin). Immunization was performed by intranasal administration of $10^5$ PFU of each vaccine candidate plus RSV_rA2 positive control in a 50 µL (25 µL per nostril) volume. Negative controls were treated intranasally with 50 µL (25 µL per nostril) of PBS. The RSV_rA2 positive control was used to mimic a natural RSV infection prior to vaccination. All animal experiments were performed according to the protocols approved by the Institutional Animal Care and Use Committee at the University of Georgia.

Figure 8:
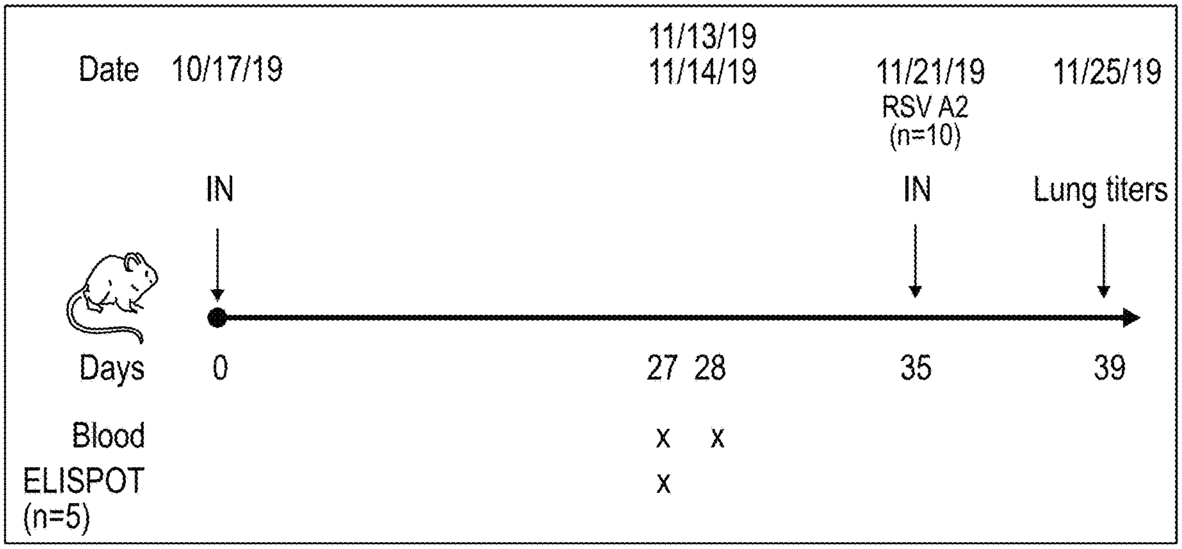
FIG. 8 shows an illustration of the CHD04 experimental timeline.

Twenty-seven days (mice in Groups A, D, G, J, M, P for CHD03 and Groups A, E, G, K, M, P for CHD04) or 28 days (Groups B, C, E, F, H, I, K, L, N, O, Q, R for CHD03 and Groups B, C, D, F, H, I, J, L, N, O, Q, R for CHD04) post-immunization, blood was collected via cheek bleed for serological analysis. Spleens from mice in cages A, D, G, J, M, P for CHD03 and cages A, E, G, K, M, P for CHD04 were also collected 27 days post-immunization to perform ELISPOT assays. Thirty-five days post-immunization, mice were anesthetized by intraperitoneal injection of 250 µL of Avertin and Groups B, C, E, F, H, I, K, L, N, O, Q, R for CHD03 and Groups B, C, D, F, H, I, J, L, N, O, Q, R for CHD04 were challenged intranasally with $3.8\times10^5$ PFU of RSV A2 in a 50 μL (25 μL per nostril) volume. After challenge, mice were continued to be house together per their vaccination group. Four days later, lungs were collected from 7-10 mice per group to assess viral burden by performing plaque assays on lung homogenates. Experimental timelines are shown in FIGS. 7 and 8.

Anti-F ELISA Assay: Anti-F antibody titer was determined by anti-F ELISA assay per CVL SOP-049. The Immulon 2HB 96 well plates were coated with 50 μL/well of F protein of RSV at 12.5 ng/mL overnight. The serum samples were prediluted by 10-fold followed by 3-fold serial dilution and added to F protein-coated plate (50 μL/well) at room temperature for 1 hour. After plate wash, 50 μL/well goat anti-mouse IgG HRP conjugated antibody at 1:1250 dilution was added and incubated at room temperature for 1 hour. Following wash, 100 μL/well of SureBlue Reserve TMB Microwell Peroxidase Substrate was added for 3-5 min and the reaction was stopped by adding 100 μL/well of IN HCl. The plates were read with plate reader (SpectraMax iD3 Multi-mode Microplate Reader) at 450 nm immediately after adding HCL. Samples that exceed $OD_{450}$ cutoff value of 0.20 are considered positive in at least two consecutive dilutions. Antibody titer is defined as the highest reciprocal dilution with positive signal. This assay was performed at Blue Lake Biotechnology in Los Gatos, CA.

Enzyme-Linked ImmunoSpot Assay (ELISPOT): Levels of IFN-γ secreting cells were measured by ELISPOT assay using BD™ ELISPOT Mouse IFN-γ Set. BD™ ELISPOT plates were coated with purified anti-mouse IFN-γ antibody 24 hours prior to performing assay. Mouse spleens (n=5, per group) were collected 27 days post-immunization and put into 15 mL conical tubes containing 5 mL of HBSS. Splenocytes were prepared by pressing spleens through a 70 μM cell strainer, incubating them with ACK lysis buffer, washing them with HBSS, and re-suspending in complete tumor medium (CTM) to a concentration of $5\times10^6$ cells/mL. The capture antibody solution was removed from the plates and then the plates were washed 5-6 times with PBS. The plates were then blocked with CTM for 90 min. The blocking solution was discarded, and 0.1 μg of RSV F peptide (85-93) in 50 μL of CTM were added to the wells. Next, 50 μL of splenocytes ($2.5\times10^5$ cells/well) were added to plates and incubated at 37° C., 5% $CO_2$, for 48 h. The spots were immunostained according to the BD™ ELISPOT Set instruction manual and counted using an ImmunoSpot® analyzer (Cell Technology Limited, CTL). Results were presented as mean number of IFN-γ secreting cells per $10^6$ splenocytes. This assay was performed at the University of Georgia in Athens, GA.

Plaque Assay: RSV viral titer in lung homogenate was performed in Vero cells by plaque assay. Briefly, mouse lungs were collected in gentleMACS M tubes containing 3 mL of Opti-MEM with 1% BSA and kept on ice. The lungs were weighted and then homogenized using the Protein_01 program of a gentleMACS Dissociator at 4° C. and then centrifuged for 10 min at 3000×g. Supernatant was used to perform 3-fold serial dilutions at a total volume of 0.6 mL from undiluted to 1:27. Vero cells in a 24-well plate were infected with 100 μL of each dilution in triplicate. After 1 hour adsorption at 37° C., the inoculum was removed, plates were washed 1× with PBS, and approximately 1 mL of methyl cellulose was added to each well. After a 7-day incubation, the methyl cellulose was removed, and cells were fixed with approximately 500 μL of 60% Acetone/40% Methanol for 20 minutes. Cell were washed and then blocked with 400 μL/well of blotto for 30 minutes. After blocking, cells were incubated for 1 hour at room temperature with 200 μL/well of human anti-RSV-F antibody (Palivizumab, 1 mg/mL) diluted 1:1000. After plate wash, 200 μL/well goat anti-human IgG HRP conjugated antibody at 1:1000 dilution was added and incubated at room temperature for 1 hour. Following wash, 200 L/well of AEC substrate was added for 30 minutes at room temperature. Viral titer was determined by counting plaques at the dilution where range of plaque counting was between 10-100. Results were reported as PFU/g of lung. This assay was performed at the University of Georgia in Athens, GA.

Results

Figure 9A:
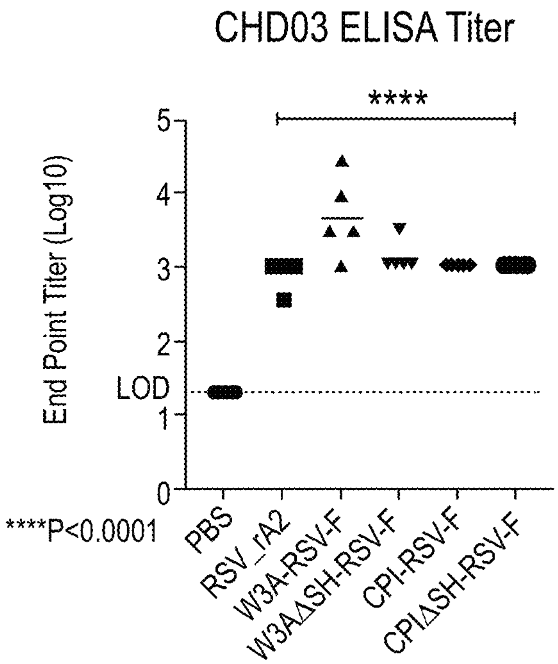
FIGS. 9A-9B show CHD03 (FIG. 9A) and CHD04 (FIG. 9B) RSV-F serum antibody titers. Naïve BALB/c mice were treated with PBS or immunized intranasally with $10^5$ PFU of PIV5-RSV-F, PIV5ΔSH-RSV-F, CPI-RSV-F, CPIΔSH-RSV-F, or RSV_rA2. Sera were collected at 4 weeks post-immunization. RSV-F-specific IgG antibody endpoint titers were determined by ELISA (N=5). Horizontal lines represent the geometric mean antibody titer of each group. Statistical significance was determined by ANOVA and Dunnett's multiple comparison tests. **** $P<0.0001$, significance between PBS and vaccine groups. LOD, limit of detection.
Figure 9B:
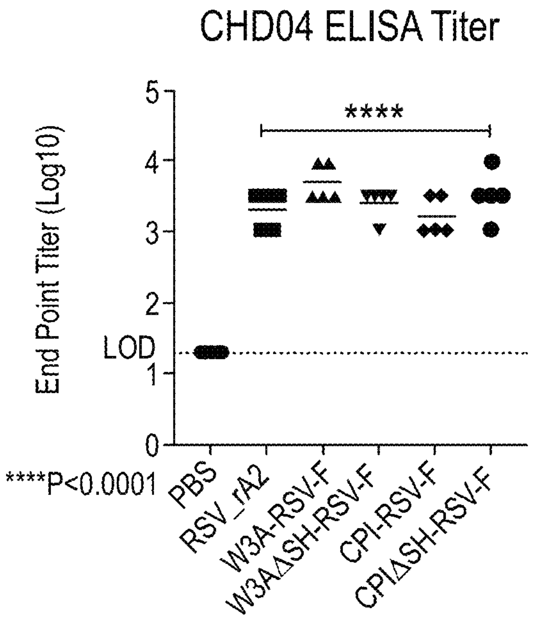

Anti-F antibody titer: Anti-F antibody titers were obtained from animals in Groups A, D, G, J, M, P for CHD03 and Groups A, E, G, K, M, P for CHD04 at Day 27 post vaccination and results are shown in FIG. 9A-9B. Overall, anti-F antibody titers were significantly higher in all vaccinated groups compared to the PBS control group. Anti-F antibody titers in Group J (W3AΔSH-RSV-F) and Group M (CPI-RSV-F) in CHD03 and Group K (W3AΔSH-RSV-F) and Group M (CPI-RSV-F) in CHD04, were very similar. In CHD03, W3AΔSH-RSV-F had a geometric mean titer of 3.1 $Log_{10}$/mL while CPI-RSV-F had a geometric mean titer of 3.0 $Log_{10}$/mL. In CHD04, W3AΔSH-RSV-F had a geometric mean titer of 3.4 $Log_{10}$/mL, while CPI-RSV-F had a geometric mean titer of 3.2 $Log_{10}$/mL. W3A-RSV-F in both CHD03 and CHD04 had the highest anti-F antibody titer with a geometric mean titer of 3.7 $Log_{10}$/mL in both experiments. W3AΔSH-RSV-F and CPI-RSV-F groups had similar anti-F antibody titers to RSV_rA2 positive control group in both CHD03 and CHD04. CPIΔSH-RSV-F also elicited comparable serum antibody levels in both studies.

These results indicate that both W3AΔSH-RSV-F and CPI-RSV-F as well as other two vaccine candidates elicit similar levels of anti-F antibodies in BALB/c mice at the dose of $1\times10^5$ PFU administered intranasally.

F-specific cellular immune responses: Cellular immune responses induced by the vaccine candidates were measured by levels of IFN-γ secreting cells. In CHD03, Group J (W3AΔSH-RSV-F) and Group M (CPI-RSV-F) had higher levels of IFN-γ secreting cells, with Group J having a geometric mean of 28 IFN-γ secreting cells per $10^6$ splenocytes and Group M having a geometric mean of 23 IFN-γ secreting cells per $10^6$ splenocytes. These values were not statistically significant from the PBS group, but they were also not statistically significant from each other. Group G (W3A-RSV-F) had the highest value compared to the PBS group, with a geometric mean of 57 IFN-γ secreting cells per $10^6$ splenocytes, which was not significantly different from the other groups. Values from W3AΔSH-RSV-F and CPI-RSV-F groups are similar to the levels of IFN-γ secreting cells seen in RSV_rA2 group.

In CHD04, Group K (W3AΔSH-RSV-F) and Group M (CPI-RSV-F) had the highest levels of IFN-γ secreting cells, with Group K having a geometric mean of 35 IFN-γ secreting cells per $10^6$ splenocytes and Group M of 48 cells per $10^6$ splenocytes. These values are statistically significant from the PBS control group, but they were not statistically significant from each other. Out of both vaccine groups of interest, only CPI-RSV-F group had a significantly higher amount of IFN-γ secreting cells than RSV_rA2 positive control group. W3A-RSV-F and CPIΔSH-RSV-F also elicited F specific cellular responses.

Figure 10A:
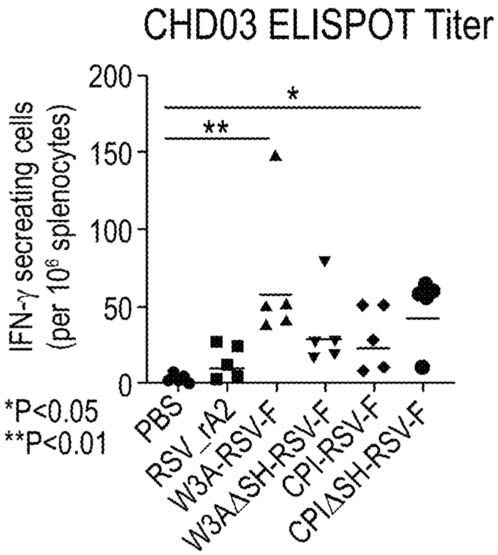
FIGS. 10A-10B show CHD03 and CHD04 RSV-F ELISPOT titers. Naïve BALB/c mice were treated with PBS or immunized intranasally with $10^5$ PFU of PIV5-RSV-F, PIV5ΔSH-RSV-F, CPI-RSV-F, CPIΔSH-RSV-F, or RSV_rA2. Splenocytes were harvested and stimulated with an RSV F peptide. Results are presented as number of IFN-γ-secreting cells per $10^6$ splenocytes (N=5). Horizontal lines in represent the geometric mean ELISPOT titer. Statistical significance was determined by ANOVA and Dunnett's multiple comparison tests. * $P<0.05$,  $P<0.01$, * $P<0.001$, significance between PBS and vaccine groups.
Figure 10B:
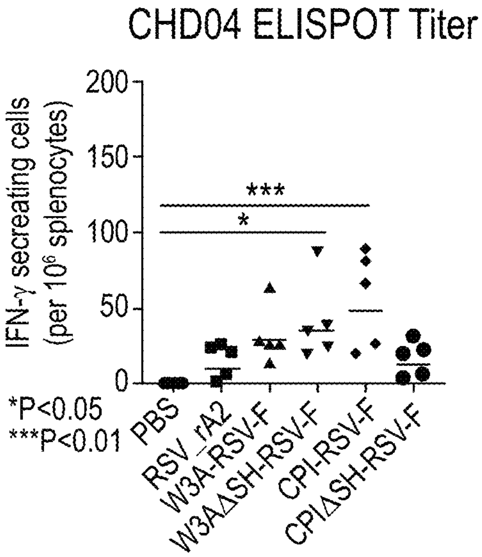

FIGS. 10A-10B indicate that both W3AΔSH-RSV-F and CPI-RSV-F vaccine candidates of interest as well as the other two vaccine candidates (W3A-RSV-F and CPIΔSH—RSV-F) elicit similar levels of cell-mediated immune responses in BALB/c mice.

RSV challenge virus lung titers: The four RSV vaccine candidates were evaluated for their protection against RSV_rA2 virus challenge infection in the lower respiratory tract of mice. Overall, all vaccine groups had significantly lower lung viral titers compared to the PBS control in both CHD03 (FIG. 11A) and CHD04 (FIG. 11B), which had geometric mean titers of 3.21 $Log_{10}$ PFU/g and 3.33 $Log_{10}$ PFU/g respectively. In CHD03, RSV challenge virus titers in Groups K and L (W3AΔSH-RSV-F), was 1.35 $Log_{10}$ PFU/g, while Groups N and O (CPI-RSV-F) had a geometric mean titer of 1.48 $Log_{10}$ PFU/g. These values are not statistically significant from each other. The other vaccine candidates tested (W3A-RSV-F and CPIΔSH-RSV-F) had geometric mean titers of 1.35 $Log_{10}$ PFU/g and 1.40 $Log_{10}$ PFU/g, respectively. These values are also significantly lower than the PBS control. In CHD04, Groups J and L (W3AΔSH-RSV-F) had a geometric mean titer of 1.37 $Log_{10}$ PFU/g, while Groups N and O (CPI-RSV-F) had a geometric mean titer of 1.40 $Log_{10}$ PFU/g. Similar to CHD03, these values are not statistically significant from each other, but are significantly lower than the PBS control group. The W3A-RSV-F and CPIΔSH-RSV-F vaccine candidates had geometric mean titers of 1.35 $Log_{10}$ PFU/g and 1.40 $Log_{10}$ PFU/g, respectively. These values are the same as experiment CHD03 and are also significantly lower than the PBS control group. Lung RSV viral titers in all vaccine groups were similar to that seen in RSV_rA2 positive control group in both CHD03 and CHD04.

Figure 11A:
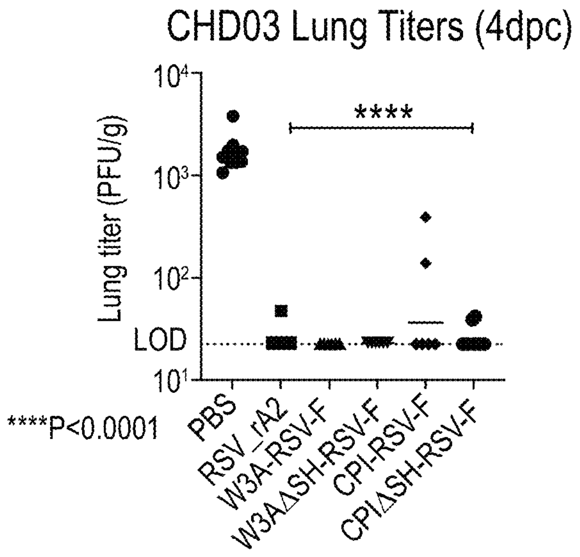
FIGS. 11A-11B show CHD03 (FIG. 11A) and CHDO4 (FIG. 11B) lung titers.
Figure 11B:
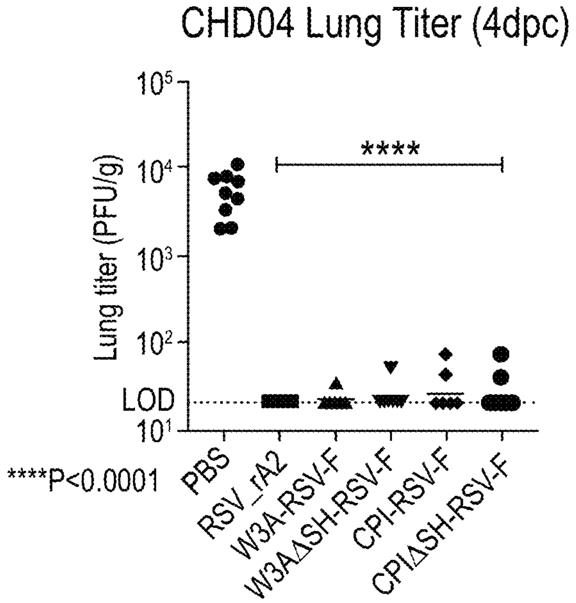

FIGS. 11A-11B indicate that both W3AΔSH-RSV-F and CPI-RSV-F vaccine candidates as well as the other two vaccine candidates protected against RSV challenge virus infection in the lower respiratory tract of BALB/c mice.

Example 4: Virus Replication in the Upper and Lower Respiratory Tracts of Cotton Rats Methods and Materials Animals: Fifty five (55) inbred, 6-8 weeks-old, *Sigmodon hispidus* female and male cotton rats (source: Sigmovir Biosystems, Inc., Rockville MD) were maintained and handled under veterinary supervision in accordance with the National Institutes of Health guidelines and Sigmovir Institutional Animal Care and Use Committee's approved animal study protocol (IACUC Protocol #15). Each group of animals included 3 females (the first three animals in each group) and 2 males (the last 2 animals in each group). Cotton rats were housed in clear polycarbonate cages and provided with standard rodent chow (Harlan #7004) and tap water ad lib.

Virus: Respiratory Syncytial Virus strain A/A2 (RSV A/A2) (ATCC, Manassas, VA) was propagated in HEp-2 cells after serial plaque-purification to reduce defective-interfering particles. A pool of virus designated as hRSV A/A2 Lot #092215 SSM containing approximately $3.0\times10^8$ pfu/mL in sucrose stabilizing media was used in this in vivo experiment. This stock of virus is stored at −80° C. and has been characterized in vivo in the cotton rat model and validated for upper and lower respiratory tract replication.

Procedure(s): Divide 55 female and male young adult cotton rats (6-8 weeks of age) into 9 groups of 5 animals each (3 females, 2 males), one group of 4 animals (2 females, 2 males), and 2 groups of 3 animals each (2 females and 1 male). Prebleed for serum collection and ear-tag all animals. Immunize or infect animals with 0.1 ml of preparation as indicated in Table 13 below.

TABLE 13

Immunization or Infection of Animals.

| Group | N | Treatment | TA Dose (per rat) | Immunization days | Route | Challenge (pfu/rat) | Day of harvest (post-RSV challenge) |
|---|---|---|---|---|---|---|---|
| A | 4 | PBS (Mock) | n/a | 0, 28 | IM | PBS | 5 |
| B | 5 | PBS (Mock) | n/a | 0, 28 | IN | RSV 5.0 Log10 | 5 |
| C | 5 | FI-RSV Lot#100 | 1:100 in PBS | 0, 28 | IM | RSV 5.0 Log10 | 5 |
| D | 5 | RSV/A2 Live | 5.0 Log10 | 0 only | IN | RSV 5.0 Log10 | 5 |
| E | 5 | CPI-RSV-F | $10^4$ PFU | 0 only | IN | RSV 5.0 Log10 | 5 |
| F | 5 | CPI-RSV-F | $10^5$ PFU | 0 only | IN | RSV 5.0 Log10 | 5 |
| G | 5 | CPI-RSV-F | $10^6$ PFU | 0 only | IN | RSV 5.0 Log10 | 5 |
| H | 5 | W3AΔSH-RSV-F | $10^4$ PFU | 0 only | IN | RSV 5.0 Log10 | 5 |
| I | 5 | W3AΔSH-RSV-F | $10^5$ PFU | 0 only | IN | RSV 5.0 Log10 | 5 |
| J | 5 | W3AΔSH-RSV-F | $10^6$ PFU | 0 only | IN | RSV 5.0 Log10 | 5 |
| K | 3 | CPI-RSV-F | $10^6$ PFU | 0 only | IN | Harvest on day 4 post- | |
| L | 3 | W3AΔSH-RSV-F | $10^6$ PFU | 0 only | IN | PIV dosing | |

Sacrifice animals in groups K and L. Harvest the nasal tissue and homogenize in 3 ml of HBSS supplemented with 10% SPG for viral titrations. Harvest the lung en bloc and tri-sect for viral titration (left section, homogenize in 3 ml of HBSS supplemented with 10% SPG), histopathology (right section, inflate with 10% neutral buffered formalin), and qPCR (lingular lobe, flash frozen in liquid nitrogen).

Eyebleed all animals for serum collection. Boost animals in groups A, B, and C with 0.1 ml of preparation as indicated in the table above.

Eyebleed all animals for serum collection. Mock challenge intranasally (IN) group A with 0.1 ml of PBS (pH 7.4). Challenge in animals in groups B thru J with 0.1 ml of RSV/A2 (Lot #092215 SSM) at $10^5$ PFU per animal. Perform back titration on the challenge virus to confirm challenge dose.

Sacrifice all animals. Harvest the nasal tissue and homogenize in 3 ml of HBSS supplemented with 10% SPG for viral titrations. Harvest the lung en bloc and tri-sect for viral titration (left section, homogenize in 3 ml of HBSS supplemented with 10% SPG), histopathology (right section, inflate with 10% neutral buffered formalin), and qPCR (lingular lobe, flash frozen in liquid nitrogen). The animal sacrifice groups are shown in Table 14 and sample collections are shown in Table 15.

TABLE 14

Animal Sacrifice Groups.

| Groups | Animal #s |
|---|---|
| A | 124831-124834 |
| B | 124835-124839 |
| C | 124840-124844 |
| D | 124845-124849 |
| E | 124850-124854 |
| F | 124855-124859 |
| G | 124860-124864 |
| H | 124865-124869 |
| I | 124870-124874 |
| J | 124875-124879 |
| K | 124880-124882 |
| L | 124883-124885 |

TABLE 15

Sample Collections.

| Sample Collections | Day(s) of collection | # of Sets |
|---|---|---|
| Lung and nose homogenates | 4 (GrK-L) | 3* |
| Lung and nose homogenates | 54 (GrA-J) | 2 |
| Lung histology | 4 (GrK-L); 54 (GrA-J) | 1 |
| Serum | 0, 28, and 49 | 2 |
| Lung total RNA | 4 (GrK-L); 54 (GrA-J) | 1 |

Table 16 shows the endpoint assays protocol outline.

TABLE 16

Endpoint Assays Protocol

| Endpoint Assays | Samples | Storage |
|---|---|---|
| RSV viral titrations (GrA-J) | Lung homogenates<br>Nose homogenates | −80° C. |
| PIV viral titrations (GrK-L) | Lung homogenates<br>Nose homogenates | −80° C. |
| Pulmonary Histopathology (GrA-K) | H&E lung slides | RT |
| RSV Neutralizing Ab (GrA-J) (RSV/A2) (d 0, 28, and 49) | Serum | −20° C. |
| RSV/A2 serum IgG ELISA (GrA-J) (d 0, 28, 49) (4-dilution format) | Serum | −20° C. |
| qPCR (GrA-J) RSV/A2 NS-1 gene; IL-4, IL-2, IFN-γ | Lung RNA | −80° C. |
| qPCR PIV (GrK, L) | Lung RNA | −80° C. |

Lung and nose RSV viral titration: Lung and nose homogenates are clarified by centrifugation and diluted in EMEM. Confluent HEp-2 monolayers are infected in duplicates with diluted homogenates in 24 well plates. After one hour incubation at 37° C. in a 5% $CO_2$ incubator, the wells are overlayed with 0.75% Methylcellulose medium. After 4 days of incubation, the overlay is removed and the cells are fixed with 0.1% crystal violet stain for one hour and then rinsed and air dried. Plaques are counted and virus titer is expressed as plaque forming units per gram of tissue. Viral titers are calculated as geometric mean #standard error for all animals in a group at a given time.

Pulmonary histopathology: Lungs are dissected and inflated with 10% neutral buffered formalin to their normal volume, and then immersed in the same fixative solution. Following fixation, the lungs are embedded in paraffin, sectioned and stained with hematoxylin and eosin (H&E). Four parameters of pulmonary inflammation are evaluated: peribronchiolitis (inflammatory cell infiltration around the bronchioles), perivasculitis (inflammatory cell infiltration around the small blood vessels), interstitial pneumonia (inflammatory cell infiltration and thickening of alveolar walls), and alveolitis (cells within the alveolar spaces). Slides are scored blind on a 0-4 severity scale. The scores are subsequently converted to a 0-100% histopathology scale.

RSV neutralizing antibody assay (60% reduction) for preclinical studies: Heat inactivated sera samples are diluted 1:10 with EMEM and serially diluted further 1:4. Diluted sera samples are incubated with RSV (25-50 PFU) for 1 hour at room temperature and inoculated in duplicates onto confluent HEp-2 monolayers in 24 well plates. After one hour incubation at 37° C. in a 5% CO2 incubator, the wells are overlayed with 0.75% Methylcellulose medium. After 4 days of incubation (6 days for RSV B), the overlay is removed and the cells are fixed with 0.1% crystal violet stain for one hour and then rinsed and air dried. The corresponding reciprocal neutralizing antibody titers are determined at the 60% reduction end-point of the virus control using a statistics program. The geometric means±standard error for all animals in a group at a given time are calculated.

RSV IgG ELISA for preclinical studies: Whole RSV inactivated with UV or purified F protein extracted from RSV-infected HEp-2 cells are diluted and coated onto 96 well ELISA plate overnight. The coating antigen is decanted and the plate is incubated in blocking solution for one hour at room temperature and subsequently washed. Diluted sera (1:500 in duplicates) along with the positive and negative controls are added to the wells and incubated at room temperature for one hour. After washing the plate, Rabbit anti Cotton Rat IgG (1:500) is added to all the wells and incubated for one hour at room temperature. This is followed by the incubation with Goat anti Rabbit IgG-HRP (1:6,000) for one hour at room temperature. At the end, TMB substrate is added to all the wells and incubated at room temperature for 15 minutes. TMB-Stop solution is added to all the wells and optical density at 450 nm is recorded. Geometric mean of the optical density ($OD_{450}$) is measured for all triplicate sera samples+standard error for all samples in a group per time-point.

Real-time PCR for preclinical studies: Total RNA is extracted from homogenized tissue or cells using the RNeasy purification kit (QIAGEN). One μg of total RNA is used to prepare cDNA using Super Script II RT (Invitrogen) and oligo dT primer (1 μl, Invitrogen). For the real-time PCR reactions the Bio-Rad iQ™ SYBR Green Supermix is used in a final volume of 25 μl, with final primer concentrations of 0.5 μM. Reactions are set up in duplicates in 96-well trays. Amplifications are performed on a Bio-Rad iCycler for 1 cycle of 95° C. for 3 min, followed by 40 cycles of 95° C. for 10 seconds(s), 60° C. for 10 s, and 72° C. for 15 s. The baseline cycles and cycle threshold (Ct) are calculated by the iQ5 software in the PCR Base Line Subtracted Curve Fit mode. Relative quantitation of DNA is applied to all samples. The standard curves are developed using serially diluted cDNA sample most enriched in the transcript of interest (e.g., lungs from 6 hours post RSV infection of FI-RSV-immunized animals or PIV5-specific control). The Ct values are plotted against $\log_{10}$ cDNA dilution factor. These curves are used to convert the Ct values obtained for different samples to relative expression units. These relative expression units are then normalized to the level of β-actin mRNA ("housekeeping gene") expressed in the corresponding sample. For animal studies, mRNA levels are expressed as the geometric mean±SEM for all animals in a group at a given time.

Results

Confirmation of the replication of vaccine viruses in the cotton rat model: To confirm replication of the PIV5-based vaccines in the respiratory tract of cotton rats, groups of 3 animals were inoculated with $10^6$ PFU of CPI-RSV-F or W3AΔSH-RSV-F intranasally and sacrificed four days later, with samples submitted for evaluation to Blue Lake Biotechnology (BLB). BLB conducted plaque assay on submitted samples. In brief, it was found that both candidate vaccine viruses replicated in the upper and lower respiratory track of cotton rats (Table 17). In CPI-RSV-F vaccinated animals, the vaccine virus replicated similarly in the upper (nose) and lower respiratory tract (lung), 3.9 and 3.5 LogioPFU/mL, respectively. W3AΔSH-RSV-F replicated at a higher titer in the upper respiratory tract (5.0 $Log_{10}$PFU/mL) compared to lower respiratory tract (2.2 LogioPFU/mL). W3AΔSH-RSV-F vaccine virus replicated to higher levels in the upper respiratory tract compared to CPI-RSV-F, but it replicated to lower levels in the lower respiratory tract compared to CPI-RSV-F. Overall, replication of both vaccine viruses in the cotton rat model was successfully confirmed (Table 17).

TABLE 17

Assessment of replication of CPI-RSV-F and W3AΔSH-RSV-F in the respiratory tract of cotton rats.

| Group | Animal ID | Tissue | Day | Titer ($Log_{10}$ PFU/mL) | Average titer ($Log_{10}$ PFU/mL) |
|---|---|---|---|---|---|
| Group K | 124880 | Nose | 4 | 3.7 | 3.9 |
| CPI-RSV-F | 124881 | Nose | 4 | 3.9 | |
| Day 4 | 124882 | Nose | 4 | 4.0 | |
| | 124880 | Lung | 4 | 3.8 | 3.5 |
| | 124881 | Lung | 4 | 3.3 | |
| | 124882 | Lung | 4 | 2.9 | |
| Group L | 124883 | Nose | 4 | 4.5 | 5.0 |
| W3AΔSH-RSV-F | 124884 | Nose | 4 | 4.9 | |
| Day 4 | 124885 | Nose | 4 | 5.2 | |
| | 124883 | Lung | 4 | 2.3 | 2.2 |
| | 124884 | Lung | 4 | 2.2 | |
| | 124885 | Lung | 4 | 1.7 | |

Animals were inoculated with $10^6$ PFU of CPI-RSV-F or W3AΔSH-RSV-F intranasally and sacrificed four days later. Lung and nose samples were collected and shipped to BLB for plaque assay.

Evaluation of Vaccines for Efficacy and Safety in the Cotton Rat Model of RSV a/A2 Infection.

Figure 12:
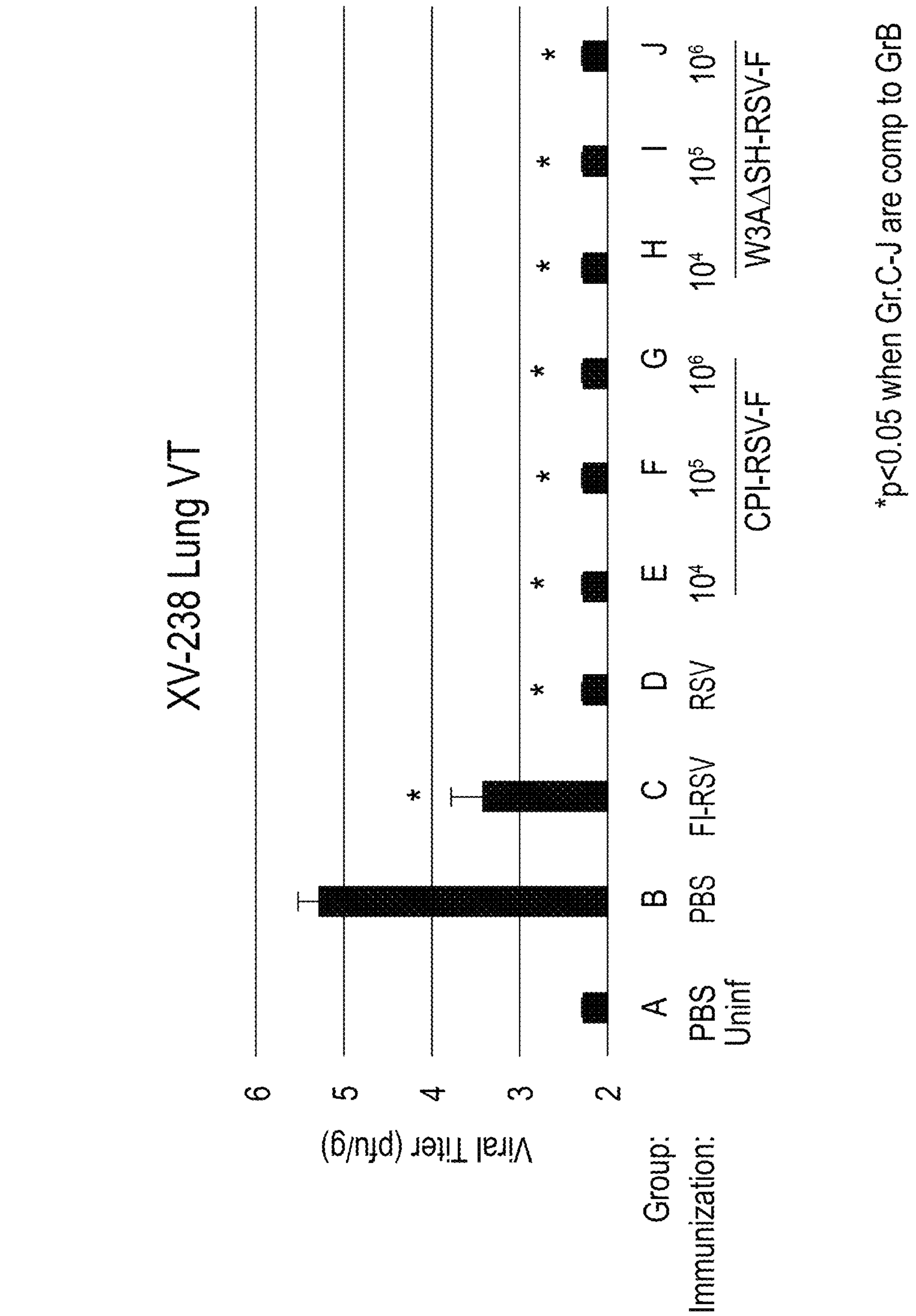
FIG. 12 shows a lung RSV challenge virus titer following RSV challenge.

Lung viral titers: RSV A/A2 load in the lungs of cotton rats was evaluated 5 days after intranasal RSV challenge (FIG. 12). RSV-infected animals mock-immunized with PBS (Group B) showed a titer of 5.3 $Log_{10}$ PFU/g virus in the lungs and were used for comparison to all other RSV-infected groups (Groups C-J). No virus was detectable in the lungs of animals infected with RSV twice (Group D). FI-RSV immunization (Group C) moderately, but significantly reduced lung RSV titer to 3.4 $Log_{10}$ PFU/g. Immunization with CPI-RSV-F at doses $10^4$, $\mathbf{10}^5$, or $10^6$ PFU (Groups E, F, and G, respectively) or with W3AΔSH-RSV-F at doses $10^4$, $\mathbf{10}^5$, or $10^6$ PFU (Groups H, I, and J, respectively) reduced RSV load to an undetectable level in all vaccinated animals.

Figure 13:
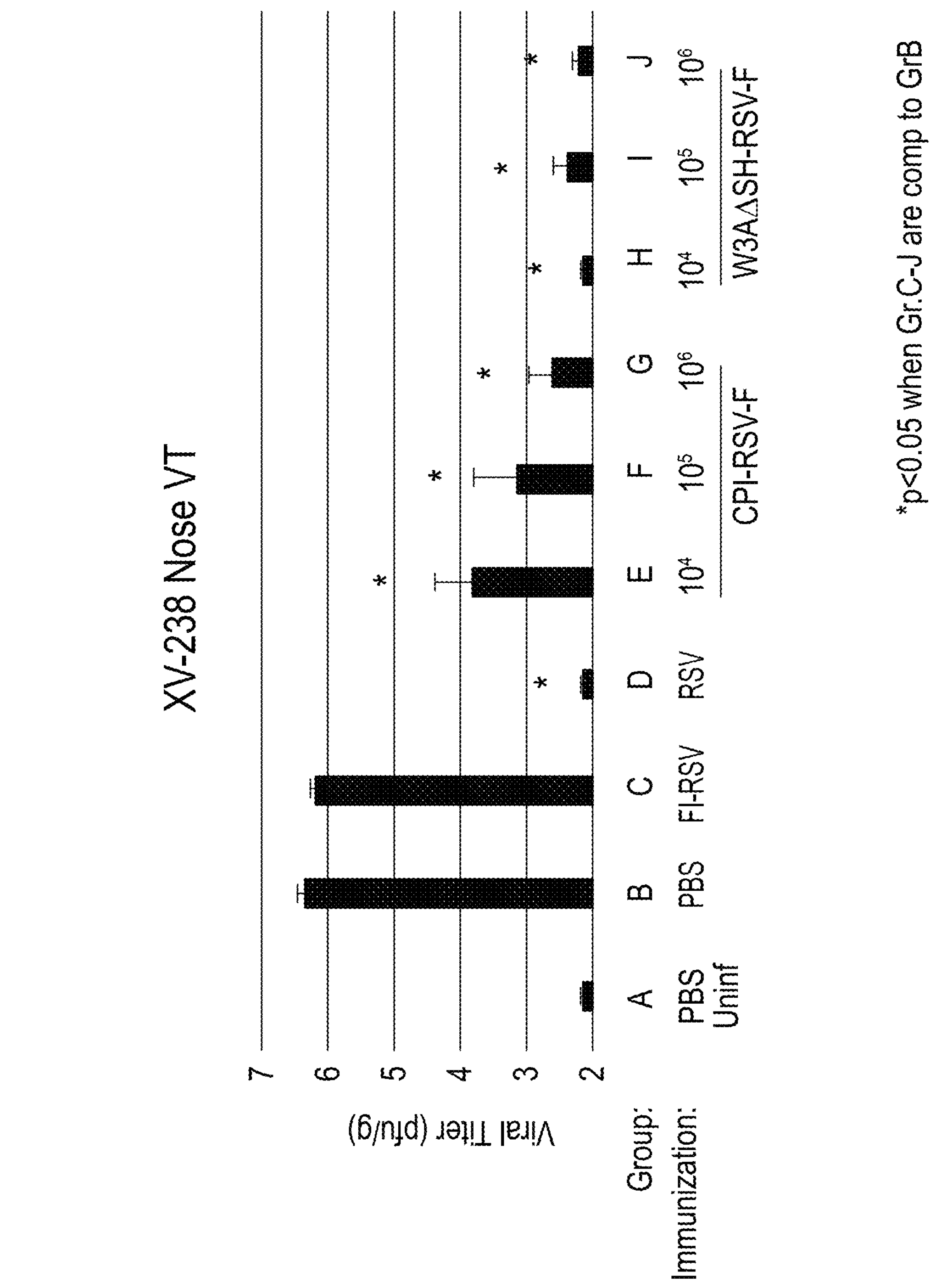
FIG. 13 shows a nasal RSV challenge virus titer following RSV challenge in nasal wash.

Nose viral titers: RSV A/A2 load in the nose of cotton rats was evaluated 5 days after intranasal RSV challenge (FIG. 13). RSV-infected animals mock-immunized with PBS (Group B) showed a titer of 6.19 $Log_{10}$ PFU/g virus in the nose and were used for comparison to all other RSV-infected groups (Groups C-J). No virus was detected in the nose of animals infected with RSV twice (Group D). FI-RSV immunization (Group C) had no effect on RSV load in the nose (6.02 $Log_{10}$ PFU/g). Immunization with CPI-RSV-F at doses of $10^4$, $\mathbf{10}^5$, or $10^6$ PFU resulted in the dose-dependent reduction in viral load in the nose: 3.65, 3.00, and 2.44 PFU/g in Groups E, F, and G, respectively. Immunization with W3AΔSH-RSV-F at all three doses tested (Groups H-J) reduced RSV replication in the nose to an almost undetectable level, with only single-digit numbers of plaques in some animals in each group (1, 3, and 1 animal in Groups H, I, and J, respectively, had between 1 and 5 plaques).

Figure 14:
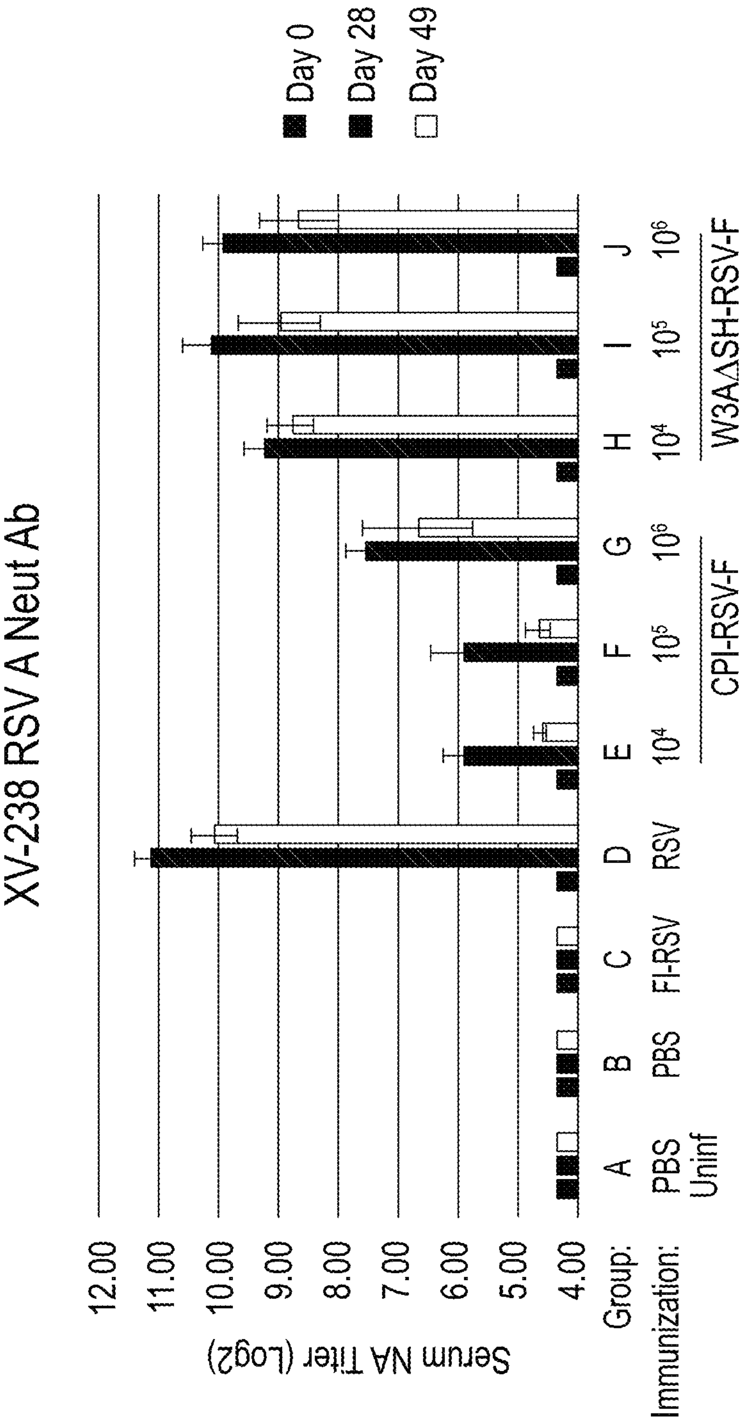
FIG. 14 shows RSV neutralizing antibody responses.

Serum RSV A/A2 Neutralizing Antibodies: Serum neutralizing antibodies against RSV A/A2 were measured in all animals prior to the start of experiment (day 0), 4 weeks after the first immunization (day 28), and three weeks later (day 49) (FIG. 14). Animals infected with RSV A/A2 (Group D) showed high titers of serum RSV A/A2 neutralizing antibodies four weeks after infection (day 28 data, 11.14 Log2), which remained elevated seven weeks after infection (day 49 data, 10.07 Log2). Immunization with CPI-RSV-F at doses of $10^4$, $\mathbf{10}^5$, or $10^6$ PFU (Groups E, F, and G, respectively) resulted in NA titers of 5.92, 5.87, and 7.55 on day 28.

Animals immunized with the highest dose of vaccine tested (Group G, $10^6$ PFU) retained elevated NA titer by day 49 (6.65 Log2), while NA levels in Groups E and F declined to 4.6 and 4.62 Log2, respectively, by that time. Immunization with W3AΔSH-RSV-F at $10^4$, $10^5$, or $10^6$ PFU (Groups H-J) resulted in NA titer of 9.24, 10.11, and 9.91 Log2 on day 28, respectively. The NA titer in these groups remained strongly elevated on day 49 (8.79, 8.97, 8.64 Log2, respectively). No other group of animals showed detectable neutralizing antibodies against RSV A/A2.

Figure 15:
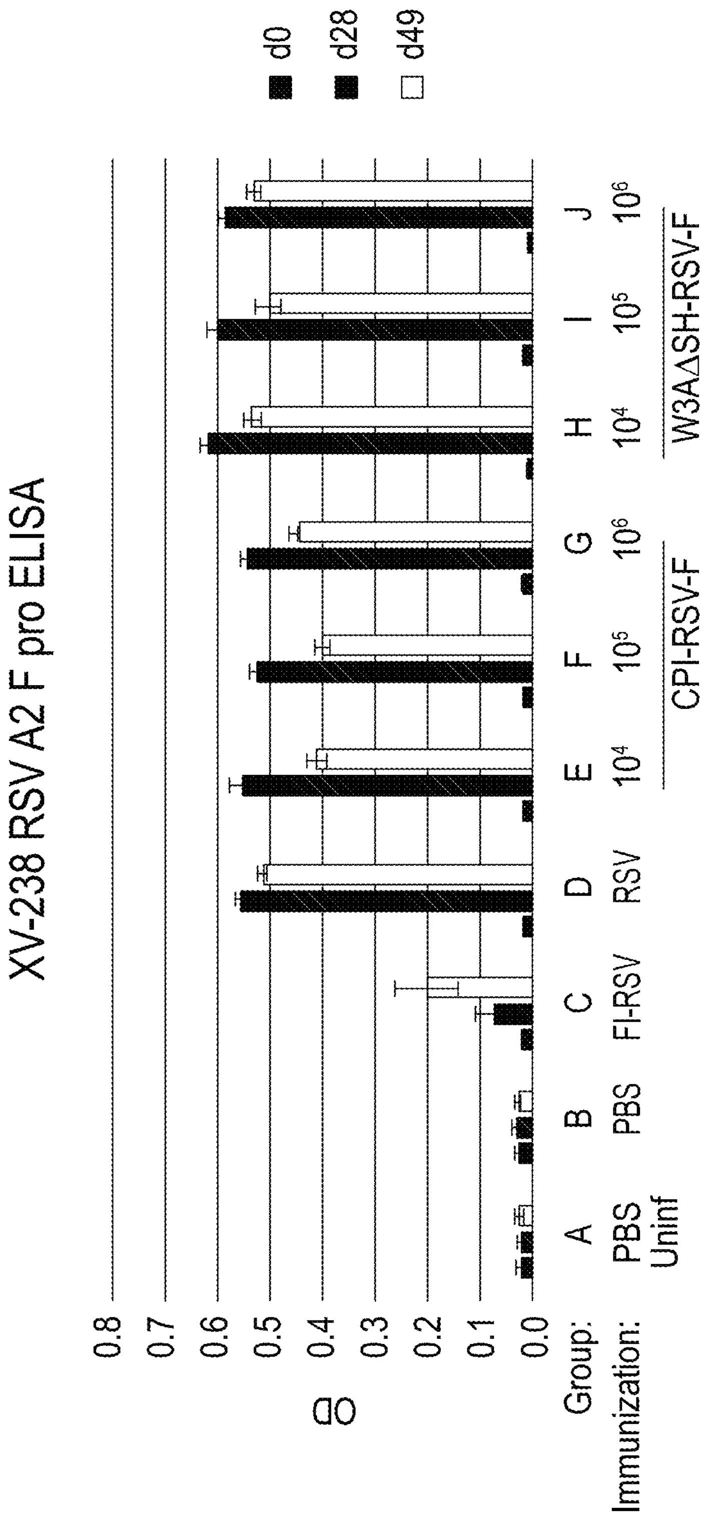
FIG. 15 shows anti-RSV F protein IgG antibody responses by ELISA.
Figure 16A:
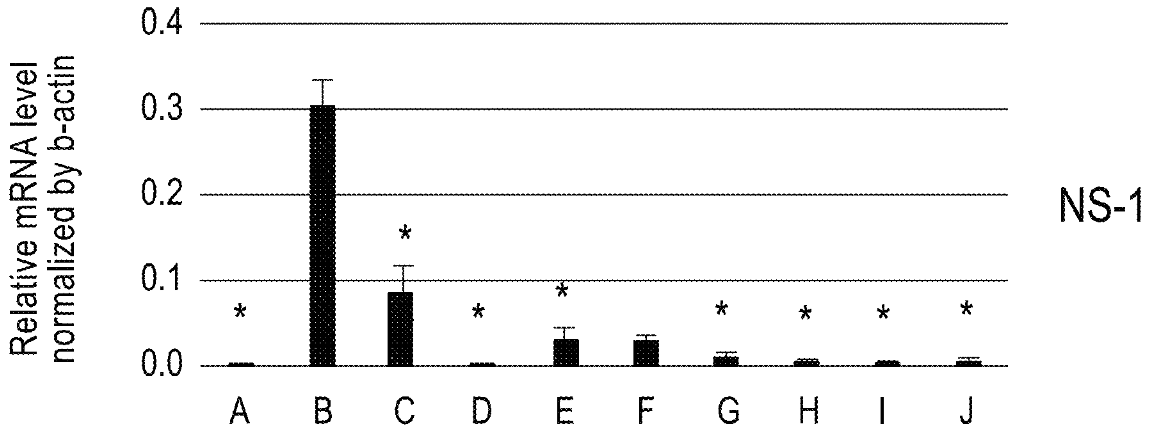
FIGS. 16A-16D are bar graphs showing the expression of RSV NS1, IL-4, IL-2, and IFN-γ mRNA.
Figure 16B:
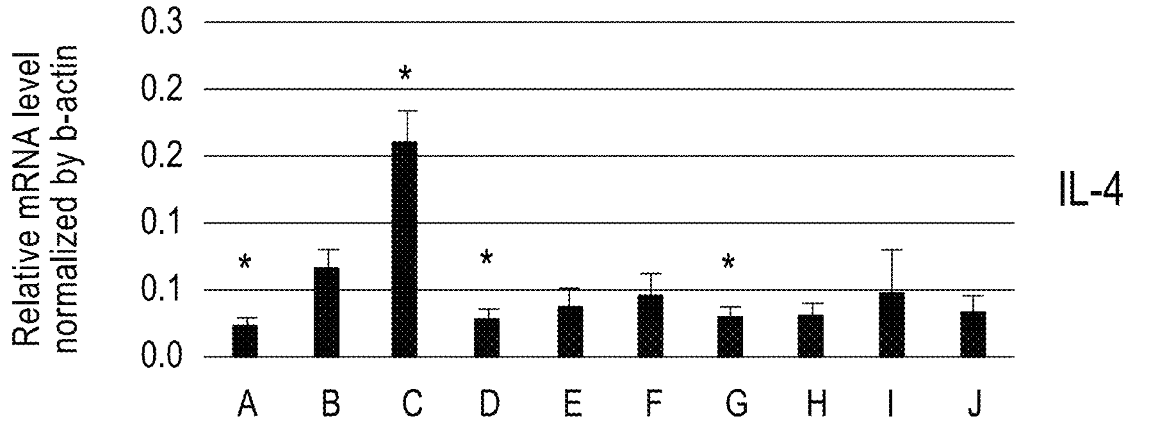
Figure 16C:
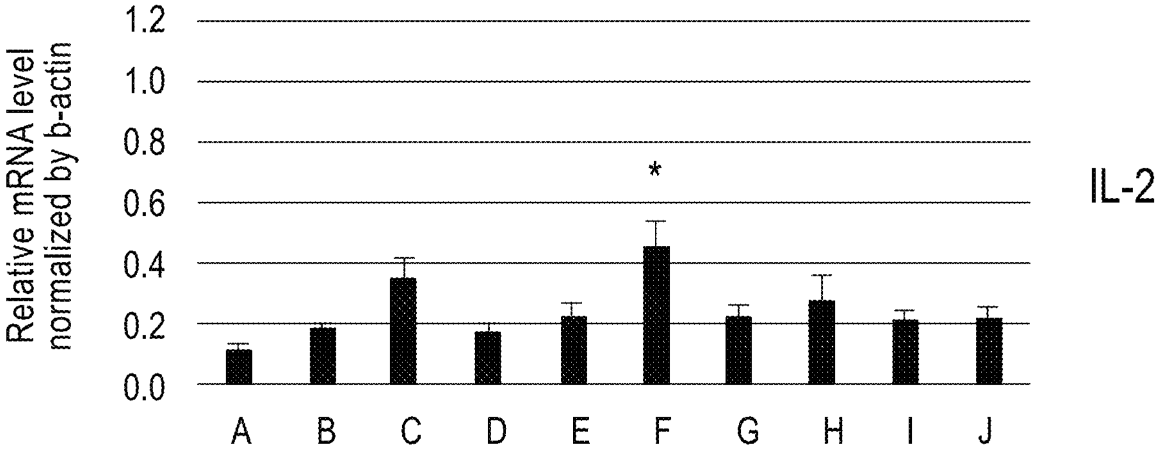
Figure 16D:
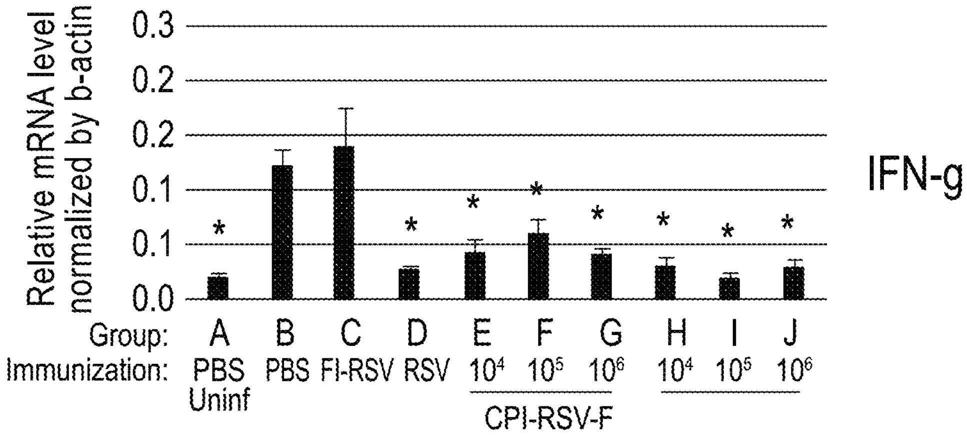
Figure 17A:
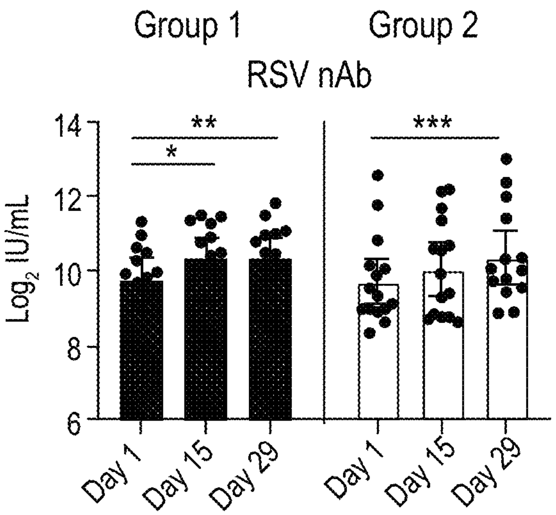
FIGS. 17A-17F are bar graphs showing serum RSV-specific antibody (Ab) titers before and after vaccination with BLB201 (CPI-RSV-F) for younger adults (Group 1) and older adults (Group 2).
Figure 17B:
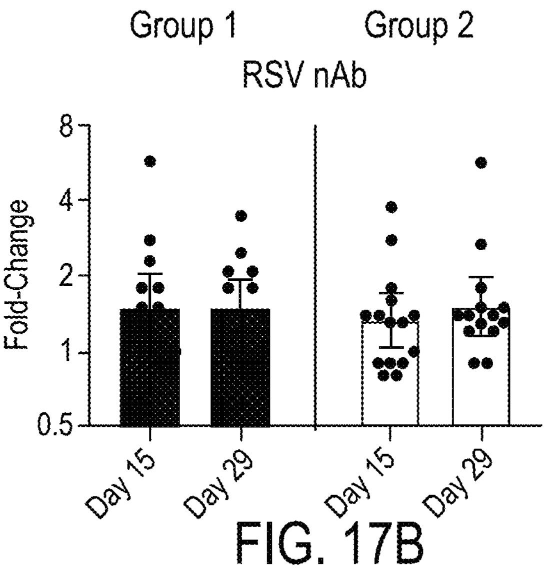
Figure 17C:
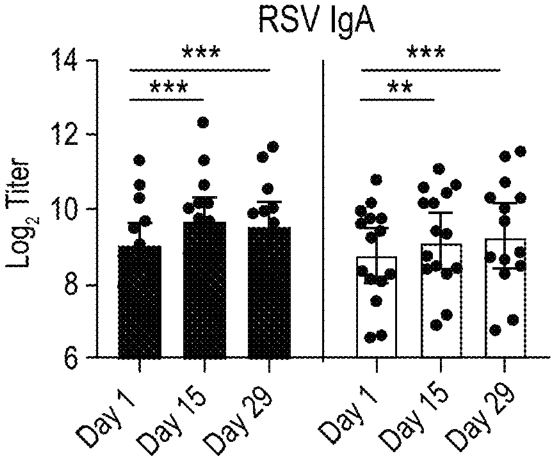
Figure 17D:
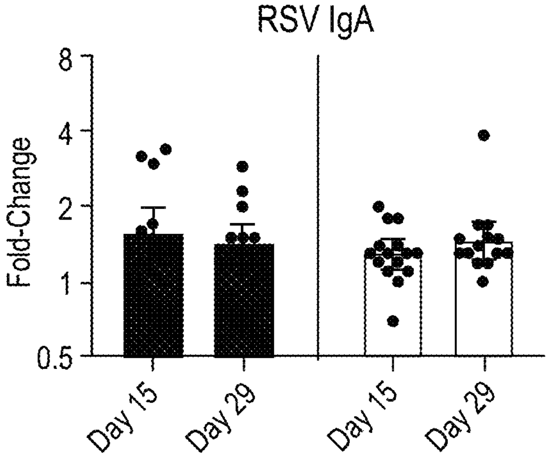
Figure 17E:
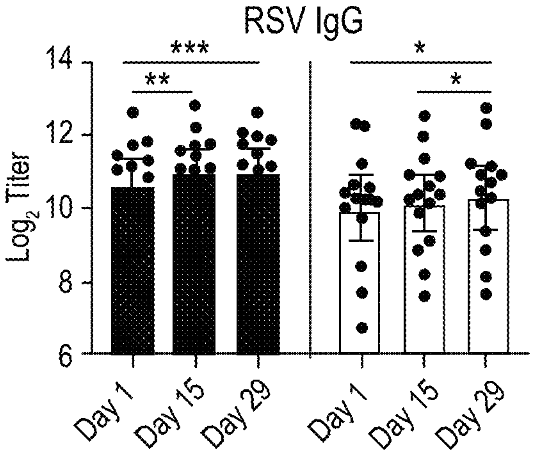
Figure 17F:
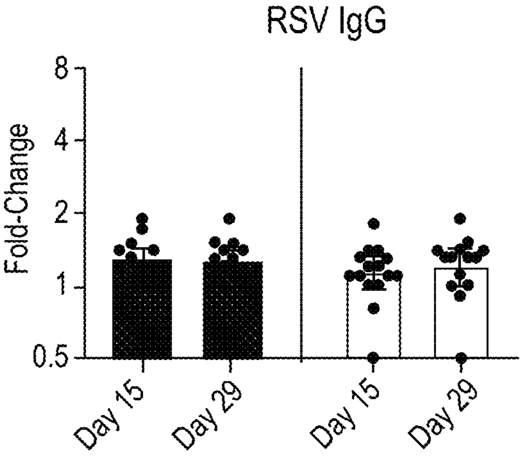
Figure 18A:
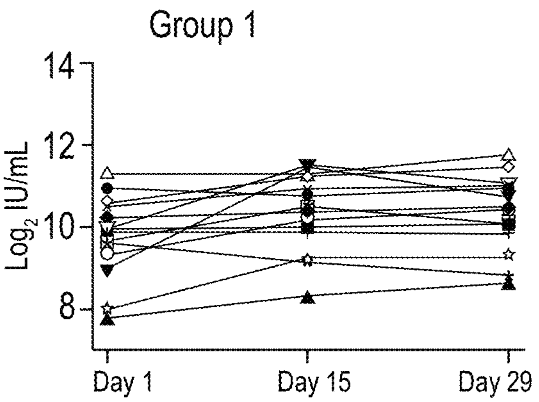
FIGS. 18A-18D are line graphs showing individual subject's serum RSV neutralizing (nAb) titers of Group 1 (FIG. 18A) and Group 2 (FIG. 18B) and nasal F-specific IgA antibody (Ab) titers before and after vaccination with BLB201 (CPI-RSV-F) (at Days 1, 15 and 29) (FIGS. 18C-18D) and by age group 1 and 2.
Figure 18B:
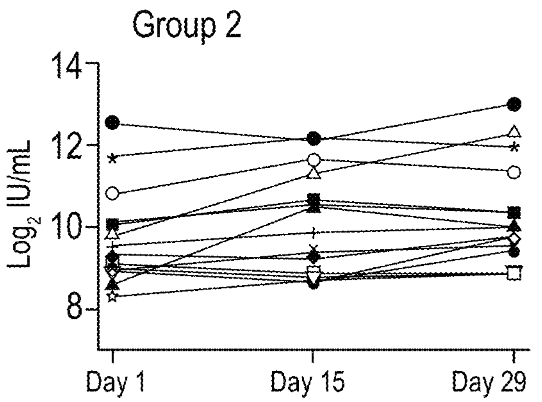
Figure 18C:
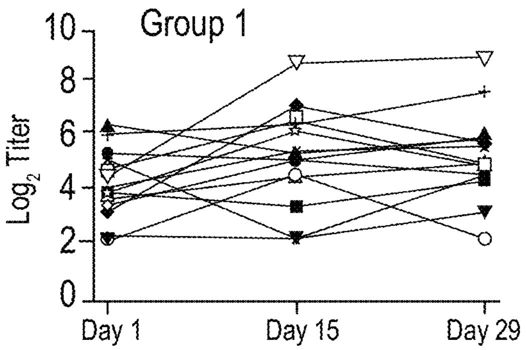
Figure 18D:
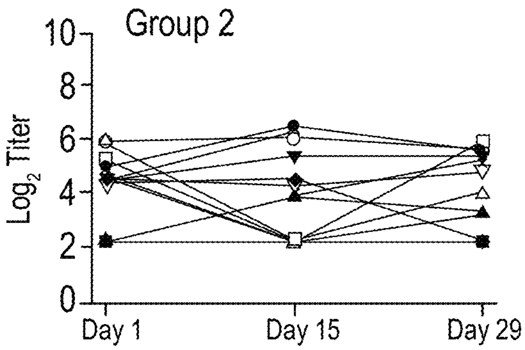

Serum RSV A/A2 Binding IgG Antibodies: Serum binding IgG antibodies against RSV A/A2 F protein were measured in all animals prior to the start of experiment (day 0), 4 weeks after the first immunization (day 28), and three weeks later (day 49) (FIG. 15). A small increase in binding IgG was visible in animals vaccinated with FI-RSV (Group C). Animals infected with RSV A/A2 (Group D) and all animals immunized with CPI-RSV-F (Groups E-G) or W3AΔSH-RSV-F (Groups H-J) had high levels of binding IgG on days 28 and 49 post-inoculation. No dose-dependency of IgG levels on either CPI-RSV-F (Groups E-G) or W3AΔSH-RSV-F (Groups H-J) doses was seen. IgG levels were slightly higher in W3AΔSH—RSV-F-immunized animals compared to animals immunized with CPI-RSV-F (Groups E-G) on both days 28 and 49.

Lung Histopathology: Pulmonary histopathology was evaluated in all animals 5 days after RSV A/A2 challenge (Data not shown). RSV-infected animals mock-immunized with PBS (Group B) or challenged with RSV twice (Group D) had moderate level of pathology. The highest level of pulmonary histopathology was detected in animals immunized with FI-RSV (Group C), with prominent increases in interstitial inflammation and alveolitis. Pathology of animals immunized with CPI-RSV-F in all doses (Groups E-G) did not exceed that seen in animals with secondary RSV infection (Group D). A group of animals immunized with W3AΔSH-RSV-F in the dose of $10^5$ PFU (Group I) had one animal (#124872) with elevated interstitial inflammation and alveolitis. The four other animals in that groups and all animals immunized with the other two doses of vaccines (Groups H and J) did not exhibit interstitial inflammation and alveolitis.

qPCR Results: Expression of RSV NS1, IL-4, IL-2, and IFN-γ mRNA was evaluated in lung samples collected on day 5 after RSV A/A2 challenge and normalized by the level of β-actin mRNA in each sample (FIG. 16A-16D). Expression of NS-1 mRNA was strongly reduced by both vaccines, with W3AΔSH-RSV-F being slightly more efficacious at reducing lung NS1 mRNA compared to CPI-RSV-F administered at the two lower doses ($10^4$ and $10^5$ PFU). FI-RSV immunization (Groups C) resulted in moderate reduction in lung RSV NS1 mRNA level, but significantly increased IL-4 mRNA level. IL-4, IL-2, and IFN-γ mRNA levels in animals immunized with CPI-RSV-F (Groups E-G) or W3AΔSH-RSV-F (Groups H-J) overall did not exceed that seen in animals with primary RSV infections (Group B). Several animals in the group immunized with the intermediate dose of CPI-RSV-F (Group F, $10^5$ PFU dose) showed slightly elevated IL-2 and IFN-γ mRNA levels compared to animals with secondary RSV infection (Group D). One animal in the group immunized with the intermediate dose of W3AΔSH-RSV-F (Group I, $10^5$ PFU dose, animal ##124872) had elevated IL-4 mRNA. Coincidentally, this same animal showed elevated alveolitis and interstitial inflammation in histopathology evaluation.

Example 5: Phase I Clinical Trial of PIV5-RSV Vaccine-RSV Antibody and CMI Response Rates Materials and Methods Participants and study conduct: A total of 30 subjects were enrolled in this phase 1 trial and all received a single intranasal dose of the PIV5-RSV vaccine at $10^{7.5}$ PFU. The vaccine was administrated as a 0.25 mL spray to each nostril (total volume 0.5 mL) using a MAD Nasal™ Intranasal Mucosal Atomization Device (Teleflex MAD300). The mean ages in Group 1 (planned participant age 18-59 years and actual enrollee age 33-59 years) and Group 2 (planned participant age 60-75 years and actual enrollee age 61-75 years) were 45 years and 67 years, respectively (Table 18). The majority of participants were female (70%). Most participants in the two groups were White (73% and 80% in Groups 1 and 2, respectively). All except one participant completed the study; and this participant in Group 1 was lost to follow-up after Day 7.

TABLE 18

Trial cohort demographics

| Group | Group 1 | Group 2 |
|---|---|---|
| N | 15* | 15 |
| Mean age (range) | 44.9 (33, 59) | 66.8 (61, 75) |
| Male/female | 4/11 | 5/10 |
| Race/ Ethnicity | 11 White (73%), others-Black/African American and American Indian | 12 White (80%), others-Black/African American and Asian |

*One participant dropped out of the study on Day 8 (lost to follow-up).

Study design and vaccination: The phase 1 clinical trial of PIV5-RSV vaccine (also referred to as BLB201; Clinical Trials NCT05281263) was approved by the Advarra central IRB and conducted at two study sites in the US. Participants were recruited to two study cohorts, healthy young adults (Group 1, 33-59 years old) and healthy older adults (Group 2, 61-75 years old). Participants of childbearing potential were required to practice contraceptive measurement to prevent pregnancy. Exclusion criteria included any live vaccine within the 30 days prior to trial vaccine, any prior receipt of any investigational RSV vaccine or any PIV5-based vaccine (CVXGA1) that was actively enrolling during the trial period and known infection with human immunodeficiency virus, hepatitis B virus, or hepatitis C virus. A full list of inclusion and exclusion criteria can be found on the clinical trials website. Participants were not prescreened for their RSV serum antibody levels. Eligible participants were administered on Day 1, a single dose at a concentration of 107.5 plaque forming unit (PFU) of PIV5-RSV vaccine, as a 0.25 mL spray to each nostril (total volume 0.5 mL) using a MAD Nasal™ Intranasal Mucosal Atomization Device (Teleflex MAD300) and observed for 30 minutes immediately after dosing. In addition, subjects were asked to maintain a memory aid for solicited systemic AEs and local reactions during the week after vaccination. Four sentinel participants were dosed first in each group, and their safety data was reviewed by the safety monitory committee (SMC) before the remainder of the participants in the group were enrolled.

Primary outcome measures included (i) solicited AEs (Day 1-8), and (ii) unsolicited AEs (Days 1-29). Secondary outcome measures included (i) serum IgG titers to RSV protein (Days 15 and 29) (ii) SAEs (Days 1-181) and (iii)

AEs of special interest (AESIs) including x-onset chronic medical conditions, and medically-attended AEs (Days 1-181).

Immunogenicity assessment: Blood and nasal samples were collected at baseline (Day 1, pre vaccination), Day 15, and Day 29 post-vaccination. To reduce sample variation, samples from the same participant were run on the same plate in a blinded fashion in all the assays. Serum RSV nAb levels were determined by a qualified RSV A2 microneutralization (MN) assay based on RSV-A2-rLuc reporter virus (45). Briefly, serially 2-fold diluted serum samples in quadruplicate from a starting dilution of 1:100 were incubated with 175±75 PFU RSV-rLuc for 1 hr, and infected Vero cells on 96-well, white-walled, clear bottom plates. After 20 to 24 hr incubation, the cells were lysed using *Renilla*-Glo Luciferase assay (Promega) and luciferase signals were read on a SpectraMax iD3 multi-mode microplate reader (Molecular Devices). RSV nAb titer was defined as reciprocal dilution that inhibited at least 50% signal of the virus control as determined by 5PL curve fitting using Prism (Version 9.5.1 for macOS, GraphPad Software). The RSV nAb titer was converted to international units based on the standard serum (16/284) obtained from NIBSC (London, UK).

RSV F specific serum IgG and IgA antibody, and nasal IgA antibody levels were determined by ELISA assay using 25 ng/well of purified RSV F protein (SinoBiological, cat #11049-V08B) and 2-fold serial dilutions in blocking buffer (5% milk/0.5% BSA in 1× KPL wash buffer (Seracare) in duplicate. End point titer was calculated by 4PL curve fitting using Prism and reported as reciprocal dilution. PIV5-specific IgG and nAb titers were determined by ELISA assay using PIV5 virus coated plates and by PIV5-rLuc-based MN assay in Vero cells, respectively. The PIV5 IgG end point titer was calculated by 4PL curve fitting and reported as reciprocal dilution. The PIV5 MN assay was performed similarly to the RSV-rLuc based MN assay, except in duplicate instead of quadruplicate. Analysis of PIV5 MN was identical to the RSV-rLuc based MN assay and the nAb titer was defined as the reciprocal dilution that inhibited at least 50% signal of the virus control.

Antigen-specific T-cell frequencies were evaluated by intracellular cytokine staining assay using cryopreserved peripheral blood mononuclear cells (PBMCs) isolated from whole blood on Day 1 (pre-vaccine dosing), Day 15, and Day 29. One million cryopreserved PBMCs were thawed in complete 10% FBS RPMI medium and rested overnight at 37° C. before being incubated with an RSV F peptide pool from GenScript at a final concentration of 1 μg/mL in the presence of 1 μg/mL anti-CD28 ECD (Beckman Coulter, clone CD28.2), anti-CD107a FITC (BD Biosciences, clone H4A3) and anti-CD49d (BD Biosciences, clone 9F10). In addition, PBMCs were stimulated with 1 μL of complete medium with 0.5% dimethyl sulfoxide (DMSO, negative control corresponding to the DMSO concentration of the RSV-F peptide pool) or 1 μL of PMA/ionomycin (25 ng/mL PMA and 1 μg/mL ionomycin) for negative and positive controls, respectively. After 2 hrs incubation at 37° C., 10 μg/mL brefeldin A (BD Biosciences) were added and the cells were incubated for another 4 hrs. The cells were washed with PBS and incubated with Aqua-Viability dye (Invitrogen) at room temperature for 15 mins. The cells were washed with PBS supplemented with 2% fetal bovine serum (FBS), and surface stained at 4° C. for 30 mins with anti-CD3 Alexa700 (BD Biosciences, clone SP34-2), anti-CD4 BV605 (BD Biosciences, clone L200), anti-CD8 BV450 (BD Biosciences, clone RPA-T8), and anti-CD95 PE-Cy5 (BD Biosciences, clone DX2). The cells were washed with PBS with 2% FBS, fixed with Cytofix/Cytoperm (BD Biosciences), permeabilized with 1× Perm/Wash (BD Biosciences), and incubated with anti-IFN-γ PE-Cy7 (BD Biosciences, clone B27), anti-TNF-α APC-Cy7 (BioLegend, clone Mab 11), anti-IL-13 PE (Miltenyi Biotec, clone JES10-5A2.2) and anti-MIP-1β APC (eBioscience, clone FL34Z3L) antibodies at 4° C. for 30 mins. The cells were washed with 1× Perm/Wash and PBS with 2% FBS then resuspended in PBS/2% formaldehyde for acquisition on a BD FACSAria Fusion cell sorter. CD3+ cells were gated for $CD4^+$ and $CD8^+$ T-cells and separated into memory and naïve cells with CD28 and CD95. The net percentage of cytokine-secreting cells was determined by subtraction of the values obtained with DMSO-stimulated samples (negative control). T cell frequencies were considered positive if the detected frequency of cytokine positive $CD4^+$ or $CD8^+$ T cells was >0.1% after subtraction of baseline. Data were analyzed using FlowJo software (version 10). A Boolean combination and SPICE software were used to determine polyfunctional responses of $CD4^+$ and $CD8^+$ T cells producing two or more cytokines.

Statistical analysis: Statistical analysis was performed using GraphPad Prism software (Version 9). Given the small sample size, statistical analysis was mostly descriptive and summative. P values were used to show difference of potential significance at a 0.05 significance level. Two-group comparisons of RSV-specific CMI responses and antibody responses were evaluated by the Wilcoxon matched-pairs signed rank test (Day 15 or Day 29 vs Day 1, or Day 15 vs Day 29). Antibody titer rises of 1.5-fold post-vaccination vs baseline was considered meaningful because assay characteristics showed a change of 1.2-1.3-fold (95% confidence) to be a notable change when samples from a single participant were tested on the same plate.

Results

Serum antibody titers: All participants were seropositive for RSV neutralizing Abs (nAbs) at baseline and the titer changes are presented in FIGS. 17A-17F and FIGS. 18A-18B. In Group 1, the nAbs geometric mean titer (GMT) was 880 (9.8 log 2) at baseline and increased to 1316 (10.4 log 2) at 2-weeks and 1312 (10.4 log 2) at 4-weeks after vaccination (P<0.05), reflecting a geometric mean fold rise (GMFR) of 1.5. RSV-nAb seroresponses (≥1.5-fold rise) were identified in 7/14 (50%) participants. In Group 2, the nAb GMT was 850 (9.7 log 2) at baseline, similar to that in Group 1, increased to 1103 (10.1 log 2) at 2-weeks (P<0.05), and 1372 (10.4 $\log_2$) at 4-weeks after vaccination (P<0.05), reflecting geometric mean fold rise (GMFRs) of 1.3 and 1.5, respectively. RSV-nAb seroresponses were identified in 6/15 (40%) participants in this group (Table 19) (individual nAb titer changes were shown in FIGS. 18A-18D). Notably, RSV-nAb seroresponses were identified in all 5 participants positive for vaccine-virus shedding, suggesting a potential correlation between replication and systemic antibody responses.

TABLE 19

Summary of RSV antibody and CMI response rates

| Sample | Immune parameter | Group 1 responders n/N (% responder) | Group 2 responders n/N (% responder) |
|---|---|---|---|
| Serum | RSV nAb | 7/14 (50%) | 6/15 (40%) |
| | RSV F IgA | 6/14 (43%) | 5/15 (36%) |
| | RSV F IgG | 3/14 (21%) | 1/15 (7%) |
| | PIV5 nAb | 7/14 (50%) | 10/15 (67%) |
| | PIV5 IgG | 12/14 (86%) | 13/15 (87%) |

TABLE 19-continued

| Summary of RSV antibody and CMI response rates | | | |
|---|---|---|---|
| Sample | Immune parameter | Group 1 responders n/N (% responder) | Group 2 responders n/N (% responder) |
| Nasal Swab | Nasal RSV F IgA | 9/14 (64%) | 5/15 (33%) |
| PBMC | Total CMI | 13/14 (93%) | 15/15 (100%) |
| | CD8 CTL | 12/14 (86%) | 13/15 (87%) |

A positive seroresponse was defined as ≥1.5-fold rise from baseline for RSV F IgG and IgG. A positive nasal IgA antibody response was defined as ≥2-fold rise over baseline. CMI response was defined as >0.1% rise of sum of individual T cell secreting >1 cytokine after subtraction of baseline (pre-vaccination). CTL response was defined by the change in INF-γ producing $CD8^+$ cells. Abbreviations: CMI, cell-mediated immunity; CTL, cytotoxic T lymphocyte; PBMC, peripheral blood mononuclear cell; PIV5, parainfluenza virus type 5; RSV, respiratory syncytial virus.

All participants were also seropositive for RSV-F-specific serum IgA and IgG Abs, at baseline (FIGS. 17A-17F). In Group 1, F-specific serum IgA GMT increased from 530 (9.0 $\log_2$) at baseline to 821 (9.7 log 2) and 756 (9.6 $\log_2$) at 2- and 4-weeks after vaccination, respectively. F-specific serum IgG GMT increased from 1640 (10.7 $\log_2$) at baseline, to 2049 (11.0 $\log_2$) at 2-weeks and 2055 (11.0 $\log_2$) at 4-weeks after vaccination. F-specific serum IgA and IgG seroresponses (≥1.5-fold) were identified in 6/14 (43%) and 3/14 (21%) participants, respectively (Table 19). In Group 2, F-specific serum IgA GMT increased from 445 (8.8 $\log_2$) at baseline, to 582 (9.2 $\log_2$) and 641 (9.3 $\log_2$) at 2- and 4-weeks after vaccination, respectively. F-specific serum IgG GMT increased from 1088 (10.1 $\log_2$) at baseline, to 1198 (10.2 $\log_2$) and 1325 (10.4 $\log_2$) at 2- and 4-weeks after vaccination. F-specific IgA and IgG seroresponses were identified in 5/15 (33%) and 1/15 (7%) participants, respectively (Table 19).

Overall, the results suggested the PIV5-RSV vaccine boosted RSV-specific serum Ab levels in young adults (33-59-year old) and elderly (61-75-year old), though with greater magnitude in adults vs elderly. Interestingly, the fold increases in RSV-specific Ab titers inversely correlated with baseline titers. It is possible that the higher baseline titers were close to maximum levels.

Figure 19A:
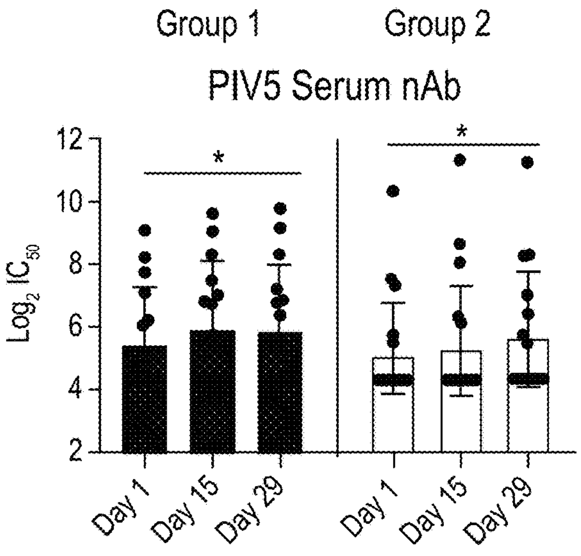
FIGS. 19A-19D are bar graphs showing serum PIV5 antibody (Ab) titers before and after vaccination with BLB201 (CPI-RSV-F) for two vaccination groups.
Figure 19B:
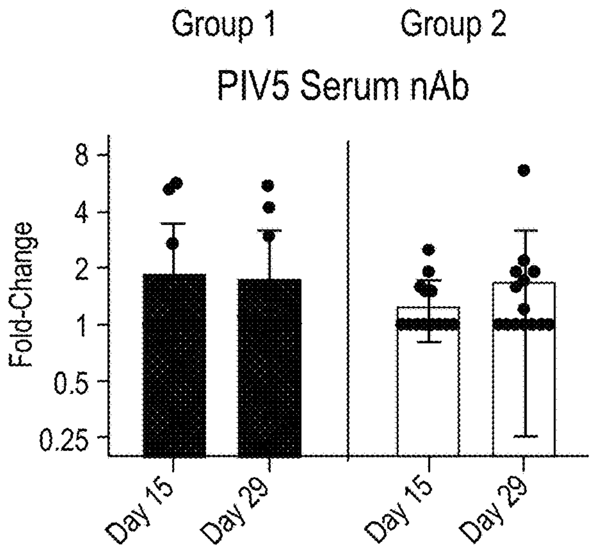
Figure 19C:
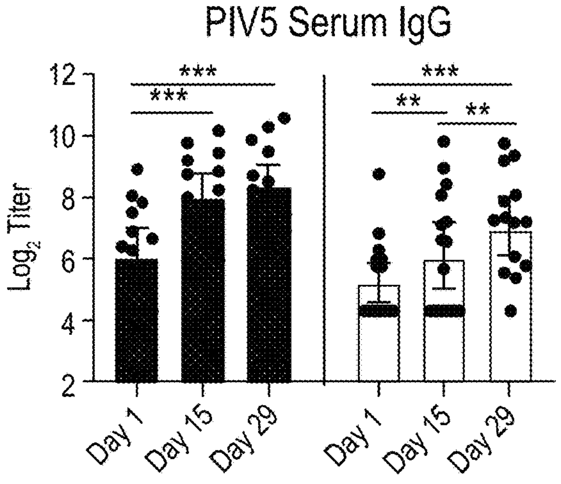
Figure 19D:
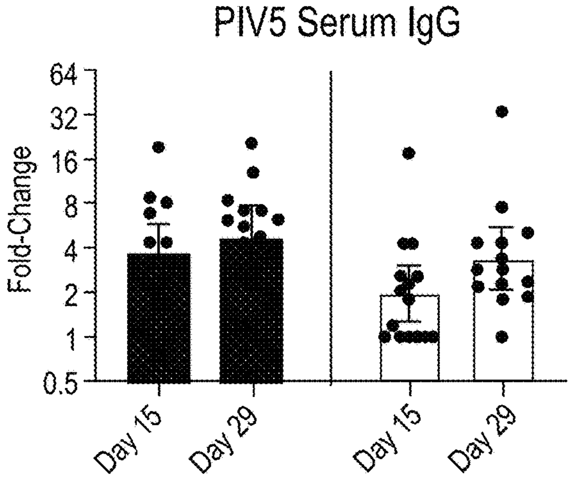
Figure 20A:
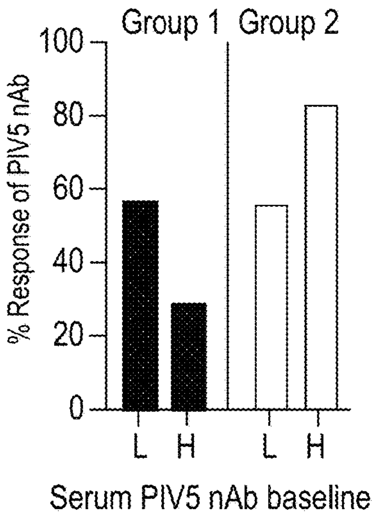
FIGS. 20A-20C are bar graphs showing the relationships between response rates to PIV5-RSV vaccination based on PIV5 neutralizing antibody (nAb) levels at baseline (pre-vaccination). Percentage of subjects with (FIG. 20A) PIV5 neutralizing (nAb) seroresponses to the PIV5-RSV vaccine (≥1.5-fold rise in titer) and (FIG. 20B) RSV neutralizing (nAb) seroresponses to the PIV5-RSV vaccine (≥1.5-fold rise in titer) by subgroups based on individual subject's baseline PIV5 nAb titer being below (L) or above (H) the baseline geometric mean titer for PIV5 nAbs for each age group (Group 1 and Group 2).
Figure 20B:
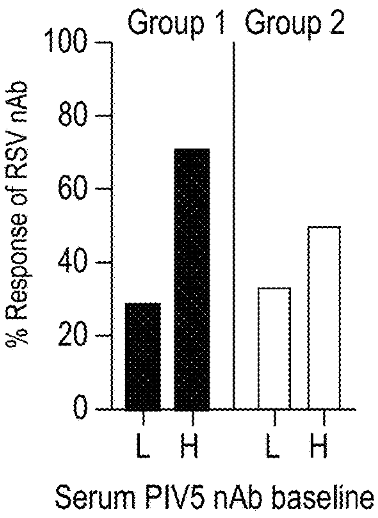
Figure 20C:
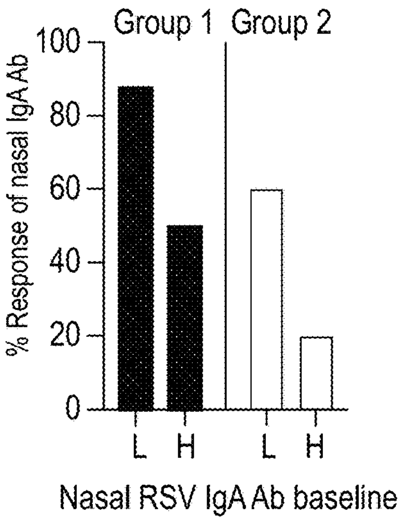

We next examined vector-specific immune responses. For PIV5 nAbs at baseline, 15/29 (52%) participants were seropositive as defined by a titer of 1:10 (FIGS. 19A-19B). This level of background seropositivity likely reflects passive exposure to PIV5 through exposure to dogs receiving the kennel cough vaccine. In Group 1, the PIV5-nAb GMT increased from 26 (4.7 $\log_2$) at baseline, to 48 (5.6 $\log_2$) and 51 (5.7 $\log_2$) at 2- and 4-weeks after vaccination, respectively, reflecting a geometric mean fold rise of 1.8 and 2.0 respectively. PIV5-nAb seroresponses (≥1.5-fold rise) were identified in 7/14 (50%) participants (Table 19). In Group 2, the PIV5-nAb GMT increased from 19 (4.2 $\log_2$) at baseline, to 34 (5.1 $\log_2$) and 44 (5.5 $\log_2$) at 2- and 4-weeks after vaccination, respectively, reflecting a GMFRs of 1.8 and 2.2 respectively. PIV5-nAb seroresponses (≥1.5-fold rise) were identified in 10/15 (67%) participants. Similar kinetics were observed with PIV5-specific IgG titers (FIGS. 19C-19D), but with greater GMFRs (≤4.6 fold in Group 1 and ≤3.4 fold in Group 2) and seroresponses (86% in Group 1 and 87% in Group 2). By comparing participants with low PIV5 nAb titers with those with high PIV5 nAb titers, baseline PIV5 nAb titers had no clear effect on PIV5-nAb seroresponse rate and appeared to not inhibit RSV-nAb seroresponse rate (FIGS. 20A-20C).

Figure 21A:
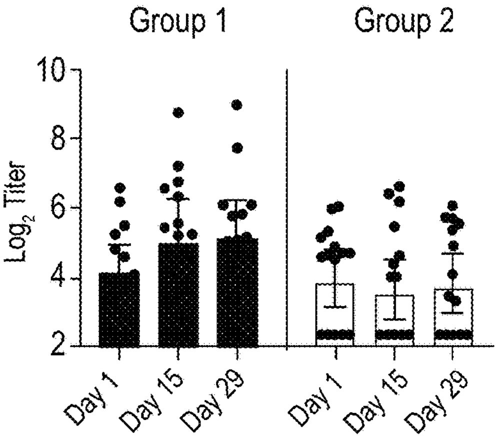
FIGS. 21A-21B are bar graphs showing nasal IgA antibody titers before and after vaccination for Groups 1 and 2. F-specific RSV IgA Abs by ELISA. Individual $\log_2$ titers, and mean $\log_2$ titers with the respective standard deviations (error bars) at Days 1, 15 and 29 by age group are shown in the left graph (FIG. 21A), and geometric mean fold rises from baseline (GMFRs) on Day 15 and Day 29 by age group are shown in the graph (FIG. 21B).
Figure 21B:
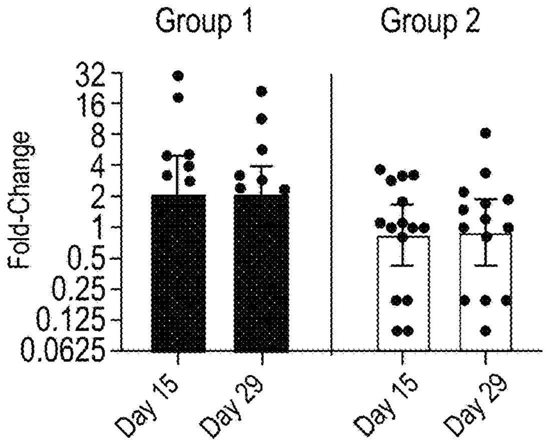

RSV F-specific IgA antibody titers in nasal swabs: At baseline, RSV F-specific IgA antibody (Ab) titers in nasal swabs were variable ranging from below the LOD to 514 (9.0 $\log_2$) (FIG. 21A). In Group 1, the F-specific nasal IgA geometric mean titer (GMT) was 19 (4.2 $\log_2$) at baseline and increased to 40 (5.3 $\log_2$) at 2- and 4-weeks after vaccination (P<0.05), reflecting a GMFR of 2.1 (FIG. 21B). F-specific nasal IgA responses (≥2-fold rise) were identified in 9/14 (64%) participants (Table 19). In Group 2, the baseline F-specific nasal IgA GMT of 18 (4.2 $\log_2$) was similar to that in Group 1, but GMTs were not boosted (P>0.05) 2-weeks and 4-weeks after vaccination (FIGS. 21A and 21B). However, F-specific nasal IgA responses were identified in 5/15 (33%) participants in Group 2 (individual's nasal IgA antibody changes were shown in FIGS. 18C-18D). In Groups 1 and 2, F-specific nasal IgA responses were identified in 4/5 participants positive for vaccine-virus shedding.

Overall, the results suggested that the PIV5-RSV vaccine boosted RSV-specific nasal IgA levels in adults and elderly, but to a lesser degree in elderly. Similar to results seen with systemic antibody responses, the fold increases in F-specific nasal IgA titers in both groups inversely correlated with baseline titers (FIGS. 20A-20C).

Figures 22A, 22B, 22C, 22D:
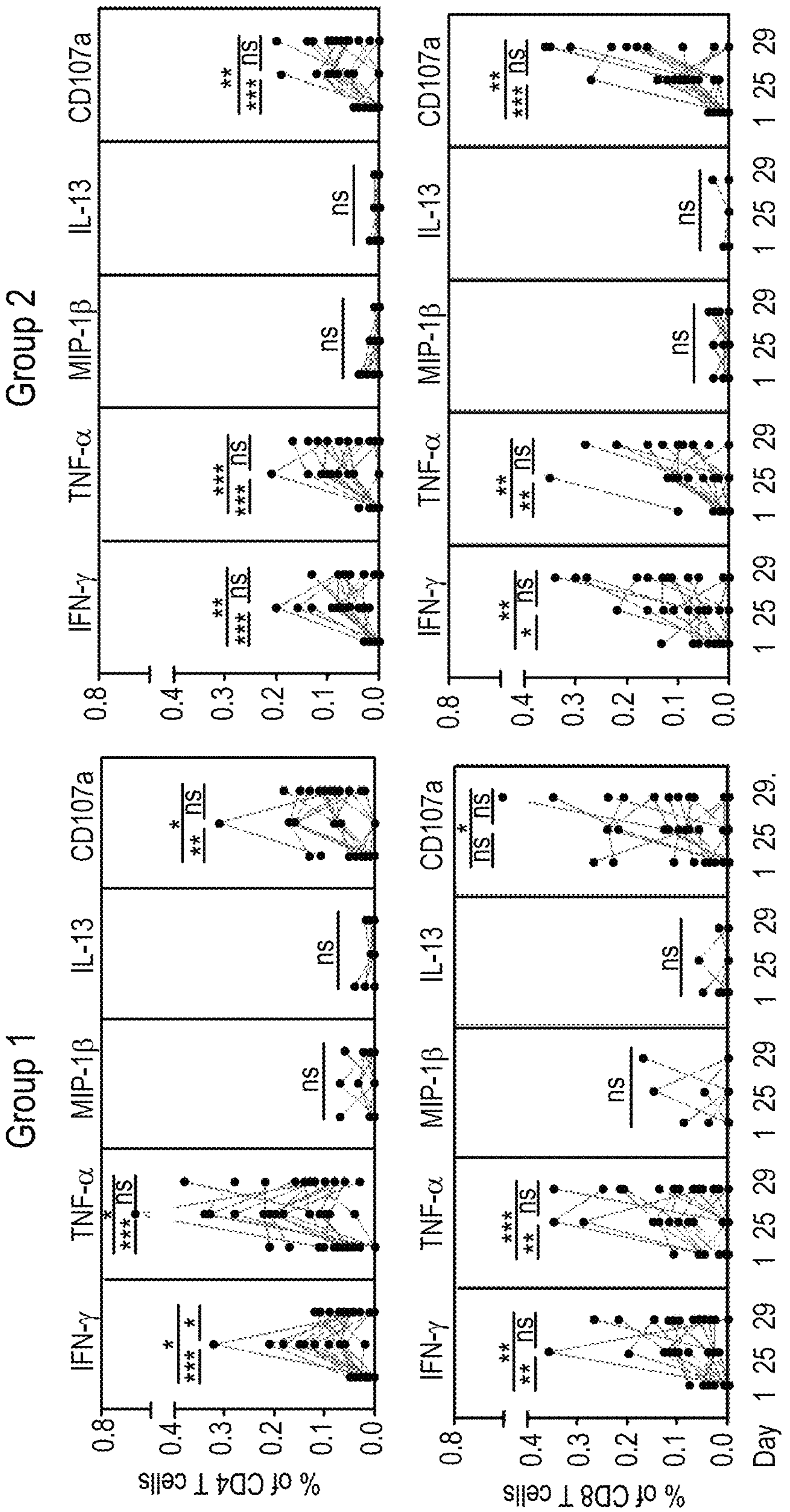
FIGS. 22A-22J show RSV F-specific $CD4^+$ and $CD8^+$ T cell responses before and after vaccination of BLB201 (CPI-RSV-F). Percentages of $CD4^+$ T cells (upper graphs) and $CD8^+$ T cells (22A-D) by age group on Days 1, 15 and 29 for each individual (represented by symbols and contiguous line) by expression of the indicated immune marker.
Figure 22E:
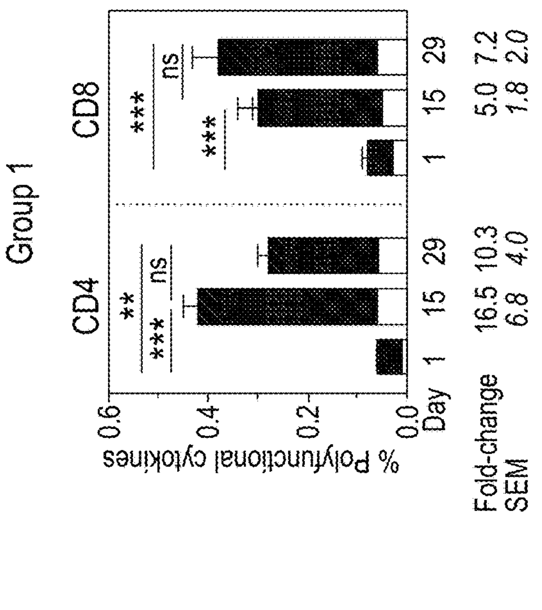
Figure 22F:
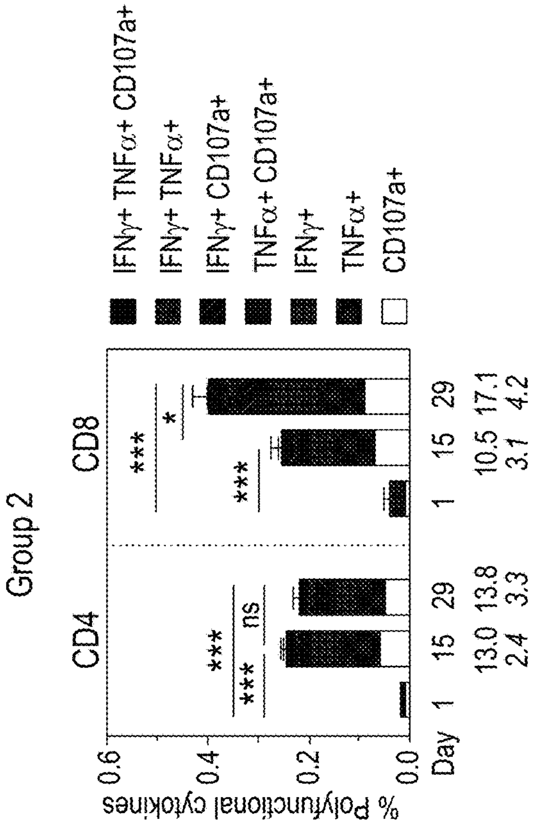
Figure 22G:
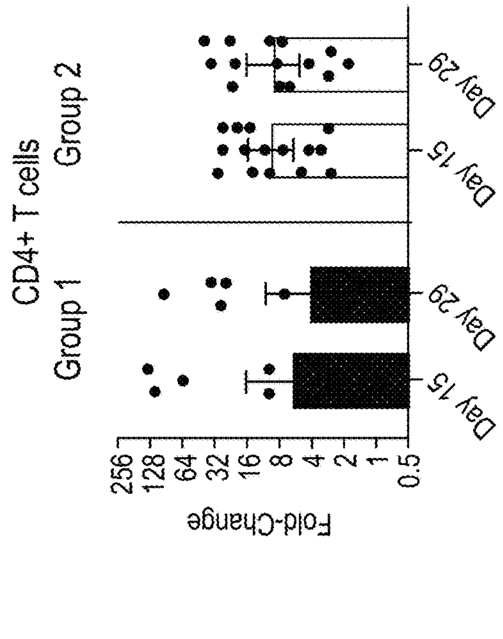
Figure 22H:
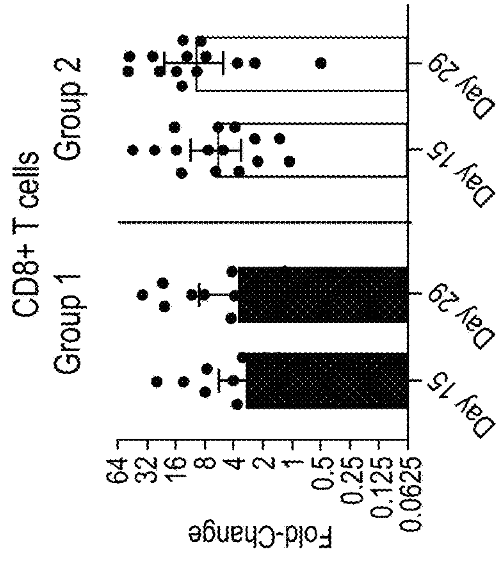

Cell mediated immunity at baseline, RSV F-specific $CD4^+$ and $CD8^+$ T cells were detected, based on the expression of Th1 or cytotoxic T-cell cytokines/markers IFN-γ, TNF-α, MIP-1β and CD107a, and on the expression of Th2 cytokine IL-13 (FIG. 22A-22D). In Group 1, the mean percentages of F-specific $CD4^+$ T cells expressing at least one of the Th1/cytotoxic markers increased from 0.06% at baseline to a maximum of 0.42% 2-weeks after vaccination (P<0.001; FIGS. 22E-22F), and the mean percentages of the same phenotypes of $CD8^+$ T cells increased from 0.08% at baseline to a maximum of 0.38% 4-weeks after vaccination (P<0.001). In Group 2, the mean percentages of the same phenotypes of $CD4^+$ T cells increased from 0.02 to a maximum of 0.26%, 2-weeks after vaccination (P<0.001), and $CD8^+$ T cells increased from 0.04 to a maximum of 0.40% 4-weeks after vaccination (P<0.001). In Groups 1 and 2, F-specific cell-mediated immunity (CMI) responses to the PIV5-RSV vaccine (defined as an increase from baseline of >0.1% of T cells expressing at least 2 Th1/cytotoxic biomarkers) were identified in 13/14 (93%) and 15/15 (100%) participants, respectively (Table 19). And F-specific cytotoxic T-lymphocyte (CTL) responses to the PIV5-RSV vaccine (defined as an increase from baseline of >0.1% of $CD8^+$ T cells expressing IFN-γ) were identified in 12/14 (86%) and 13/15 (87%) participants, respectively. This suggested that the PIV5-RSV vaccine enhanced the production of F-specific Th1 ($CD4^+$) and cytotoxic ($CD8^+$) T cells in nearly all participants. Even though numbers of $CD4^+$ and $CD8^+$ T cells were similar after immunization in both groups, geometric mean of $CD4^+$ T cells rose to 6.1- and 9.1-fold by day 15 for Group 1 and 2 respectively, and geometric mean of $CD8^+$ T cells rose to 3.6- and 10-fold by day 29 for Group 1 and 2 respectively (FIG. 22G-22H), reflecting lower baseline for Group 2 than for Group 1. This result suggests that in contrast to nasal IgA response, similar levels of CMI in adults and elderly was induced by the PIV5-RSV vaccine.

Figure 22J:
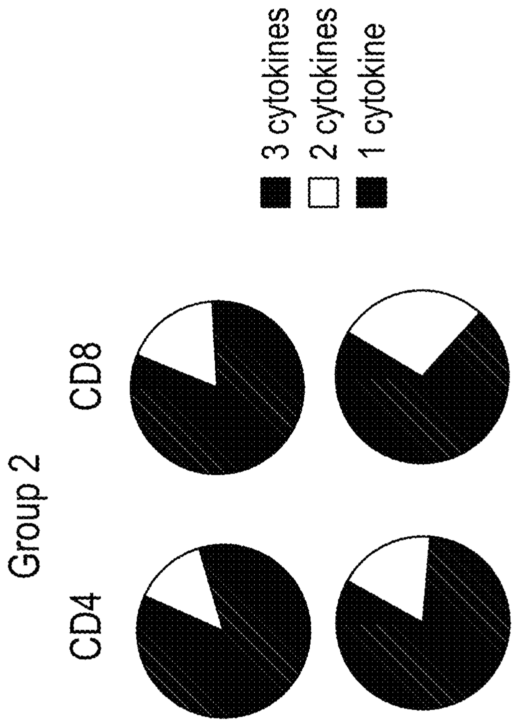
Figure 22I:
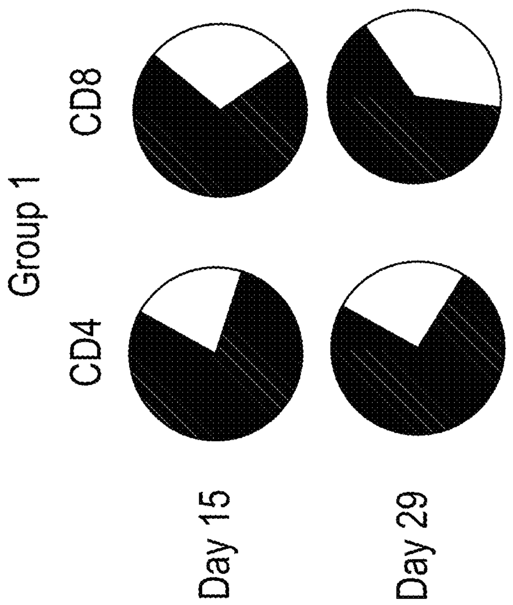

In both Group 1 and Group 2, T cells expressing a single Th1/cytotoxic biomarker were more frequent than those expressing at least two Th1/cytotoxic markers (FIG. 22I-22J). However, T-cells co-expressing at least two Th1/ cytotoxic biomarkers tended to be more frequent in Group 1 vs Group 2, suggesting that the PIV5-RSV vaccine may induce better quality of antigen specific effector/memory T cells in the younger age group, based on polyfunctional Th1/cytotoxic responses.

In contrast to Th1 and cytotoxic phenotypes, the percentages of F-specific $CD4^+$ T cells and $CD8^+$ T cells expressing IL-13 did not increase after vaccination in either Group 1 or Group 2 (FIG. 22A-22D), indicating that there was no Th2-biased response to the PIV5-RSV vaccine, which has been identified as a potential risk factor for vaccine-associated enhanced RSV disease (F. P. Polack, et al., *J Exp Med* 196, 859-865 (2002); B. Bagga, et al., *J Infect Dis* 212, 1719-1725 (2015)).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

REFERENCES

1. Phan S I, Zengel J R, Wei H, et al. Parainfluenza virus 5 expressing wild-type of prefusion respiratory syncytial virus (RSV) fusion protein protects mice and cotton rats from RSV challenge. J of Virology 2017:91(19); e00560-17.
2. Wang D, Phan S, DiStephano D J, et al. A single-dose recombinant parainfluenza virus 5-vectored vaccine expressing respiratory syncytial virus (RSV) F or G protein protected Cotton rats and African green monkeys from RSV challenge. J of Virology 2017:91(11); e00066-17.
3. Phan S I, Chen Z, Xu P, et al. A respiratory syncytial virus (RSV) vaccine based on parainfluenza virus 5 (PIV5). Vaccine 2014:32; 3050-3057.
4. Young D, Wignall-Fleming E B, Busse D C, et al. The switch between acute and persistent paramyxovirus infection caused by single amino acid substitutions in the RNA polymerase P subunit. PLOS Pathogens 2019 Feb. 11; 15(2):e1007561. doi: 10.1371/journal.ppat.100756.
5. Seth et al. Mutations in the cytoplasmic domain of a paramyxoviruses fusion glycoprotein rescue syncytium formation and eliminate the HN requirement for membrane fusion. J. of Virology 2003, 167-178.
6. Tong et al. Regulation of Fusion Activity by the Cytoplasmic Domain of a Paramyxovirus F Protein. J. of Virology 2002, 301:322-333.
7. Schmitt, A. P., Leser, G. P., Waning, D. L. & Lamb, R. A. Requirements for Budding of Paramyxovirus Simian Virus 5 Virus-Like Particles. Journal of Virology 76, 3952-3964, doi: 10.1128/jvi.76.8.3952-3964.2002 (2002).
8. Waning, D. L., Schmitt, A. P., Leser, G. P. & Lamb, R. A. Roles for the cytoplasmic tails of the fusion and hemagglutinin-neuraminidase proteins in budding of the paramyxovirus simian virus 5. JVirol 76, 9284-9297 (2002).
9. F. P. Polack, M. N. Teng, P. L. Collins, G. A. Prince, M. Exner, H. Regele, D. D. Lirman, R. Rabold, S. J. Hoffman, C. L. Karp, S. R. Kleeberger, M. Wills-Karp, R. A. Karron, A role for immune complexes in enhanced respiratory syncytial virus disease. *J Exp Med* 196, 859-865 (2002).
10. B. Bagga, J. E. Cehelsky, A. Vaishnaw, T. Wilkinson, R. Meyers, L. M. Harrison, P. L. Roddam, E. E. Walsh, J. P. DeVincenzo, Effect of Preexisting Serum and Mucosal Antibody on Experimental Respiratory Syncytial Virus (RSV) Challenge and Infection of Adults. *J Infect Dis* 212, 1719-1725 (2015).

What is claimed is:

1. A viral expression vector comprising a live recombinant canine parainfluenza (CPI) vector backbone based on a parainfluenza virus 5 (PIV5) genome and engineered to express a respiratory syncytial virus fusion (RSV F) glycoprotein as a target antigen, wherein:

a. the RSV F protein is encoded by a codon-optimized RSV F gene;

b. the codon-optimized RSV F gene is inserted between the SH and HN gene junctions of the PIV5 genome; and c. the viral expression vector comprises a heterologous nucleic acid sequence having at least 95% sequence identity to SEQ ID NO: 1 and encoding the RSV F protein.

2. The viral expression vector of claim 1, wherein the RSV F protein comprises an amino acid sequence encoded by the nucleic acid sequence of SEQ ID NO:1 or a codon-optimized variant thereof.

3. The viral expression vector of claim 1, wherein the RSV F polypeptide is encoded by an RSV F gene that is codon optimized for expression in a human subject.

4. The viral expression vector of claim 1, wherein the RSV F protein gene is inserted between a SH and HN junction of a CPI antigenomic cDNA.

5. The viral expression vector of claim 1, wherein the CPI vector backbone comprises a PIV5 fusion (F) protein having a 22 amino acid extension as part of its cytoplasmic tail.

6. A pharmaceutical composition comprising the viral expression vector of claim 1 and a pharmaceutically acceptable carrier.

7. The pharmaceutical composition of claim 6, wherein the RSV F protein is a naturally occurring RSV F protein variant or an engineered RSV F protein variant, including a prefusion-stabilized RSV F protein.

8. The pharmaceutical composition of claim 6, wherein the RSV F protein comprises a prefusion-stabilized RSV F protein.

9. The pharmaceutical composition of claim 6, wherein the live recombinant canine parainfluenza (CPI) vector backbone engineered to express the RSV F protein is a prophylactic vaccine against RSV infection.

10. A method of inducing an immune response against RSV in a subject in need thereof, comprising administering to the subject a prophylactic vaccine against RSV infection, wherein the vaccine comprises the pharmaceutical composition of claim 6.

11. The method of claim 10, wherein the vaccine induces RSV F-protein specific serum antibodies and cell mediated responses.

12. The method of claim 11, wherein the RSV specific cell mediate response comprises an increased expression of $CD4^+$ T and $CD8^+$ T cells.

13. The method of claim 11, wherein the RSV-F specific serum antibodies and cell mediated responses are associated with a reduced incidence of an RSV-induced pathological lung response compared to an immune response obtained by administering a formalin-inactivated RSV (FI-RSV).

14. The method of claim 13, wherein the pathological lung response is selected from a group consisting of: peribronchiolitis, perivasculitis, interstitial pneumonia, and alveolitis.

15. The method of claim 10, wherein the vaccine is administered intranasally, intramuscularly, topically, or orally.

16. The method of claim 10, wherein the vaccine is administered in a single or multiple dose regimen.

* * * * *

SEQUENCE LISTING

```
Sequence total quantity: 19
SEQ ID NO: 1            moltype = DNA  length = 17076
FEATURE                 Location/Qualifiers
misc_feature            1..17076
                        note = Synthetic: CPI-RSV-F 5' to 3'nucleic acid sequence
source                  1..17076
                        mol_type = other DNA
                        organism = synthetic construct
SEQUENCE: 1
accaggggga aaacgaagtg gtgactcaaa tcatcgaaga ccctcgagat tacataggtc  60
cggaacctat ggccttcgtg accgacctcg agtcagagta gttcaataag gacctatcaa  120
gtttgggcaa tttttcgtcc ccgacacaaa aatgtcatcc gtgcttaaag catatgagcg  180
attcacactc actcaagaac tgcaagatca gagtgaggaa ggtacaatcc cacctacaac  240
actaaaaccg gtaatcaggg tatttatact aacctctaat aacccagagc taagatcccg  300
gcttcttcta ttttgcctac ggattgttct cagtaatggt gcaagggatt cccatcgctt  360
tggagcatta cttacaatgt tttcgctacc atcagccaca atgctcaatc atgtcaaatt  420
agctgaccag tcaccagaag ctgatatcga aagggtagag atcgatggct ttgaggaggg  480
atcattccgc ttaatcccca atgctcgttc aggtatgagc cgtggagaga tcaatgccta  540
tgctgcactt gcagaagatc tacctgacac actaaaccat gcaacacctt ttgttgattc  600
cgaagtcgag ggaactgcat gggatgagat tgagactttc ttagatatgt gttacagtgt  660
cctaatgcag gcatggatag tgacttgcaa gtgcatgact gcgccagacc aacctgctgc  720
ttctattgag aaacgcctgc aaaaatatcg tcagcaaggc aggatcaacc cgagatatct  780
cctgcaaccg gaggctcgaa gaataatcca gaatgtaatc cgaaagggaa tggtggtcag  840
acatttcctc acctttgaac tgcagcttgc ccgagcacaa agccttgtat caaataggta  900
ttatgctatg gtaggggatg ttggaaagta tatagagaat tgtggaatgg gaggcttctt  960
tttgacacta aaatatgcat taggaaccag atggcccaca cttgctttag ctgcattttc  1020
```

-continued

```
aggagagcta acaaagctaa agtccctcat ggcattatac cagaccccttg gtgagcaggc  1080
ccgatatttg gccctattgg agtcaccaca tttgatggat tttgctgcag caaactaccc  1140
actgctatat agctatgcta tgggaatagg ctatgtgtta gatgtcaaca tgaggaacta  1200
cgctttctcc agatcataca tgaataagac atatttccaa ttgggaatgg aaactgcaag  1260
aaaacaacag ggtgcagttg acatgaggat ggcagaagat ctcggtctaa ctcaagccga  1320
acgcaccgag atggcaaata cacttgccaa attgaccaca gcaaatcgag gggcagacac  1380
caggggagga gtcaacccgt tctcatctat cactgggaca actcaggtgc ccgctgcagc  1440
aacaggtgac acattcgaga gttacatggc agcggatcga ctgaggcaga gatatgctga  1500
tgcaggcacc cacgatgatg agatgccacc attggaagag gaggaagagg acgacacatc  1560
tgcaggtcca cgcactggac taactcttga acaagtggcc ttggacatcc agaacgcagc  1620
agttggagct cccatccata cagatgacct gaatgccgca ctgggtgatc ttgacatcta  1680
gacaattcag atcccaatct taaatcgaca cacctaattg accagttaga tggaactaca  1740
gtggattcca taaggttcct gcctaccatc ggcttttaag aaaaaaatag gcccggacgg  1800
gttagcaaca agcgactgcc gatgccaata acacaatcca caatctacaa tggatcccac  1860
tgatctgagc ttctccccag atgagatcaa taagctcata gagacaggcc tgaatactgt  1920
ggagtatttt acttcccaac aagtcacagg aacatcctct cttggaaaga atacaatacc  1980
accaggggtc acaggactac taaccaatgc tgcagaggca aagatccaag agtcaaccaa  2040
ccatcagaag ggttcagttg gtgggggcgc aaaaccaaag aaaccgcgac caaaaattgc  2100
cattgtgcca gcagatgaca aaacggtgcc cggaaagccg atcccaaacc ctctattagg  2160
tctggactcc accccgagca cccaaactgt gcttgatcta agtgggaaaa cattaccatc  2220
aggatcctat aagggggtta aacttgcgaa atttggaaaa gaaaatctga tgacacggtt  2280
catcgaggaa cccagagaga atcctatcgc aaccaattcc cccatcgatt ttaagagggg  2340
cagggatacc ggcgggttcc atagaaggga gtactcaatc ggatgggtgg gagatgaagt  2400
caaggtcact gagtggtgca atccatcctg ttctccaatc accgctgcag caaggcgatt  2460
tgaatgcact tgtcaccagt gtccagtcac ttgctctgaa tgtgaacgag atacttaata  2520
cagtgagaaa tttggactct cggatgaatc aactggagac aaaagtagat cgcattctct  2580
catctcagtc tctaatccag accatcaaga atgacatagt tggacttaaa gcagggatgg  2640
ctactttaga aggaatgatt acaactgtga aaatcatgga cccgggagtt cccagtaatg  2700
ttactgtgga agatgtacgc aagaaactaa gtaaccatgc tgttgttgtg ccagaatcat  2760
tcaatgatag tttcttgact caatctgaag atgtaatttc acttgatgag ttggctcgac  2820
caactgcaac aagtgttaag aagattgtca ggaaggttcc tcctcagaag gatctgactg  2880
gattgaagat cacactagag caattggcaa aggattgcat cagcaaaccg aagatgaggg  2940
aagagtatct cctcaaaatc aaccaggctt ccagtgaggc tcagctaatt gacctcaaga  3000
aagcaatcat ccgcagtgca atttgatcaa gaaacaccca attacactac actggtatga  3060
cactgtacta accctgaggg ttttagaaaa aacgattaac gataaataag cccgaacact  3120
acacaccacc cgaggcagcc atgccatcca tcagcatccc cgcagacccc accaatccac  3180
gtcaatcaat aaaagcgttc ccaattgtga tcaaccgtga tgggggtgag aaaggtcgct  3240
tggttaaaca actacgcaca acctacttga atgacctaga tactcatgag ccactggtga  3300
cattcgtaaa tacttatgga ttcatctacg aacaggatcg gggaaatacc attgtcggag  3360
aggatcaaca tgggaagaaa agagaggctg tgactgctgc aatggttacc cttggatgtg  3420
ggcctaatct accatcatta gggaatgtcc tgggacaact gagtgaattc caggtcattg  3480
ttaggaagac atccagcaaa gcggaagaga tggtctttga aattgttaag tatccgagaa  3540
tatttcgggg tcatacatta atccagaaag gactagtctg tgtctccgca gaaaaatttg  3600
ttaagtcacc agggaaagta caatctggaa tggactatct cttcattccg acatttctgt  3660
cagtgactta ctgtccagct gcaatcaaat ttcaggtacc tggccccatg ttgaaaatga  3720
gatcaagata cactcagagc ttacaacttg aactaatgat aagaatcctg tgtaagcccg  3780
attcgccact tatgaaggtc catatccctg acaaggaagg aagaggatgt cttgtatcag  3840
tatggttgca tgtatgcaat atcttcaaat caggaaacaa gaatggcagt gagtggcagg  3900
aatactggat gagaaagtgt gctaacatgc aacttgaagt gtcgattgca gatatgtggg  3960
gaccaactat cataattcat gccagaggtc acattcccaa aagtgctaag ttgttttttg  4020
gaaagggtgg atggagctgc catccacttc acgaagttgt tccaagtgtc actaaaacac  4080
tatggtccgt gggctgtgag attacaaagg cgaaggcaat aatacaagag agtagcatct  4140
ctcttctcgt ggagactact gacatcataa gtccaaaagt caaaatttca tctaagcatc  4200
gccgctttgg gaaatcaaat tggggtctgt tcaagaaaac caaatcactg cccaacctga  4260
cggagctgga atgactgacc cccaatcgag actacaccac ctcaaactat aggtgggtgg  4320
tacctcagtg attaatctcg taagcactga tcgtaggcta caacacacta atattatcca  4380
gattagagag cttaattagc tctgtattaa taataacact actattccaa taactggaat  4440
caccagcttg atttatctcc aaaatgattc aaagaaaaca aatcatatta agactatcct  4500
aagcacgaac ccatatcgtc cttcaaatca tgggtactat aattcaattt ctggtggtct  4560
cctgtctatt ggcaggagca ggcagtcttg atccagcagc cctcatgcaa atcggtgtca  4620
ttccaacaaa tgtccggcaa cttatgtatt atactgaggc ctcatcagca ttcattgttg  4680
tgaagttaat gcctacaatt gactcgccga ttagtggatg taatataaca tcaatttcaa  4740
gctataatgc aacagtgaca aaactcctac agccgatcgg tgagaatttg gagacgatta  4800
ggaaccagtt gattccaact cggaggagac gccggtttgc aggggtggtg attggattag  4860
ctgcattagg agtagctact gccgcacagg tcactgccgc agtagcacta gtaaaggcaa  4920
atgaaaatgc tgcggctata ctcaatctca aaaatgcaat ccaaaaaaca aatgcagcag  4980
ttgcagatgt ggtccaggcc acacaatcac taggaacagc agttcaagca gttcaagatc  5040
acataaacag tgtggtaagt ccagcaatta cagcagccaa ttgtaaagcc caagatgcta  5100
tcattggctc aatcctcaat ctctatttga ccgagttgac aactatcttc cacaatcaaa  5160
ttacaaaccc tgcattgagt cctattacaa ttcaagcttt aaggatccta ctagggagta  5220
ccttgccgac tgtggtcgaa aaatctttca atacccagat aagtgcggct gagcttctct  5280
catcagggtt attgacaggc cagattgtgg gattagattt gacctatatg cagatggtca  5340
taaaaattga gctgccaact ttaactgtac aacctgcaac ccagatcata gatctggcca  5400
ccatttctgc attcattaac aatcaagaag tcatggccca attaccaaca cgtgttattg  5460
tgactggcag cttgatccaa gcctatcccg catcgcaatg cactattaca cccaacactg  5520
tgtactgtag gtataatgat gcccaagtac tctcagatga tacgatggct tgcctccaag  5580
gtaacttgac aagatgcacc ttctctccag tggttgggag ctttctcact cgattcgtgc  5640
tgttcgatgg aatagtttat gcaaattgca ggtcgatgtt gtgcaagtgc atgcagcctg  5700
ctgctgtgat cctacagccg agttcatccc ctgtaactgt cattgacatg tacaaatgtg  5760
```

```
tgagtctgca gcttgacaat ctcagattca ccatcactca attggccaat gtaacctaca  5820
atagcaccat caagcttgaa acatcccaga tcttgcctat tgatccgttg gatatatccc  5880
agaatctagc tgcggtgaat aagagtctaa gtgatgcact acaacactta gcacaaagtg  5940
acacatacct ttctgcaatc acatcagcta cgactacaag tgtattatcc ataatagcaa  6000
tctgtcttgg atcgttaggt ttaatattaa taatcttgct cagtgtagtt gtgtggaagt  6060
tattgaccat tgtcgctgct aatcgaaata gaatggagaa ttttgtttat cataattcag  6120
cattccacca ctcacgatct gatctcagtg agaaaaatca acctgcaact cttggaacaa  6180
gataagacag tcatccatta gtaattttta agaaaaaaac gataggaccg aaactagtat  6240
tgaaagaacc gtctcggtca atctaggtaa tcgagctgct accgtctcgg aaagctcaaa  6300
tcatgctgcc tgatccggaa gatccggaaa gcaaaaaagc tacaaggaga acaggaaacc  6360
taattatctg cttcctattc atcttctttc cgtttgtaaa cttcattgtt ccaactctaa  6420
gacacttgct gtcctaacac ctgctatagg ctatccactg catcatctct ttttaagaaa  6480
aaaataggcc cggacgggtt agcaacaagc gactgccggt gccaacaaca caatccacaa  6540
tctacagtcg acgcggccgc caccatggag ctgctgatcc tgaaagccaa cgctattacc  6600
acaatcctga ccgccgtgac attctgcttt gcttccggac agaatatcac cgaggagttc  6660
taccagtcaa catgtagcgc cgtgagcaag gggtacctga gtgcactgcg aaccggatgg  6720
tatacatccg tgattactat cgagctgtct aacatcaaga aaaacaaatg caatggcact  6780
gacgccaaga tcaagctgat caagcaggag ctggataagt acaaaaaatgc tgtgaccgaa  6840
ctgcagctgc tgatgcagag cactccagct accaacaatc gcgcacggag agaactgccc  6900
cggttcatga actataccct gaacaatgca aagaaaacaa atgtgactct gtccaagaaa  6960
cgcaagaggc gcttcctggg atttctgctg ggcgtggggt ctgcaatcgc cagtggagtg  7020
gccgtctcta aagtcctgca cctggagggc gaagtgaaca agatcaaatc agcactgctg  7080
agcacaaaca aggccgtggt cagtctgtca aatggcgtgt ccgtcctgac ttctaaggtg  7140
ctggacctga aaaattatat tgataagcag ctgctgccta tcgtcaacaa acagagctgt  7200
tccatttcta atatcgagac cgtgatcgag ttccagcaga agaacaatag acttctagag  7260
attacaaggg aattttctgt gaacgctggc gtcactaccc ccgtgagtac ctacatgctg  7320
acaaatagtg agctgctgtc actgattaac gacatgccta tcaccaatga tcagaagaaa  7380
ctgatgagta acaatgtgca gatcgtcaga cagcagagtt actcaatcat gtcaatcatt  7440
aaggaggaag tcctggccta cgtggtccag ctgccactgt atggcgtgat cgacactccc  7500
tgctggaaac tgcatacctc acctctgtgc acaactaaca ccaaggaggg gagcaatatc  7560
tgcctgacac gaactgaccg gggatggtac tgtgataacg ccggcagcgt gtccttcttt  7620
ccccaggctg agacctgcaa ggtccagtcc aacagggtgt tctgtgacac tatgaatagc  7680
ctgaccctgc cttccgaagt caacctgtgc aatgtggaca tctttaatcc aaagtacgat  7740
tgtaagatca tgaccagcaa gacagatgtc agctcgagtg tgattacatc actgggggct  7800
atcgtgagct gctacggaaa gactaaatgt accgcaagca acaaaaatcg cggcatcatt  7860
aagaccttca gtaacgggtg cgactatgtc tcaaacaagg gcgtggatac agtgagcgtc  7920
gggaacactc tgtactatgt caataagcag gagggaaaat ccctgtacgt gaagggcgaa  7980
ccaatcatta acttctatga ccccctggtg ttcccttccg acgagtttga tgcctctatt  8040
agtcaggtga acgaaaaaat caatcagagc ctggctttta ttcggaagtc cgatgagctg  8100
ctgcacaacg tgaatgcagt caagtctacc acaaacatta tgatcactac catcattatc  8160
gtgattatcg tcattctgct gtccctgatc gcagtggggc tgctgctgta ctgtaaagcc  8220
agatctacac ccgtgactct gtctaaggat cagctgagtg gaattaacaa tatcgccttt  8280
agcaactgat aggctagcct cctgccatac ttcctactca catcatatct attttaaaga  8340
aaaaataggc ccgaacacta atcgtgccgg cagtgccact gcacacacaa cactacacat  8400
acaatacact acaatggttg cagaagatgc ccctgttagg ggcacttgcc gagtattatt  8460
tcgaacaaca actttaattt ttctatgcac actattagca ttaagcatct ctatccttta  8520
tgagagttta ataacccaaa agcaaatcat gagccaagca ggctcaactg gatctaattc  8580
tagattagga agtatcactg atcttcttaa taatattctc tctgtcgcaa atcagattat  8640
atataactct gcagtcgctc tacctctaca attggacact cttgaatcaa cactccttac  8700
agccattaag tctcttcaaa caagtgacaa gctagaacag aactgctcgt ggggtgctgc  8760
actgattaat gataatagat acattaatgg catcaatcag ttctatttct caattgctga  8820
gggtcgcaag ctgacacttg gcccacttct taatatacct agtttcattc caactgccac  8880
gacaccagag ggctgcacca ggatcccatc attctcgctc accaagacac actggtgtta  8940
tacacacaat gttatcctga atggatgcca ggatcatgta tcctcaaatc aatttgtttc  9000
catgggaatc attgaaccca cttctgccgg gtttccatcc tttcgaaccc taaagactct  9060
atatctcagc gatggggtca atcgtaagag ctgctctatc agtacagttc cgggggggttg  9120
tatgatgtac tgtttcgtct ctactcaacc agagagggat gactactttt ctaccgctcc  9180
tccagaacaa cgaattatta taatgtacta taatgataca atcgtggagc gcataattaa  9240
tccacccggg gtactagatg tatgggcaac attgaaccca ggaacaggaa gcggggtata  9300
ttatttaggt tgggtactct ttccaatata tggcggcgtg attaaagata cgagtttatg  9360
gaataatcaa gcaaataaat actttatccc ccagatggtt gctgctctct gctcacaaaa  9420
ccaggcaact caagtccaaa atgctaagtc atcatactat agcagctggt ttggcaatcg  9480
aatgattcag tctgggatcc tggcatgtcc tcttcaacag gatctaacca atgagtgttt  9540
agttctgccc ttttctaatg atcaggtgct tatgggtgct gaagggagat tatacatgta  9600
tggtgactcg gtgtattact accaaagaag caatagttgg tggcctatga ccatgctgta  9660
taaggtaacc ataacattca ctaatggtca gccatctgct atatcagctc agaatgtgcc  9720
cacacagcag gtccctagac ctgggacagg aagctgctct gcaacaaata gatgtcccgg  9780
tttttgcttg aaaggagtgt atgctgatgc ctggttactg accaaccctt cgtctaccag  9840
tacatttgga tcagaagcaa ccttcactgg ttcttatctc aacgcagcaa ctcagcgtat  9900
caatccgacg atgtatatcg cgaacaacac acagatcata agctcacagc aatttggatc  9960
aagcggtcaa gaagcagcat atggccacac aacttgtttt agggacacag gctctgttat  10020
ggtatactgt atctatatta ttgaattgtc ctcatctctc ttaggacaat ttcagattgt  10080
cccatttatc cgtcaggtga cactatccta aaggcagaag cctccaggtc tgacccagcc  10140
aatcaaagca ttataccaga ccatggaatg cataccaaac attattgaca ctaatgacac  10200
acaaaattgg ttttaagaaa aaccaagaga acaataggcc agaatggctg ggtctcggga  10260
gatattactc cctgaagtcc atctcaattc accaattgta aagcataagc tatactatta  10320
cattctactt ggaaacctcc caaatgagat cgacattgac gatttaggtc cattacataa  10380
tcaaaattgg aatcaaatag cacatgaaga gtctaactta gcccaacgct tggtaaatgt  10440
aagaaatttt ctaattaccc acatccctga tcttagaaag ggccattggc aagagtatgt  10500
```

-continued

```
caatgtaata ctgtggccgc gaattcttcc cttgatcccg gattttaaaa tcaatgacca  10560
attgcctcta ctcaaaaatt gggacaagtt agttaaagaa tcatgttcag taatcaatgc  10620
gggtacttcc cagtgcattc agaatctcag ctatggactg acaggtcgtg ggaacctctt  10680
tacacgatca cgtgaactct ctggtgaccg cagggatatt gatcttaaga cggttgtggc  10740
agcatggcat gactcagact ggaaaagaat aagtgatttt tggattatga tcaaattcca  10800
gatgagacaa ttaattgtta ggcaaacaga tcataatgat cctgatttaa tcacgtatat  10860
cgaaaataga gaaggcataa tcatcataac ccctgaactg gtagcattat ttaacactga  10920
gaatcataca ctaacataca tgacctttga aattgtactg atggtttcag atatgtacga  10980
aggtcgtcac aacattttat cactatgcac agttagcact tacctgaatc ctctgaagaa  11040
aagaataaca tatttattga gccttgtaga taacttagct tttcagatag gtgatgctgt  11100
atataacata attgctttgc tagaatcctt tgtatatgca cagttgcaaa tgtcagatcc  11160
catcccagaa ctcagaggac aattccatgc attcgtatgt tctgagattc ttgatgcact  11220
aaggggaact aatagtttca cccaggatga atcaagaact gtgacaacca atttgatatc  11280
cccattccaa gatctgaccc cagatcttac ggctgaattg ctctgtataa tgaggctttg  11340
gggacacccc atgctcaccg ccagtcaagc tgcgggaaag gtacgcgagt ccatgtgtgc  11400
tggaaaagta ttagactttc ccaccattat gaaaacacta gcctttttcc atactattct  11460
gatcaatgga tacaggagga agcatcatgg agtatggcca cccttaaact taccgggtaa  11520
tgcttcaaag ggtctcacgg aacttatgaa tgacaatact gagataagct atgaattcac  11580
acttaagcat tggaaggaaa tctctcttat aaaattcaag aaatgttttg atgcagacgc  11640
aggtgaggaa ctcagtatat ttatgaaaga taaagcaatt agtgccccaa aacaagattg  11700
gatgagtgtg tttagaagaa gcctaatcaa acagcgccat cagcatcatc aggtccccct  11760
accaaatcca ttcaatcgac ggctattgct aaactttctc ggagatgaca aattcgaccc  11820
gaatgtggag ctacagtatg taacatcagg tgagtatcta catgatgaca cgttttgtgc  11880
atcatattca ctaaaagaga aggaaattaa acctgatggt cgaatttttg caaagttgac  11940
taagagaatg agatcatgtc aagttatagc agaatctctt ttagcgaacc atgctgggaa  12000
gttaatgaaa gagaatggtg ttgtgatgaa tcagctatca ttaacaaaat cactattaac  12060
aatgagtcag attggaataa tatccgagaa agctagaaaa tcgactcgag ataacataaa  12120
tcaacctggt ttccagaata tccagagaaa taaatcacat cactccaagc aagtcaatca  12180
gcgagatcca agtgatgact ttgaattggc agcatctttt ttaactactg atctcaaaaa  12240
atattgttta caatggaggt accagacaat tatcccattt gctcaatcat taaacagaat  12300
gtatggttat cctcatctct ttgagtggat tcacttacgg ctaatgcgta gtacacttta  12360
cgtgggggat cccttcaacc caccagcaga taccagtcaa tttgatctag ataaagtaat  12420
taatggagat atcttcattg tatcacccag aggtggaatt gaagggctat gtcaaaaggc  12480
ttggacaatg atatctatct ctgtgataat tctatctgcc acagagtctg gcacacgagt  12540
aatgagtatg gtgcagggag ataatcaagc aattgctgtc accacacgag taccaaggag  12600
cctgccgact cttgagaaaa agactattgc ttttagatct tgtaatctat tctttgagag  12660
gttaaaatgt aataatttg gattaggtca ccatttgaaa gaacaagaga ctatcattag  12720
ttctcacttc tttgtttata gcaagagaat attctatcag gggaggattc taacgcaagc  12780
cttaaaaaat gctagtaagc tctgcttgac agctgatgtc ctaggagaat gtacccaatc  12840
atcatgttct aatcttgcaa ctactgtcat gaggttaact gagaatggtg ttgaaaaaga  12900
tatctgtttc tacttgaata tctatatgac catcaaacag ctctcctatg atatcatctt  12960
ccctcaagtg tcaattcctg gagatcagat cacattagaa tacataaata atccacacct  13020
ggtatcacga ttggctcttc tgccatccca gctaggaggt ctaaactacc tgtcatgcag  13080
taggctgttc aatcgaaaca taggcgaccc ggtggtttcc gcagttgcag atcttaagag  13140
attaattaaa tcaggatgta tggattactg gatcctttat aacttattag ggagaaaacc  13200
gggaaacggc tcatgggcta ctttagcagc tgacccgtac tcaatcaata tagagtatca  13260
ataccccca actacagctc ttaagaggca cacccaacaa gctctgatgg aactcagtac  13320
gaatccaatg ttacgtggca tattctctga caatgcacag gcagaagaaa ataatcttgc  13380
tagatttctc ctggataggg aggtgatctt tccgcgtgta gctcacatca tcattgagca  13440
aaccagtgtc gggaggagaa aacagattca aggatatttg gattcaacta gatcgataat  13500
gagtaaatca ctagaaatta agcccttgtc caataggaag cttaatgaaa tactggatta  13560
caacatcaat tacctagctt acaatttggc attactcaag aatgctattg aacctccgac  13620
ttatttgaaa gcaatgactc ttgaaacatg tagcatcgac attgcaagga gcctccggaa  13680
gctctcctgg gccccactct tgggtgggag aaatcttgaa ggattagaga cgccagatcc  13740
cattgaaatt actgcaggag cattaattgt tggatcgggc tactgtgaac agtgtgctgc  13800
aggagacaat cgattcacat ggtttttctt gccatctggt atcgagatag gaggggatcc  13860
ccgtgataat cctcctatcc gtgtaccgta cattggctcc aggactgatg agaggagggt  13920
agcctcaatg gcatacatca ggggtgcctc gagtagccta aaagcagttc ttagactggc  13980
gggagtgtac atctgggcat tcggagatac tctggagaat tggatagatg cactggattt  14040
gtctcacact agagttaaca tcacacttga acagctgcaa tccctcaccc cacttccaac  14100
ctctgccaat ctaacccatc ggttggatga tggcacaact accctaaagt ttactcctgc  14160
gagctcttac accttttcaa gtttcactca tatatcaaat gatgagcaat acctgacaat  14220
taatgacaaa actgcagatt caaatataat ctaccaacag ttaatgatca ctggactcgg  14280
aattttagaa acatggaata atcccccaat caatagaaca ttcgaagaat ctaccctaca  14340
tttgcacact ggtgcatcat gttgtgtccg acctgtggac tcctgcatca tctcagaagc  14400
attaacagtc aagccacata ttacagtacc gtacagcaat aaatttgtat ttgatgaaga  14460
cccgctatct gaatatgaga ctgcaaaact ggaatcgtta tcatttcaag cccaattagg  14520
caacattgat gctgtagata tgacaggtaa attaacatta ttgtcccaat tcactgcaag  14580
gcagattatt aatgcaatca ctggactcga tgagtctgtc tctcttacta atgatgccat  14640
tgttgcatca gactatgtct ccaattggat tagtgaatgc atgtatacca aattagatga  14700
attatttatg tattgtgggt gggaactact attggaacta tcctatcaaa tgtattatct  14760
gagggtagtt gggtggagta atatagtgga ttattcttac atgatcttga gaagaatccc  14820
gggtgcagca ttaaacaatc tggcatctac attaagtcat ccaaaacttt tccgacgagc  14880
tatcaaccta gatatagttg ccccttaaa tgctcctcat tttgcatctc tggactacat  14940
caagatgagt gtggatgcaa tactctgggg ctgtaaaaga gtcatcaatg tgctctccaa  15000
tggaggggac ttagaattag ttgtgacatc tgaagatagc cttattctca gtgaccgatc  15060
catgaatctc attgcaagga aattaacttt attatcactg attcaccata atggtttgga  15120
actaccaaag attaaggggt tctctcctga tgagaagtgt ttcgctttga cagaattttt  15180
gaggaaagtg gtgaactcag ggttgagttc aatagagaac ctatcaaatt ttatgtacaa  15240
```

```
tgtggagaac ccacggcttg cagcattcgc cagcaacaat tactacctga ccagaaaatt  15300
attgaattca atacgagata ctgagtcggg tcaagtagca gtcacctcat attatgaatc  15360
attagaatat attgatagtc ttaagctaac cccacatgtg cctggtacct catgcattga  15420
ggatgatagt ctatgtacaa atgattacat aatctggatc atagagtcta atgcaaactt  15480
ggagaagtat ccaattccaa atagccctga ggatgattcc aatttccata actttaagtt  15540
gaatgctcca tcgcaccata ccttacgccc attagggttg tcatcaactg cttggtataa  15600
gggtataagc tgttgcaggt accttgagcg attaaagcta ccacaaggtg atcatttata  15660
tattgcagaa ggtagtggtg ccagtatgac aatcatagaa tacctattcc caggaagaaa  15720
gatatattac aattctttat ttagtagtgg tgacaatccc ccacaaagaa attatgcacc  15780
aatgcctact cagttcattg agagtgtccc atacaagctc tggcaagcac acacagatca  15840
atatcccgag atttttgagg acttcatccc tctatggaac ggaaatgccg ccatgactga  15900
cataggaatg acagcttgtg tagaattcat catcaatcga gtcggcccaa ggacttgcag  15960
tttagtacat gtagatttgg aatcaagtgc aagcttaaat caacaatgcc tgtcaaagcc  16020
gataattaat gctatcatca ctgctacaac tgttttgtgc cctcatgggg tgcttattct  16080
gaaatatagt tggttgccat ttactagatt tagtactttg atcactttct tatggtgcta  16140
ctttgagaga atcactgttc ttaggagcac atattctggt ccagctaatc atgaggttta  16200
tttaatttgt atccttgcca acaactttgc attccagact gtctcgcagg caacaggaat  16260
ggcgatgact ttaaccgatc aagggtttac tttgatatca cctgaaagaa taaatcagta  16320
ttgggatggt cacttgaagc aagaacgtat cgtagcagaa gcaattgata aggtggttct  16380
aggagaagat gctctattca attcgagtga taatgaatta attctcaaat gtggagggac  16440
accaaatgca cggaatctta tcgatatcga gccagtcgca actttcatag aatttgaaca  16500
actgatctgc acaatgttga caacccactt gaaggaaata attgatataa caaggtctgg  16560
aacccaggat tatgaaagtt tattactcac tccttacaat ttaggtcttc ttggtaaaat  16620
cagtacgata gtgagattat taacagaaag gattctaaat catactatca ggaattggtt  16680
gatcctccca ccttcgctcc ggatgatcgt gaagcaggac ttggaattcg gcatattcag  16740
gattacttcc atcctcaatt ctgatcggtt cctgaagctt tctccaaata ggaaatactt  16800
gattacacaa ttaactgcag gctacattag gaaattgatt gagggggatt gtaatatcga  16860
tctaaccaga cctatccaaa aacaaatctg gaaagcatta ggttgtgtag tctattgtca  16920
cgatccagta gatcaaaggg aatcaacaga gtttattgat ataaatatta atgaagaaat  16980
agaccgcggg atcgatggcg aggaaatcta aatatatcaa gaatcagaat tagtttaaga  17040
aaaaagaaga ggattaatct tggttttccc cttggt                          17076

SEQ ID NO: 2           moltype = DNA  length = 25
FEATURE                Location/Qualifiers
misc_feature           1..25
                       note = Synthetic primer: CVL1
source                 1..25
                       mol_type = other DNA
                       organism = synthetic construct
SEQUENCE: 2
accaagggga aaatgaagtg gtgac                                       25

SEQ ID NO: 3           moltype = DNA  length = 24
FEATURE                Location/Qualifiers
misc_feature           1..24
                       note = Synthetic primer: CVL6
source                 1..24
                       mol_type = other DNA
                       organism = synthetic construct
SEQUENCE: 3
ggagaagctc agatcagtgg gatc                                        24

SEQ ID NO: 4           moltype = DNA  length = 25
FEATURE                Location/Qualifiers
misc_feature           1..25
                       note = Synthetic primer: CVL5
source                 1..25
                       mol_type = other DNA
                       organism = synthetic construct
SEQUENCE: 4
acagtggatt ccataaggtt cctgc                                       25

SEQ ID NO: 5           moltype = DNA  length = 27
FEATURE                Location/Qualifiers
misc_feature           1..27
                       note = Synthetic primer: CVL11
source                 1..27
                       mol_type = other DNA
                       organism = synthetic construct
SEQUENCE: 5
cactgacaga aatgtcggaa tgaagag                                     27

SEQ ID NO: 6           moltype = DNA  length = 25
FEATURE                Location/Qualifiers
misc_feature           1..25
                       note = Synthetic primer: CVL10
source                 1..25
                       mol_type = other DNA
                       organism = synthetic construct
```

```
SEQUENCE: 6
tccaggtcac tgttaggaag acatc                                    25

SEQ ID NO: 7           moltype = DNA  length = 26
FEATURE                Location/Qualifiers
misc_feature           1..26
                       note = Synthetic primer: CVL20
source                 1..26
                       mol_type = other DNA
                       organism = synthetic construct
SEQUENCE: 7
gctcgattac ctagattgac cgagac                                   26

SEQ ID NO: 8           moltype = DNA  length = 23
FEATURE                Location/Qualifiers
misc_feature           1..23
                       note = Synthetic primer: CVL17
source                 1..23
                       mol_type = other DNA
                       organism = synthetic construct
SEQUENCE: 8
caagatgcac cttctctcca gtg                                      23

SEQ ID NO: 9           moltype = DNA  length = 24
FEATURE                Location/Qualifiers
misc_feature           1..24
                       note = Synthetic primer: CVL154
source                 1..24
                       mol_type = other DNA
                       organism = synthetic construct
SEQUENCE: 9
atcacactcg agctgacatc tgtc                                     24

SEQ ID NO: 10          moltype = DNA  length = 22
FEATURE                Location/Qualifiers
misc_feature           1..22
                       note = Synthetic primer: CVL152
source                 1..22
                       mol_type = other DNA
                       organism = synthetic construct
SEQUENCE: 10
cgtgagtacc tacatgctga ca                                       22

SEQ ID NO: 11          moltype = DNA  length = 23
FEATURE                Location/Qualifiers
misc_feature           1..23
                       note = Synthetic primer: CVL25
source                 1..23
                       mol_type = other DNA
                       organism = synthetic construct
SEQUENCE: 11
cggattgata cgctgagttg ctg                                      23

SEQ ID NO: 12          moltype = DNA  length = 23
FEATURE                Location/Qualifiers
misc_feature           1..23
                       note = Synthetic primer: CVL19
source                 1..23
                       mol_type = other DNA
                       organism = synthetic construct
SEQUENCE: 12
taactctgca gtcgctctac ctc                                      23

SEQ ID NO: 13          moltype = DNA  length = 22
FEATURE                Location/Qualifiers
misc_feature           1..22
                       note = Synthetic primer: CVL27
source                 1..22
                       mol_type = other DNA
                       organism = synthetic construct
SEQUENCE: 13
cagtctgagt catgccatgc tg                                       22

SEQ ID NO: 14          moltype = DNA  length = 26
FEATURE                Location/Qualifiers
misc_feature           1..26
                       note = Synthetic primer: CVL26
source                 1..26
                       mol_type = other DNA
```

-continued

```
                        organism = synthetic construct
SEQUENCE: 14
gcattcagaa tctcagctat ggactg                                     26

SEQ ID NO: 15           moltype = DNA  length = 24
FEATURE                 Location/Qualifiers
misc_feature            1..24
                        note = Synthetic primer: CVL33
source                  1..24
                        mol_type = other DNA
                        organism = synthetic construct
SEQUENCE: 15
tcaatgatga tgtgagctac acgc                                       24

SEQ ID NO: 16           moltype = DNA  length = 25
FEATURE                 Location/Qualifiers
misc_feature            1..25
                        note = Synthetic primer: CVL32
source                  1..25
                        mol_type = other DNA
                        organism = synthetic construct
SEQUENCE: 16
gctctgatgg aactcagtac gaatc                                      25

SEQ ID NO: 17           moltype = DNA  length = 26
FEATURE                 Location/Qualifiers
misc_feature            1..26
                        note = Synthetic primer: CVL37
source                  1..26
                        mol_type = other DNA
                        organism = synthetic construct
SEQUENCE: 17
ggttctctat tgaactcaac cctgag                                     26

SEQ ID NO: 18           moltype = DNA  length = 25
FEATURE                 Location/Qualifiers
misc_feature            1..25
                        note = Synthetic primer: CVL36
source                  1..25
                        mol_type = other DNA
                        organism = synthetic construct
SEQUENCE: 18
gtgaccgatc catgaatctc attgc                                      25

SEQ ID NO: 19           moltype = DNA  length = 26
FEATURE                 Location/Qualifiers
misc_feature            1..26
                        note = Synthetic primer: CVL42
source                  1..26
                        mol_type = other DNA
                        organism = synthetic construct
SEQUENCE: 19
accaagggga aaaccaagat taatcc                                     26
```